US012251355B2

(12) United States Patent
Stuart et al.

(10) Patent No.: US 12,251,355 B2
(45) Date of Patent: Mar. 18, 2025

(54) MODULAR EXOSKELETON SYSTEMS AND METHODS

(71) Applicant: ROAM ROBOTICS INC., San Francisco, CA (US)

(72) Inventors: Robert Stuart, Arcata, CA (US); Linus Park, Pacifica, CA (US); Ashley Swartz, Daly City, CA (US); Giancarlo Nucci, Seattle, WA (US); Kyle Lamson, Berkeley, CA (US); Kevin Conrad Kemper, San Francisco, CA (US); Timothy Alan Swift, Walnut Creek, CA (US)

(73) Assignee: ROAM ROBOTICS INC., San Francisco, CA (US)

( * ) Notice: Subject to any disclaimer, the term of this patent is extended or adjusted under 35 U.S.C. 154(b) by 801 days.

(21) Appl. No.: 17/332,860

(22) Filed: May 27, 2021

(65) Prior Publication Data

US 2021/0370496 A1     Dec. 2, 2021

Related U.S. Application Data

(60) Provisional application No. 63/058,825, filed on Jul. 30, 2020, provisional application No. 63/030,586, filed on May 27, 2020.

(51) Int. Cl.
*A61H 3/00* (2006.01)
*A61H 1/02* (2006.01)
(Continued)

(52) U.S. Cl.
CPC ............... *A61H 3/00* (2013.01); *A61H 1/024* (2013.01); *B25J 9/0006* (2013.01); *B25J 9/1602* (2013.01);
(Continued)

(58) Field of Classification Search
CPC .......... A61H 3/00; A61H 1/024; B25J 8/0006
See application file for complete search history.

(56) References Cited

U.S. PATENT DOCUMENTS 3,823,711 A    7/1974   Hatton
3,868,952 A    3/1975   Hatton
(Continued)

FOREIGN PATENT DOCUMENTS

CN    101151071 A    3/2008
CN    101960441 A    1/2011
(Continued)

OTHER PUBLICATIONS

European Patent Office Extended Search Report, Application No. 20899495.4 dated Jan. 18, 2024, 11 pages.
(Continued)

*Primary Examiner* — Brian A Dukert
(74) *Attorney, Agent, or Firm* — Davis Wright Tremaine LLP

(57) ABSTRACT

A method of operating a modular exoskeleton system, the method comprising: monitoring for one or more actuator units being operably coupled to or removed from the modular exoskeleton system, the modular exoskeleton system comprising at least a first actuator unit configured to be operably coupled and removed from the modular exoskeleton system; determining that the first actuator unit has been operably coupled to the modular exoskeleton system; determining the first actuator unit has been associated with a first body portion of the user; determining a first new operating configuration based at least in part on the determination that the first actuator unit has been operably coupled to the modular exoskeleton system and the determination that the first actuator unit has been associated with the first body
(Continued)

portion of the user; and setting the first new operating configuration for the modular exoskeleton system.

18 Claims, 19 Drawing Sheets

(51) Int. Cl.
  *B25J 9/00* (2006.01)
  *B25J 9/16* (2006.01)
  *G16H 40/67* (2018.01)
(52) U.S. Cl.
  CPC ....... *G16H 40/67* (2018.01); *A61H 2003/007* (2013.01); *A61H 2201/0214* (2013.01); *A61H 2201/1238* (2013.01); *A61H 2201/1261* (2013.01); *A61H 2201/164* (2013.01); *A61H 2201/1642* (2013.01); *A61H 2201/165* (2013.01); *A61H 2201/1652* (2013.01); *A61H 2201/1671* (2013.01); *A61H 2201/5002* (2013.01); *A61H 2201/5007* (2013.01); *A61H 2201/501* (2013.01); *A61H 2201/5012* (2013.01); *A61H 2201/5025* (2013.01); *A61H 2201/5046* (2013.01); *A61H 2201/5048* (2013.01); *A61H 2201/5058* (2013.01); *A61H 2201/5097* (2013.01); *A61H 2203/0406* (2013.01); *A61H 2203/0431* (2013.01); *A61H 2205/102* (2013.01); *A61H 2230/00* (2013.01)

(56) References Cited

U.S. PATENT DOCUMENTS

| | | | |
|---|---|---|---|
| 3,982,531 | A | 9/1976 | Shaffer |
| 3,993,056 | A | 11/1976 | Rabischong et al. |
| 4,274,399 | A | 6/1981 | Mummert |
| 4,408,600 | A | 10/1983 | Davis |
| 4,523,582 | A | 6/1985 | Barber |
| 4,671,258 | A | 6/1987 | Barthlome |
| 4,944,755 | A | 7/1990 | Hennequin et al. |
| 5,033,457 | A | 7/1991 | Bonutti |
| 5,169,169 | A | 12/1992 | Crawford |
| 5,295,704 | A | 3/1994 | Flock |
| 5,483,838 | A | 1/1996 | Holden |
| 5,780,123 | A | 7/1998 | Kamiyama et al. |
| 5,951,048 | A | 9/1999 | Slaughter |
| 6,117,507 | A | 9/2000 | Smith |
| 6,248,463 | B1 | 6/2001 | Dopp et al. |
| 6,612,340 | B1 | 9/2003 | Lause |
| 6,776,769 | B2 | 8/2004 | Smith |
| 7,086,322 | B2 | 8/2006 | Schulz |
| 7,479,121 | B2 | 1/2009 | Branch |
| 7,628,766 | B1 | 12/2009 | Kazerooni et al. |
| 8,171,570 | B2 | 5/2012 | Adarraga |
| 8,784,350 | B2 | 7/2014 | Cohen |
| 9,205,560 | B1 | 12/2015 | Edsinger et al. |
| 9,709,206 | B2 | 7/2017 | Duttenhoefer et al. |
| 9,821,475 | B1 | 11/2017 | Lynn et al. |
| 9,827,667 | B2 | 11/2017 | Griffith et al. |
| 9,995,321 | B2 | 6/2018 | Lynn et al. |
| 10,012,229 | B2 | 7/2018 | Lynn et al. |
| 10,245,204 | B2 | 4/2019 | Sandler et al. |
| 10,543,110 | B2 | 1/2020 | Piercy et al. |
| 10,548,800 | B1 | 2/2020 | Barnes |
| 10,562,180 | B2 | 2/2020 | Telleria et al. |
| 10,605,365 | B1 | 3/2020 | Griffith et al. |
| 10,611,020 | B2 | 4/2020 | Griffith et al. |
| 10,619,633 | B2 | 4/2020 | Lynn et al. |
| 10,702,742 | B2 | 7/2020 | Sharma et al. |
| 10,780,011 | B2 | 9/2020 | Yang et al. |
| 10,780,012 | B2 * | 9/2020 | Lamb ................ A61H 1/024 |
| 10,966,895 | B2 | 4/2021 | Lamb et al. |
| 11,033,450 | B2 | 6/2021 | Lamb et al. |
| 11,213,417 | B2 | 1/2022 | Piercy et al. |
| 11,259,979 | B2 | 3/2022 | Swift et al. |
| 11,351,083 | B2 | 6/2022 | Swift et al. |
| 11,801,153 | B2 | 10/2023 | Bulea et al. |
| 2001/0029343 | A1 | 10/2001 | Seto et al. |
| 2002/0026794 | A1 | 3/2002 | Shahinpoor et al. |
| 2004/0010720 | A1 | 1/2004 | Singh et al. |
| 2004/0140295 | A1 | 7/2004 | Herres |
| 2004/0176715 | A1 | 9/2004 | Nelson |
| 2005/0066810 | A1 | 3/2005 | Schulz |
| 2005/0102863 | A1 | 5/2005 | Hannon et al. |
| 2005/0107726 | A1 | 5/2005 | Oyen et al. |
| 2005/0177082 | A1 | 8/2005 | Bledsoe |
| 2006/0069336 | A1 | 3/2006 | Krebs et al. |
| 2006/0128538 | A1 | 6/2006 | Sato et al. |
| 2006/0161220 | A1 | 7/2006 | Kobayashi et al. |
| 2006/0173552 | A1 | 8/2006 | Roy |
| 2006/0174760 | A1 | 8/2006 | Rentz |
| 2006/0184280 | A1 | 8/2006 | Oddsson et al. |
| 2006/0207726 | A1 | 9/2006 | Driver et al. |
| 2006/0211956 | A1 | 9/2006 | Sankai |
| 2007/0042710 | A1 | 2/2007 | Mahini et al. |
| 2007/0061107 | A1 | 3/2007 | Vock et al. |
| 2007/0075543 | A1 | 4/2007 | Marx et al. |
| 2007/0239087 | A1 | 10/2007 | Kivisto |
| 2008/0009771 | A1 | 1/2008 | Perry et al. |
| 2008/0161937 | A1 | 7/2008 | Sankai |
| 2008/0195005 | A1 | 8/2008 | Horst et al. |
| 2008/0234608 | A1 | 9/2008 | Sankai |
| 2008/0287850 | A1 | 11/2008 | Adarraga |
| 2009/0024061 | A1 | 1/2009 | Ueda et al. |
| 2009/0118656 | A1 | 5/2009 | Ingimundarson et al. |
| 2010/0040936 | A1 | 2/2010 | Pozin et al. |
| 2010/0114329 | A1 | 5/2010 | Casler et al. |
| 2010/0204627 | A1 | 8/2010 | Kazerooni et al. |
| 2010/0249675 | A1 | 9/2010 | Fujimoto et al. |
| 2010/0270771 | A1 | 10/2010 | Kobayashi et al. |
| 2010/0280424 | A1 | 11/2010 | Kawakami et al. |
| 2011/0059355 | A1 | 3/2011 | Zhang et al. |
| 2011/0071417 | A1 | 3/2011 | Liu et al. |
| 2011/0099026 | A1 | 4/2011 | Oakley et al. |
| 2011/0105966 | A1 | 5/2011 | Kazerooni et al. |
| 2011/0112447 | A1 | 5/2011 | Hsiao-Wecksler et al. |
| 2011/0118635 | A1 | 5/2011 | Yamamoto |
| 2011/0186208 | A1 | 8/2011 | Cartabbia et al. |
| 2011/0290798 | A1 | 12/2011 | Corbett et al. |
| 2012/0059291 | A1 | 3/2012 | Nguyen |
| 2012/0259429 | A1 | 10/2012 | Han et al. |
| 2012/0259431 | A1 | 10/2012 | Han et al. |
| 2012/0271211 | A1 | 10/2012 | Bledsoe |
| 2012/0289870 | A1 | 11/2012 | Hsiao-Wecksler et al. |
| 2012/0328824 | A1 | 12/2012 | Cartabbia et al. |
| 2013/0150980 | A1 | 6/2013 | Swift et al. |
| 2013/0158445 | A1 | 6/2013 | Kazerooni et al. |
| 2013/0172797 | A1 | 7/2013 | Merkley et al. |
| 2013/0245512 | A1 | 9/2013 | Goffer et al. |
| 2013/0289452 | A1 | 10/2013 | Smith et al. |
| 2013/0296746 | A1 | 11/2013 | Herr et al. |
| 2013/0333368 | A1 | 12/2013 | Durfee et al. |
| 2014/0109560 | A1 | 4/2014 | Ilievski et al. |
| 2014/0124557 | A1 | 5/2014 | Velarde |
| 2014/0148745 | A1 | 5/2014 | Castillo |
| 2014/0171838 | A1 | 6/2014 | Aleksov et al. |
| 2014/0207037 | A1 | 7/2014 | Horst |
| 2014/0212243 | A1 | 7/2014 | Yagi et al. |
| 2014/0276264 | A1 | 9/2014 | Caires et al. |
| 2014/0277739 | A1 | 9/2014 | Kornbluh et al. |
| 2014/0318118 | A1 | 10/2014 | Mazzeo et al. |
| 2014/0358290 | A1 | 12/2014 | Kazerooni et al. |
| 2015/0005685 | A1 | 1/2015 | Chetlapalli et al. |
| 2015/0088043 | A1 | 3/2015 | Goldfield et al. |
| 2015/0108191 | A1 | 4/2015 | Velarde |
| 2015/0126911 | A1 | 5/2015 | Abramowicz et al. |
| 2015/0134080 | A1 | 5/2015 | Roh |
| 2015/0157525 | A1 | 6/2015 | Choi et al. |
| 2015/0173927 | A1 | 6/2015 | Castillo |
| 2015/0173993 | A1 | 6/2015 | Walsh et al. |
| 2015/0209214 | A1 | 7/2015 | Herr et al. |
| 2015/0285238 | A1 | 10/2015 | Lynn et al. |
| 2015/0290794 | A1 | 10/2015 | Griffith et al. |

(56) References Cited

U.S. PATENT DOCUMENTS

| | | |
|---|---|---|
| 2015/0302162 A1 | 10/2015 | Hughes et al. |
| 2015/0351991 A1 | 12/2015 | Amundson et al. |
| 2015/0351995 A1 | 12/2015 | Zoss et al. |
| 2016/0045386 A1 | 2/2016 | Sandler et al. |
| 2016/0074272 A1 | 3/2016 | Ahn et al. |
| 2016/0082319 A1 | 3/2016 | Macri et al. |
| 2016/0089591 A1 | 3/2016 | Williamson |
| 2016/0107309 A1 | 4/2016 | Walsh et al. |
| 2016/0143800 A1 | 5/2016 | Hyung et al. |
| 2016/0158087 A1 | 6/2016 | Huang et al. |
| 2016/0213548 A1 | 7/2016 | John et al. |
| 2016/0242986 A1 | 8/2016 | Nagata et al. |
| 2016/0242987 A1 | 8/2016 | Nagata et al. |
| 2016/0252110 A1 | 9/2016 | Galloway et al. |
| 2016/0261224 A1 | 9/2016 | Madrone et al. |
| 2016/0278948 A1 | 9/2016 | Piercy et al. |
| 2016/0297504 A1 | 10/2016 | Saindon et al. |
| 2016/0300156 A1 | 10/2016 | Bowers et al. |
| 2016/0302955 A1 | 10/2016 | Siddiqui et al. |
| 2016/0331557 A1 | 11/2016 | Tong et al. |
| 2016/0331560 A1 | 11/2016 | Tong et al. |
| 2016/0331624 A1 | 11/2016 | Sankai et al. |
| 2016/0346156 A1 | 12/2016 | Walsh et al. |
| 2017/0018761 A1 | 1/2017 | Ogino |
| 2017/0049587 A1 | 2/2017 | Herr et al. |
| 2017/0071812 A1 | 3/2017 | Sandler et al. |
| 2017/0202725 A1 | 7/2017 | Robertson et al. |
| 2017/0246068 A1 | 8/2017 | Schultz et al. |
| 2017/0252255 A1 | 9/2017 | Asano et al. |
| 2017/0279126 A1 | 9/2017 | Dreher |
| 2017/0282360 A1 | 10/2017 | Telleria et al. |
| 2018/0042803 A1 | 2/2018 | Amundson |
| 2018/0056104 A1 | 3/2018 | Cromie et al. |
| 2018/0079071 A1 | 3/2018 | Griffith et al. |
| 2018/0086178 A1 | 3/2018 | Stanek et al. |
| 2018/0092536 A1 | 4/2018 | Sandler et al. |
| 2018/0125152 A1 | 5/2018 | Bruel |
| 2018/0221237 A1 | 8/2018 | Swift et al. |
| 2018/0235830 A1 | 8/2018 | Rokosz et al. |
| 2018/0264642 A1 | 9/2018 | Harding et al. |
| 2018/0283414 A1 | 10/2018 | Lynn et al. |
| 2018/0290009 A1 | 10/2018 | Avila |
| 2018/0296424 A1 | 10/2018 | Lamb et al. |
| 2018/0296425 A1 | 10/2018 | Lamb et al. |
| 2018/0330817 A1 | 11/2018 | Avni et al. |
| 2019/0015233 A1 | 1/2019 | Galloway et al. |
| 2019/0029918 A1 | 1/2019 | Inada et al. |
| 2019/0060156 A1 | 2/2019 | Swift et al. |
| 2019/0060157 A1 | 2/2019 | Lamb et al. |
| 2019/0083002 A1 | 3/2019 | Jang et al. |
| 2019/0099877 A1 | 4/2019 | Goehlich et al. |
| 2019/0105215 A1 | 4/2019 | Dalley et al. |
| 2019/0240103 A1 | 8/2019 | Hepler et al. |
| 2019/0283235 A1 | 9/2019 | Nam et al. |
| 2019/0290464 A1 | 9/2019 | Fleming |
| 2019/0293223 A1 | 9/2019 | Free et al. |
| 2019/0307583 A1 | 10/2019 | Herr et al. |
| 2019/0328604 A1 | 10/2019 | Contreras-Vidal et al. |
| 2019/0344433 A1 | 11/2019 | Lerner |
| 2019/0344434 A1 | 11/2019 | Lerner |
| 2019/0350735 A1 | 11/2019 | Ingimundarson et al. |
| 2019/0383313 A1 | 12/2019 | Fowler et al. |
| 2020/0069441 A1 | 3/2020 | Arose et al. |
| 2020/0114588 A1 | 4/2020 | Wang et al. |
| 2020/0206899 A1 | 7/2020 | Storz et al. |
| 2020/0223071 A1 | 7/2020 | Mahoney et al. |
| 2020/0253808 A1 | 8/2020 | Swift et al. |
| 2020/0410892 A1 | 12/2020 | Otsuki et al. |
| 2021/0162262 A1 | 6/2021 | Lee |
| 2021/0177686 A1 | 6/2021 | Lamson et al. |
| 2021/0369539 A1 | 12/2021 | Campbell et al. |
| 2021/0369540 A1 | 12/2021 | Kemper et al. |
| 2021/0369541 A1 | 12/2021 | Stuart et al. |
| 2021/0369542 A1 | 12/2021 | Stuart et al. |
| 2021/0370493 A1 | 12/2021 | Samia et al. |
| 2021/0370494 A1 | 12/2021 | Hurley et al. |
| 2021/0370495 A1 | 12/2021 | Swartz et al. |
| 2021/0370496 A1 | 12/2021 | Stuart et al. |
| 2021/0386611 A1 | 12/2021 | Dalley et al. |

FOREIGN PATENT DOCUMENTS

| | | |
|---|---|---|
| CN | 103412003 A | 11/2013 |
| CN | 104582668 A | 4/2015 |
| CN | 105205436 A | 12/2015 |
| CN | 204814712 U | 12/2015 |
| CN | 105264255 A | 1/2016 |
| CN | 105590409 A | 5/2016 |
| CN | 105816301 A | 8/2016 |
| CN | 105992554 A | 10/2016 |
| CN | 106029039 A | 10/2016 |
| CN | 106137489 A | 11/2016 |
| CN | 106413998 A | 2/2017 |
| CN | 106420279 A | 2/2017 |
| CN | 106650224 A | 5/2017 |
| CN | 110545777 A | 12/2019 |
| CN | 110868964 A | 3/2020 |
| CN | 111135031 A | 5/2020 |
| CN | 111278398 A | 6/2020 |
| CN | 111571568 A | 8/2020 |
| DE | 102011107580 A1 | 1/2013 |
| EP | 2827809 A1 | 1/2015 |
| EP | 3173191 A2 | 5/2017 |
| EP | 3539528 A1 | 9/2019 |
| EP | 3576707 A4 | 3/2021 |
| FR | 1463850 A | 7/1966 |
| JP | S601405 A | 1/1985 |
| JP | 1987501723 A | 7/1987 |
| JP | S62501723 A | 7/1987 |
| JP | 1988199965 A | 8/1988 |
| JP | S63199965 A | 8/1988 |
| JP | H07163607 A | 6/1995 |
| JP | 2000051289 A | 2/2000 |
| JP | 2005118959 A | 5/2005 |
| JP | 2005296103 A | 10/2005 |
| JP | 2006000347 A | 1/2006 |
| JP | 2007282991 A | 11/2007 |
| JP | 2010263934 A | 11/2010 |
| JP | 2011058564 A | 3/2011 |
| JP | 2011173211 A | 9/2011 |
| JP | 2012501739 A | 1/2012 |
| JP | 3179088 U | 10/2012 |
| JP | 2012532001 | 12/2012 |
| JP | 2012532001 A | 12/2012 |
| JP | 2014023773 A | 2/2014 |
| JP | 2015008938 A | 1/2015 |
| JP | 2015089386 A | 5/2015 |
| JP | 2016137146 | 8/2016 |
| JP | 2017086296 A | 5/2017 |
| JP | 2017154210 A | 9/2017 |
| JP | 2018184266 A | 11/2018 |
| JP | 2019077037 A | 5/2019 |
| JP | 2019093464 A | 6/2019 |
| JP | 2019111635 A | 7/2019 |
| JP | 2020506030 A | 2/2020 |
| JP | 2020518295 A | 6/2020 |
| JP | 6860743 B2 | 4/2021 |
| KR | 10-2008-0048450 A | 6/2008 |
| KR | 10-2011-0104781 A | 9/2011 |
| KR | 10-2012-0025571 A | 3/2012 |
| KR | 10-2014-0062931 A | 5/2014 |
| KR | 20160020780 A | 2/2016 |
| KR | 101812603 B1 | 12/2017 |
| KR | 10-2020-0052323 A | 5/2020 |
| KR | 10-2020-0144460 A | 12/2020 |
| KR | 10-2021-0033449 A | 3/2021 |
| SU | 251758 | 11/1970 |
| WO | 8603816 A1 | 7/1986 |
| WO | 9722782 A1 | 6/1997 |
| WO | 0004852 A1 | 2/2000 |
| WO | 2008129096 A1 | 10/2008 |
| WO | 2009081710 A1 | 7/2009 |
| WO | 2010124172 A2 | 10/2010 |
| WO | 2011007569 A1 | 1/2011 |

(56) References Cited

FOREIGN PATENT DOCUMENTS

| WO | 2011043095 A1 | 4/2011 |
|----|---------------|--------|
| WO | 2012044621 A1 | 4/2012 |
| WO | 2012086202 A1 | 6/2012 |
| WO | 2012124853 A1 | 9/2012 |
| WO | 2013142777 A1 | 9/2013 |
| WO | 2013152929 A1 | 10/2013 |
| WO | 2014109799 A1 | 7/2014 |
| WO | 2015080596 A1 | 6/2015 |
| WO | 2015104832 A1 | 7/2015 |
| WO | 2016147195 A1 | 9/2016 |
| WO | 2016166442 A1 | 10/2016 |
| WO | 2016166588 A1 | 10/2016 |
| WO | 2016171548 A1 | 10/2016 |
| WO | 2016207855 A1 | 12/2016 |
| WO | 2017110453 A1 | 6/2017 |
| WO | 2017218661 A1 | 12/2017 |
| WO | 2018144937 A1 | 8/2018 |
| WO | 2018191710 A1 | 10/2018 |
| WO | 2018218336 A1 | 12/2018 |
| WO | 2018236225 A1 | 12/2018 |
| WO | 2019046488 A1 | 3/2019 |
| WO | 2019046489 A1 | 3/2019 |
| WO | 2019122364 A1 | 6/2019 |
| WO | 2019131386 A1 | 7/2019 |
| WO | 2019183397 A1 | 9/2019 |
| WO | 2019187030 A1 | 10/2019 |
| WO | 2020049886 A1 | 3/2020 |
| WO | 2021096874 A1 | 5/2021 |

OTHER PUBLICATIONS

Israel Notice of Deficiencies for Patent Application 269860 dated Jan. 10, 2024, 4 pages.
Israel Notice of Deficiencies for Patent Application 269860 dated Nov. 14, 2023, 4 pages.
Japan Office Action, Application No. 2022-573514 dated Dec. 27, 2023, 3 pages.
Japan Office Action, Application No. 2022-573520 dated Jan. 4, 2024, 4 pages.
Japan Office Action, Application No. 2023-034202 dated Jan. 9, 2024, 4 pages.
Japan PTO Rejection of Application No. 2022-573509 dated Dec. 4, 2023, 5 pages.
Japan PTO Rejection of Application No. 2022-573517 dated Jan. 9, 2024, 2 pages.
Japan PTO Rejection of Application No. 2022-573519 dated Jan. 9, 2024, 2 pages.
Japanese IPO Notification of Reason for Rejection of Application No. 2022-573516, Jan. 15, 2024, 3 pages.
USPTO Notice of Allowance in U.S. Appl. No. 17/119,830 dated Nov. 8, 2023, 9 pages.
USPTO Office Action in U.S. Appl. No. 16/838,347 dated Jan. 24, 2023, 7 pages.
USPTO Office Action in U.S. Appl. No. 17/327,121 dated Aug. 29, 2023, 8 pages.
USPTO Office Action in U.S. Appl. No. 17/558,481 dated Nov. 29, 2023, 17 pages.
Canadian IPO Notice of Allowance dated Mar. 19, 2024, Patent Application No. 3,051, 105, 1 page.
Chu, "Human-Expsystem Adaptation," MIT School of Engineering, Oct. 2018 [retrieved Apr. 25, 2024 from https://engineering.mit.edu/engage/engineering-in-action/human-exosystem-adaptation/,] 9 pages.
Dephy, "Build Faster a Safe Robotics Platform that Actually Works?" Retrieved Apr. 25, 2024 from https://web.archive.org/web/20221226232116/https://dephy.com/faster/, 11 pages.
European Patent Office Extended Search Report dated Apr. 8, 2024, Application No. 20899495.4, 10 pages.
European Patent Office Extended Search Report dated Jan. 29, 2024, Application No. 23196713.4, 7 pages.
European Patent Office Extended Search Report, Application No. 21812810.6 dated Jan. 18, 2024, 8 pages.
European Patent Office Extended Search Report, Application No. 21813358.5 dated Jan. 24, 2024, 9 pages.
European Patent Office Supplementary Search Report dated Jan. 30, 2024, Application No. 21814414.5, 12 pages.
European Patent Office Supplementary Search Report, Application No. 21814414.5, 12 pages.
Japan First Office Action, Application No. 2022-535872 dated Feb. 15, 2024, 8 pages.
Japan First Office Action, Application No. 2022-573518 dated Apr. 22, 2024, 2 pages.
Japan IPO Office Action dated Feb. 13, 2024, Application No. 2022-573515, 5 pages.
Japan IPO Trial Decision Allowing Application No. 2019-554877 dated Apr. 1, 2024, 2 pages.
MIT School of Engineering, "Human-exosystem Adaptation," https://www.youtube.com/watch?v=GXGHi_n1uR0, Oct. 4, 2018, 2 pages.
University of Michigan, "Understanding Exoskeletons Use Motivation," 2020 [retrieved Apr. 25, 2024 from https://neurobionics.robotics.umich.edu/research/biomechanical-science/dephy-ankle-exoskeletons/,] 4 pages.
USPTO Office Action dated Apr. 4, 2024, U.S. Appl. No. 16/838,347, 7 pages.
USPTO Office Action dated Mar. 7, 2024, U.S. Appl. No. 17/119,825, 18 pages.
USPTO Office Action in U.S. Appl. No. 16/827,484 dated Dec. 4, 2023, 18 pages.
USPTO Office Action in U.S. Appl. No. 16/827,484 dated Mar. 15, 2023, 13 pages.
USPTO Office Action in U.S. Appl. No. 16/838,347 dated Jun. 8, 2023, 5 pages.
USPTO Office Action in U.S. Appl. No. 17/119,825 dated May 23, 2023, 19 pages.
USPTO Office Action in U.S. Appl. No. 17/119,830 dated Mar. 15, 2023, 23 pages.
USPTO Office Action in U.S. Appl. No. 17/329,632 dated Feb. 15, 2023, 16 pages.
Chinese Patent Office Decision of Rejection dated Oct. 10, 2022; Application No. 201880024597; 11 pages.
Chinese Patent Office Notification to Grant Patent Right for Invention dated Nov. 4, 2022; Application No. 201880056518.3; 2 pages.
Chinese Patent Office Second Office Action and Supplementary Search Report dated Apr. 25, 2022; Application No. 201880023218.5; 15 pages.
Chinese Patent Office Second Office Action and Supplementary Search Report dated Mar. 30, 2022; Application No. 201880024598; 15 pages.
Chinese Patent Office Second Office Action dated Jul. 13, 2022; Application No. 201880056518.3; 6 pages.
Chinese Patent Office Supplemental Search Report dated Jul. 4, 2022, Application No. 201880056518.3, 4 pages.
Chinese Patent Office Third Office Action dated Oct. 20, 2022; Application No. 201880023218.5; 8 pages.
European Patent Office Communication under Rule 71(3) EPC dated Apr. 19, 2022, Application No. 18 850 236.3, 46 pages.
European Patent Office Communication under Rule 71(3) EPC dated Nov. 29, 2022, Application No. 18 783 314.9, 46 pages.
European Patent Office Communication Under Rule 71(3) EPC, Application No. 18 783 814.9 dated Aug. 11, 2022, 44 pages.
European Patent Office Extended Search Report dated Oct. 18, 2022, Patent Application No. 22181044.3-1122, 7 bages.
European Patent Office Notice of Intention to Grant, Application No. 18783814.9, Nov. 29, 2022, 8. pages.
Huang et al., "Interactive learning for sensitivity factors of a human-powered augmentation lower exoskeleton," 2015 IEEE/RSJ International Conference on Intelligent Robots and Systems (IROS), Sep. 28, 2015, 7 pages.
International Search Report and Written Opinion mailed Apr. 26, 2018, International Patent Application No. PCT/US2018/016729, filed Feb. 2, 2018, 7 pages.
International Search Report and Written Opinion mailed Aug. 26, 2021, Patent Application No. PCT/US2021/034444, 7 pages.

(56) References Cited

OTHER PUBLICATIONS

International Search Report and Written Opinion mailed Aug. 26, 2021, Patent Application No. PCT/US2021/034447, 7 pages.
International Search Report and Written Opinion mailed Aug. 26, 2021, Patent Application No. PCT/US2021/034593, 10 pages.
International Search Report and Written Opinion mailed Dec. 1, 2022, Patent Application No. PCT/US2022/075098, 12 pages.
International Search Report and Written Opinion mailed Dec. 1, 2022, Patent Application No. PCT/US2022/075099, 12 pages.
International Search Report and Written Opinion mailed Dec. 5, 2022, Patent Application No. PCT/US2022/075097, 11 pages.
International Search Report and Written Opinion mailed Dec. 6, 2018, International Patent Application No. PCT/US2018/048638, filed Aug. 29, 2018, 8 pages.
International Search Report and Written Opinion mailed Dec. 6, 2018, Patent Application No. PCT/US2018/048639, 7 pages.
International Search Report and Written Opinion mailed Dec. 6, 2022, Patent Application No. PCT/US2022/075095, 10 pages.
International Search Report and Written Opinion mailed Jul. 18, 2016, International Patent Application No. PCT/US2016/024366, filed Mar. 25, 2016, 7 pages.
International Search Report and Written Opinion mailed Jul. 19, 2018, International Patent Application No. PCT/US2018/027643, filed Apr. 13, 2018, 7 pages.
International Search Report and Written Opinion mailed Jun. 3, 2021, Patent Application No. PCT/US2021/019711, 12 pages.
International Search Report and Written Opinion mailed Mar. 30, 2021, Patent Application No. PCT/US2020/064647, 10 pages.
International Search Report and Written Opinion mailed Nov. 29, 2022, International Patent Application No. PCT/US2022/075094, filed Aug. 17, 2022, 11 pages.
International Search Report and Written Opinion mailed Nov. 29, 2022, International Patent Application No. PCT/US2022/075096, filed Aug. 17, 2022, 11 pages.
International Search Report and Written Opinion mailed Sep. 2, 2021, Patent Application No. PCT/US2021/034030, 9 pages.
International Search Report and Written Opinion mailed Sep. 2, 2021, Patent Application No. PCT/US2021/034450, 9 pages.
International Search Report and Written Opinion mailed Sep. 9, 2021, Patent Application No. PCT/US2021/034443, 8 pages.
International Search Report and Written Opinion mailed Sep. 9, 2021, Patent Application No. PCT/US2021/034579, 8 pages.
International Search Report and Writtent Opinion mailed Aug. 26, 2021, Patent Application No. PCT/US2021/034468, 8 pages.
Israel Notice of Deficiencies for Patent Application No. 269860 dated Jul. 25, 2022, 5 pages.
Japan Final Office Action and Decision to Reject Amendment of Application No. 2019-554877 dated Nov. 7, 2022, 4 pages.
Japan Final Rejection of Application No. 2019-563328 dated Jul. 6, 2022, 2 pages.
Japan Patent Office, "Final Rejection" in Applicaiton No. 2019-563328, Sep. 9, 2022, 4 pages.
Japanese IPO Final Rejection of Application No. 2019-563328, Aug. 9, 2022, 2 pages.
Japanese IPO Notification of Reason for Rejection of Application No. 2020-512042, Jun. 27, 2022, 2 pages.
National Intellectual Property Administration, P. R. China, "2nd Office Action" in Application No. 201880023218.5, Apr. 25, 2022, 15 pages.
Notification of Grant of Chinese Patent Application No. 201880056709 dated May 18, 2022, 2 pages.
Tamez-Duque et al., "Real-time strap pressure sensor system for powered exoskeletons," Sensors 15(2):4550-4563, Feb. 2015.
Taniguchi, "Flexible Artificial Muscle Actuator Using Coiled Shape 5 Memory Alloy Wires," APCBEE Procedia 7:54-59, Jan. 1, 2013.
Israel Notice of Deficiencies for Patent Application 269860 dated Jul. 25, 2022, 5 pages.

Branham, "3 Advantages of Using an Oval Bore Compact Cylinder," W.C. Branham Blog—Solutions in Motion TM. Retrieved Feb. 9, 2023, from https://blog.wcbranham.com/oval-bore-compact-cylinder, Jan. 12, 2018, 7 pages.
Lamb, WO 2018191710 A1 Oct. 18, 2018 (full text). [online] [retrieved on Feb. 9, 2023]. Retrieved from Clarivate Analytics, 2018, 15 pages.
Israel Notice of Acceptance for Patent Application No. 268306 dated Feb. 1, 2023, 3 pages.
Japan First Office Action, Application No. 2022-072995 dated Mar. 8, 2023, 2 pages.
Canadian IPO Office Action and Examination Search Report dated Mar. 21, 2023, Patent Application No. 3,051,105, 7 pages.
Chinese Patent Office Fourth Office Action dated Mar. 31, 2023, Application No. 201880023218.5; 7 pages.
USPTO Office Action in U.S. Appl. No. 17/558,481 dated Mar. 23, 2023, 49 pages.
USPTO Office Action in U.S. Appl. No. 16/862,400 dated Mar. 22, 2023, 13 pages.
Chinese Patent Office First Office Action dated Jun. 16, 2023; Application No. 202111540872.3; 14 pages.
Chinese Patent Office Notification to Grant Patent Right for Invention dated Jul. 10, 2023; Application No. 201880024597.X; 2 pages.
European Patent Office Notice of Intention to Grant, Application No. 18748599.0, Aug. 16, 2023, 52 pages.
Israel Notice before Acceptance for Patent Application No. 282165 dated May 24, 2023, 3 pages.
Israel Notice Notice before Acceptance for Patent Application No. 282165 dated Apr. 18, 2023, 3 pages.
Japan PTO Rejection of Application No. 2019-563328 dated Jul. 13, 2023, 3 pages.
USPTO Non-Final Office Action in U.S. Appl. No. 17/327,121 dated Aug. 29, 2023, 8 pages.
USPTO Notice of Allowance of U.S. Appl. No. 17/729,934 dated Aug. 23, 2023, 22 pages.
Chinese Patent Office Decision on Rejection dated Oct. 10, 2022; Application No. 201880024597; 11 pages.
European Patent Office Intention to Grant, Application No. 18 783 814.9 dated Nov. 29, 2022, 83 pages.
Israel Notice of Acceptance for Patent Application No. 272621 dated Dec. 22, 2022, 4 pages.
Israel Notice of Deficiencies for Patent Application No. 272623 dated Dec. 7, 2022, 4 pages.
Israel Notice of Deficiencies for Patent Application No. 282165 dated Dec. 18, 2022, 4 pages.
Japan Decision to Grant Application No. 2020-512042 dated Jan. 13, 2023, 2 pages.
Dephy, "Getting Started," retrieved May 28, 2024 from https://dephy.com/start/, 23 pages.
Israel Notice of Acceptance dated Apr. 1, 2024, Patent Application No. 272623, 3 pages.
USPTO Office Action in U.S. Appl. No. 16/862,400 dated My 22, 2024, 20 pages.
Yoshikawa, "Human Interface Using Hand Movement Recognition Method Based on Myoelectricity," Next Generation Human Interface Development Frontier, Jun. 11, 2013, 14 pages.
U.S. Appl. No. 17/332,818, filed May 27, 2021.
U.S. Appl. No. 17/331,956, filed May 27, 2021.
U.S. Appl. No. 17/331,961, filed May 27, 2021.
U.S. Appl. No. 17/332,203, filed May 27, 2021.
U.S. Appl. No. 17/332,172, filed May 27, 2021.
U.S. Appl. No. 17/332,507, filed May 27, 2021.
USPTO Office Action dated Jan. 23, 2025, U.S. Appl. No. 17/331,961, 25 pages.
USPTO Office Action in U.S. Appl. No. 17/332,172 dated Dec. 17, 2024, 39 pages.
USPTO Office Action in U.S. Appl. No. 17/558,481 dated Dec. 20, 2024, 12 pages.
Canadian Intellectual Property Office Office Action dated Dec. 6, 2024, Application No. 3,072,504, 6 pages.
Canadian IPO Office Action dated Dec. 5, 2024, Patent Application No. 3,072,622, 7 pages.

(56) References Cited

OTHER PUBLICATIONS

Chinese Patent Office First Office Action dated Jan. 15, 2025; Application No. 202180040509.7; 3 pages.
Chinese Patent Office First Office Action dated Jan. 17, 2025, Application No. 202180045080.0; 10 pages.
Chinese Patent Office First Office Action dated Jan. 17, 2025; Application No. 202180045079.8; 10 pages.
Chinese Patent Office First Office Action dated Jan. 17, 2025; Application No. 202189945078.3; 13 pages.
Chinese Patent Office Notification of Grant of Application No. 20211150872.3, Nov. 19, 2024, 2 pages.
European Patent Office Exam Report dated Jan. 14, 2025, Application No. 22181044.3, 4 pages.
Israel Notice of Deficiencies for Patent Application 293829 dated Dec. 9, 2024, 5 pages.
Japan Decision to Grant Application No. 2022-176048 dated Nov. 14, 2024, 2 pages.

\* cited by examiner

MODULAR EXOSKELETON SYSTEMS AND METHODS

CROSS-REFERENCE TO RELATED APPLICATIONS

This application is a non-provisional of and claims priority to U.S. Provisional Patent Application No. 63/030,586, filed May 27, 2020, entitled "POWERED DEVICE FOR IMPROVED USER MOBILITY AND MEDICAL TREATMENT". This application is hereby incorporated herein by reference in its entirety and for all purposes.

This application is a non-provisional of and claims priority to U.S. Provisional Patent Application No. 63/058,825, filed Jul. 30, 2020, entitled "POWERED DEVICE TO BENEFIT A WEARER DURING TACTICAL APPLICATIONS". This application is hereby incorporated herein by reference in its entirety and for all purposes.

This application is also related to U.S. Non-Provisional Applications filed the same day as this application entitled "POWERED MEDICAL DEVICE AND METHODS FOR IMPROVED USER MOBILITY AND TREATMENT", "FIT AND SUSPENSION SYSTEMS AND METHODS FOR A MOBILE ROBOT", "BATTERY SYSTEMS AND METHODS FOR A MOBILE ROBOT", "CONTROL SYSTEM AND METHOD FOR A MOBILE ROBOT". "USER INTERFACE AND FEEDBACK SYSTEMS AND METHODS FOR A MOBILE ROBOT", and "DATA LOGGING AND THIRD-PARTY ADMINISTRATION OF A MOBILE ROBOT" and having respective application Ser. Nos. 17/332,818, 17/331,956 17/331,961, 17/332,203, 17/332,172 and 17/332,507. These applications are hereby incorporated herein by reference in their entirety and for all purposes.

BRIEF DESCRIPTION OF THE DRAWINGS

FIG. 18b illustrates a side view of the pneumatic actuator of FIG. 18a in an expanded configuration showing the cross section of FIG. 18a.

Figure 1:
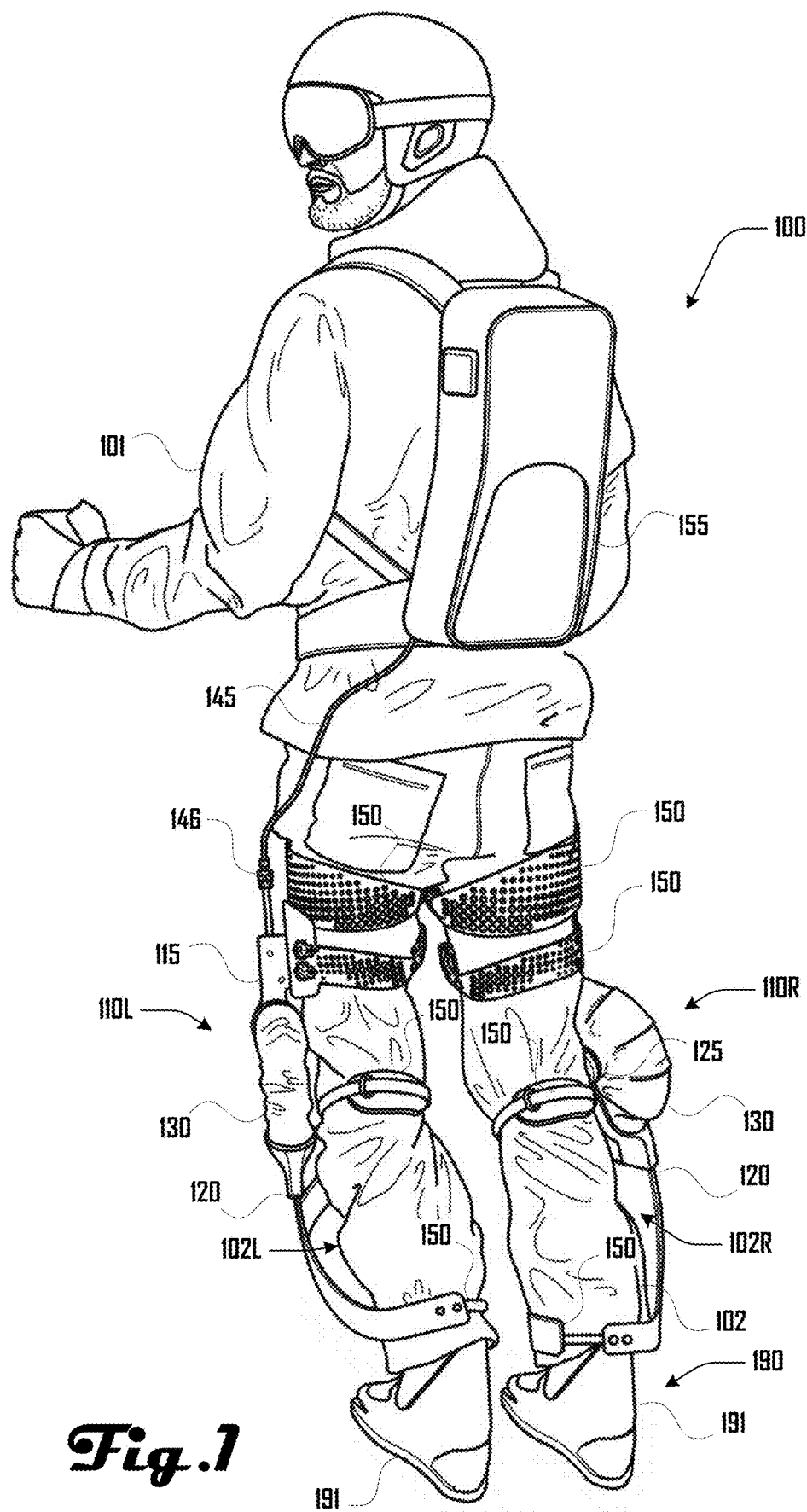
FIG. 1 is an example illustration of an embodiment of an exoskeleton system being worn by a user.

It should be noted that the figures are not drawn to scale and that elements of similar structures or functions are generally represented by like reference numerals for illustrative purposes throughout the figures. It also should be noted that the figures are only intended to facilitate the description of the preferred embodiments. The figures do not illustrate every aspect of the described embodiments and do not limit the scope of the present disclosure.

DETAILED DESCRIPTION

The following disclosure also includes example embodiments of the design of novel exoskeleton devices. Various preferred embodiments include: a leg brace with integrated actuation, a mobile power source and a control unit that determines the output behavior of the device in real-time.

A component of an exoskeleton system that is present in various embodiments is a body-worn, lower-extremity brace that incorporates the ability to introduce torque to the user. One preferred embodiment of this component is a leg brace that is configured to support the knee of the user and includes actuation across the knee joint to provide assistance torques in the extension direction. This embodiment can connect to the user through a series of attachments including one on the boot, below the knee, and along the user's thigh. This preferred embodiment can include this type of leg brace on both legs of the user.

The present disclosure teaches example embodiments of a fluidic exoskeleton system that includes one or more adjustable fluidic actuators. Some preferred embodiments include a fluidic actuator that can be operated at various pressure levels with a large stroke length in a configuration that can be oriented with a joint on a human body.

In some cases, the system can be designed to support multiple configurations in a modular configuration. A preferred embodiment is a modular configuration that is designed to operate in either a single-knee configuration or in a dual-knee configuration as a function of how many of the brace components or actuation units are donned by the user. Yet another embodiment can use a single fluidic and electric power pack to power an assistive knee brace on one leg, and a below knee prosthetic on the other leg.

In a modular configuration, in some embodiments it may be required that a single fluidic and electric power pack be configured to support the fluidic and electrical power requirements of various potential configurations. One preferred configuration is a fluidic and electrical power supply that can be configured to power a dual-knee configuration or a single-knee configuration. In various embodiments, such a fluidic and electrical power supply would need to support the power requirements of both configurations and then appropriately direct the fluidic and electrical power to operate effectively in a given configuration. Various embodiments exist to support the array of potential modular system configurations, such as multiple batteries, more than two actuator units, more than one power pack, etc.

In the example case of a modular exoskeleton system, it can be desirable in some embodiments for operational control software to operate with an understanding of which actuation units are operational within the system. In one embodiment of a modular dual-knee system that can also operate in a single-knee configuration, operational control software can generate references differently when in a two-leg configuration and when in a single-leg configuration. Specifically, such an embodiment may use a coordinated control approach to generate references where it is using inputs from both legs to determine the desired operation; however, in a single-leg configuration, the available sensor information may have changed, so the system can implement a different strategy based on different sensor information being available. In various embodiments this can be done to maximize the performance of the system for the given configuration or account for variations in available sensor information. For clarity, these embodiments are not limited to the examples given above and include any combination of configurations of actuation units, power packs, as well as any related sensor information that can be associated with actuation units, power packs, or sensors independently located on the user.

Another unique consideration in some examples of operational control software can be if a user's needs are different between individual body joints, such as between the left or right knee. In such a scenario, it may be beneficial for the exoskeleton system to change the torque references generated in each leg to tailor the experience for the user. One example embodiment is that of a dual-knee exoskeleton where a user has significant pain issues in a single leg, but not in the other leg. In such a case, the system can include the ability for the system to scale the output torques on the unaffected limb to best meet the needs of the user.

Figure 2:
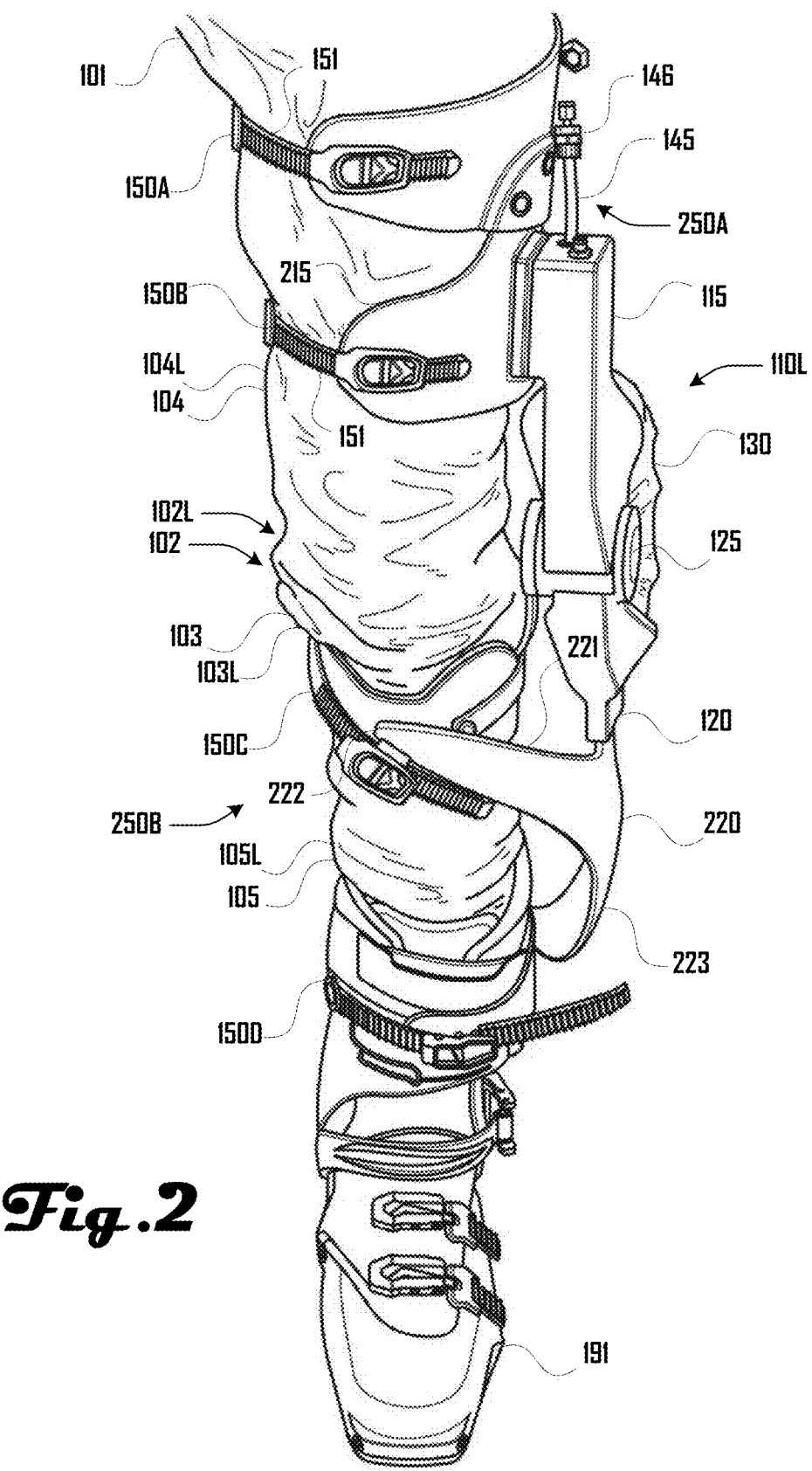
FIG. 2 is a front view of an embodiment of a leg actuation unit coupled to one leg of a user.
Figure 3:
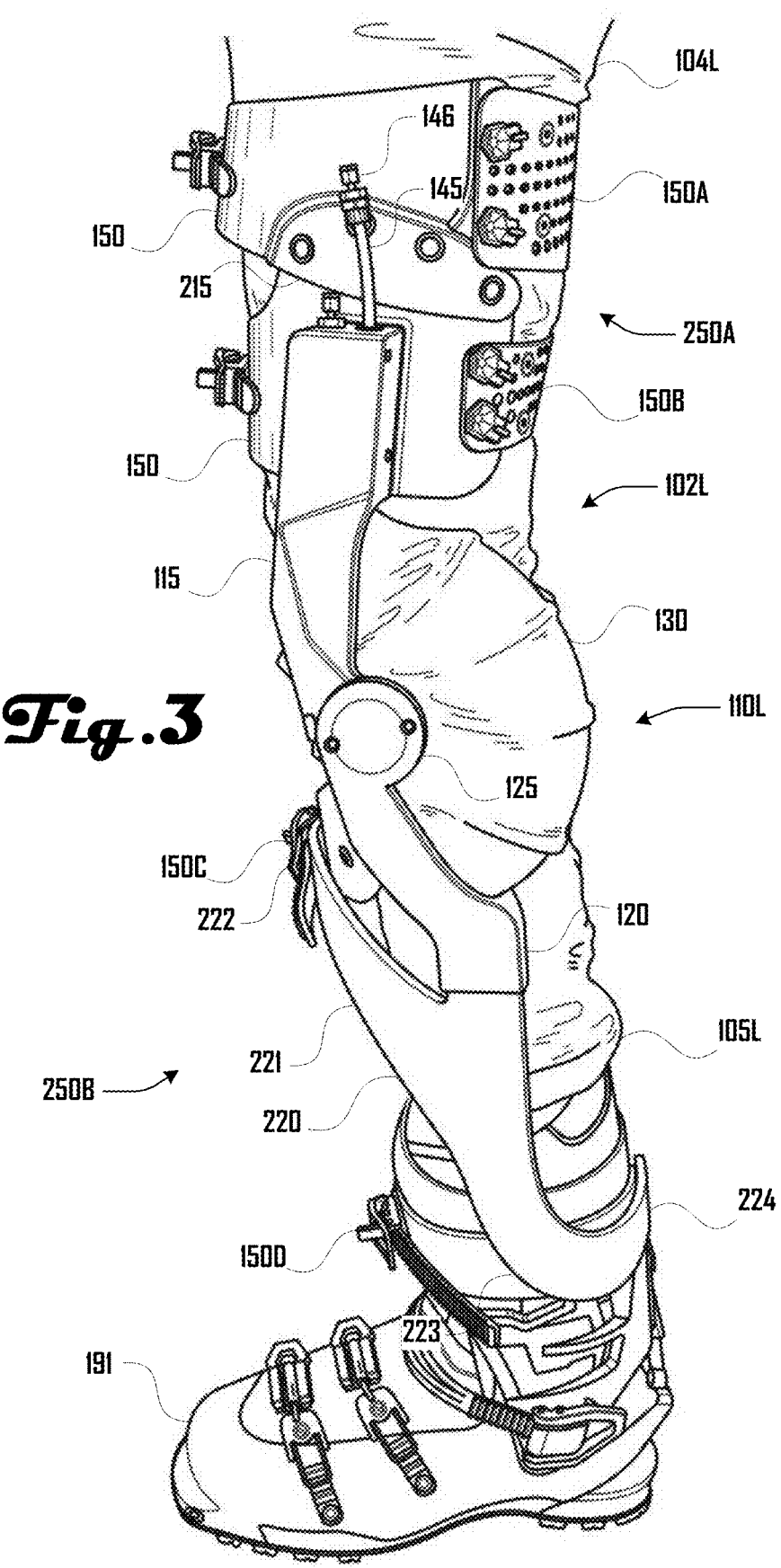
FIG. 3 is a side view of the leg actuation unit of FIG. 3 coupled to the leg of the user.
Figure 4:
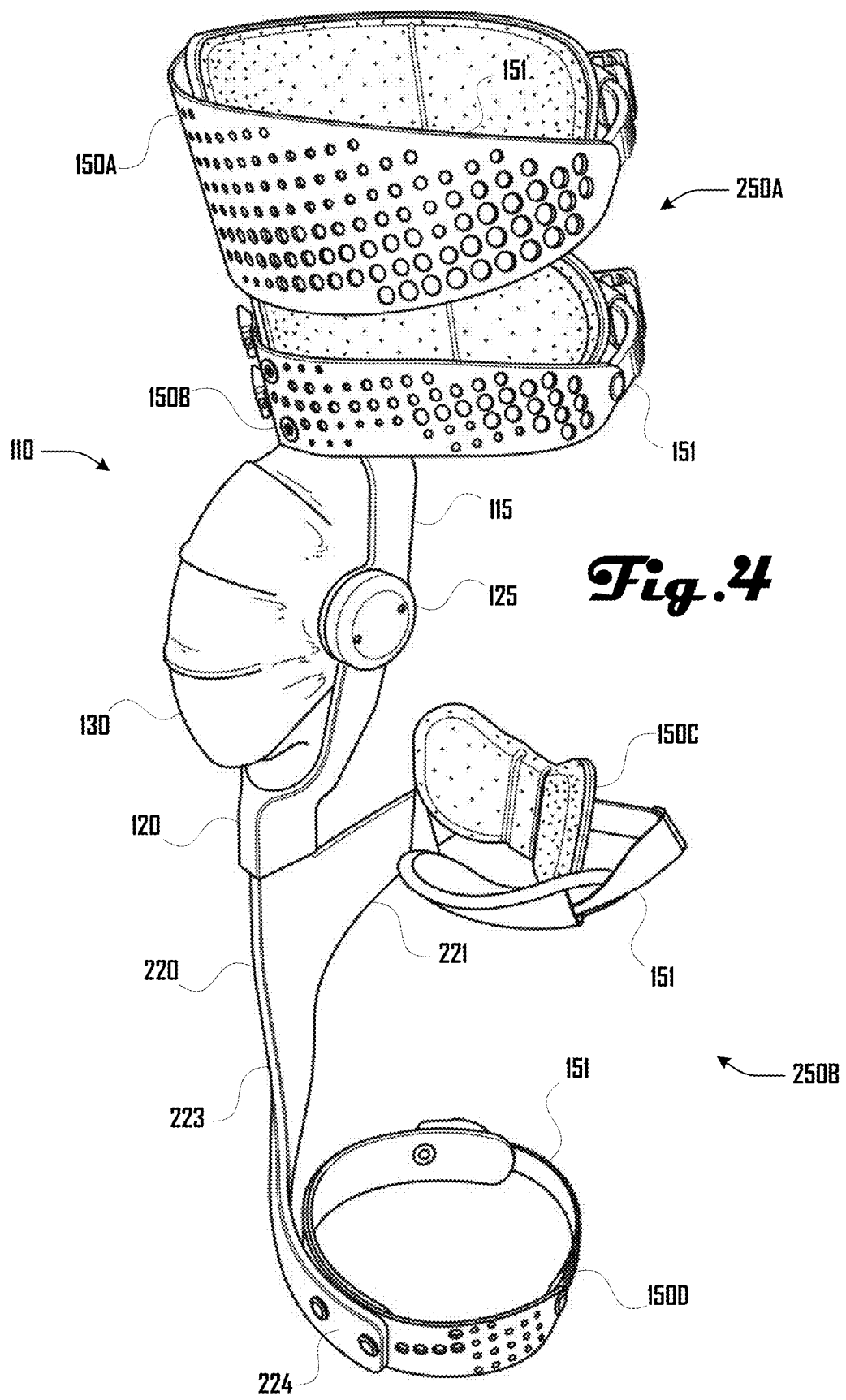
FIG. 4 is a perspective view of the leg actuation unit of FIGS. 3 and 4.

As discussed herein, an exoskeleton system 100 can be configured for various suitable uses. For example, FIGS. 1-3 illustrate an exoskeleton system 100 being used by a user. As shown in FIG. 1 the user 101 can wear the exoskeleton system 100 on both legs 102. FIGS. 2 and 3 illustrate a front and side view of an actuator unit 110 coupled to a leg 102 of a user 101 and FIG. 4 illustrates a side view of an actuator unit 110 not being worn by a user 101.

As shown in the example of FIG. 1, the exoskeleton system 100 can comprise a left and right leg actuator unit 110L, 110R that are respectively coupled to a left and right leg 102L, 102R of the user. In various embodiments, the left and right leg actuator units 110L, 110R can be substantially mirror images of each other.

As shown in FIGS. 1-4, leg actuator units 110 can include an upper arm 115 and a lower arm 120 that are rotatably coupled via a joint 125. A bellows actuator 130 extends between the upper arm 115 and lower arm 120. One or more sets of pneumatic lines 145 can be coupled to the bellows actuator 130 to introduce and/or remove fluid from the bellows actuator 130 to cause the bellows actuator 130 to expand and contract and to stiffen and soften, as discussed herein. A backpack 155 can be worn by the user 101 and can hold various components of the exoskeleton system 100 such as a fluid source, control system, a power source, and the like.

As shown in FIGS. 1-3, the leg actuator units 110L, 110R can be respectively coupled about the legs 102L, 102R of the user 101 with the joints 125 positioned at the knees 103L, 103R of the user 101 with the upper arms 115 of the leg actuator units 110L, 110R being coupled about the upper legs portions 104L, 104R of the user 101 via one or more couplers 150 (e.g., straps that surround the legs 102). The lower arms 120 of the leg actuator units 110L, 110R can be coupled about the lower leg portions 105L, 105R of the user 101 via one or more couplers 150.

The upper and lower arms 115, 120 of a leg actuator unit 110 can be coupled about the leg 102 of a user 101 in various suitable ways. For example, FIGS. 1-3 illustrates an example where the upper and lower arms 115, 120 and joint 125 of the leg actuator unit 110 are coupled along lateral faces (sides) of the top and bottom portions 104, 105 of the leg 102. As shown in the example of FIGS. 1-3, the upper arm 115 can be coupled to the upper leg portion 104 of a leg 102 above the knee 103 via two couplers 150 and the lower arm 120 can be coupled to the lower leg portion 105 of a leg 102 below the knee 103 via two couplers 150.

Specifically, upper arm 115 can be coupled to the upper leg portion 104 of the leg 102 above the knee 103 via a first set of couplers 250A that includes a first and second coupler 150A, 150B. The first and second couplers 150A, 150B can be joined by a rigid plate assembly 215 disposed on a lateral side of the upper leg portion 104 of the leg 102, with straps 151 of the first and second couplers 150A, 150B extending around the upper leg portion 104 of the leg 102. The upper arm 115 can be coupled to the plate assembly 215 on a lateral side of the upper leg portion 104 of the leg 102, which can transfer force generated by the upper arm 115 to the upper leg portion 104 of the leg 102.

The lower arm 120 can be coupled to the lower leg portion 105 of a leg 102 below the knee 103 via second set of couplers 250B that includes a third and fourth coupler 150C, 150D. A coupling branch unit 220 can extend from a distal end of, or be defined by a distal end of the lower arm 120. The coupling branch unit 220 can comprise a first branch 221 that extends from a lateral position on the lower leg portion 105 of the leg 102, curving upward and toward the anterior (front) of the lower leg portion 105 to a first attachment 222 on the anterior of the lower leg portion 105 below the knee 103, with the first attachment 222 joining the third coupler 150C and the first branch 221 of the coupling branch unit 220. The coupling branch unit 220 can comprise a second branch 223 that extends from a lateral position on the lower leg portion 105 of the leg 102, curving downward and toward the posterior (back) of the lower leg portion 105 to a second attachment 224 on the posterior of the lower leg portion 105 below the knee 103, with the second attachment 224 joining the fourth coupler 150D and the second branch 223 of the coupling branch unit 220.

As shown in the example of FIGS. 1-3, the fourth coupler 150D can be configured to surround and engage the boot 191 of a user. For example, the strap 151 of the fourth coupler 150D can be of a size that allows the fourth coupler 150D to surround the larger diameter of a boot 191 compared to the lower portion 105 of the leg 102 alone. Also, the length of the lower arm 120 and/or coupling branch unit 220 can be of a length sufficient for the fourth coupler 150D to be positioned over a boot 191 instead of being of a shorter length such that the fourth coupler 150D would surround a section of the lower portion 105 of the leg 102 above the boot 191 when the leg actuator unit 110 is worn by a user.

Attaching to the boot 191 can vary across various embodiments. In one embodiment, this attachment can be accomplished through a flexible strap that wraps around the circumference of boot 191 to affix the leg actuator unit 110 to the boot 191 with the desired amount of relative motion between the leg actuator unit 110 and the strap. Other embodiments can work to restrict various degrees of freedom while allowing the desired amount of relative motion between the leg actuator unit 110 and the boot 191 in other degrees of freedom. One such embodiment can include the use of a mechanical clip that connects to the back of the boot 191 that can provide a specific mechanical connection between the device and the boot 191. Various embodiments can include but are not limited to the designs listed previously, a mechanical bolted connection, a rigid strap, a magnetic connection, an electro-magnetic connection, an electromechanical connection, an insert into the user's boot, a rigid or flexible cable, or a connection directly to a boot.

Another aspect of the exoskeleton system 100 can be fit components used to secure the exoskeleton system 100 to the user 101. Since the function of the exoskeleton system 100 in various embodiments can rely heavily on the fit of the exoskeleton system 100 efficiently transmitting forces between the user 101 and the exoskeleton system 100 without the exoskeleton system 100 significantly drifting on the body 101 or creating discomfort, improving the fit of the exoskeleton system 100 and monitoring the fit of the exoskeleton system 100 to the user over time can be desirable for the overall function of the exoskeleton system 100 in some embodiments.

In various examples, different couplers 150 can be configured for different purposes, with some couplers 150 being primarily for the transmission of forces, with others being configured for secure attachment of the exoskeleton system 100 to the body 101. In one preferred embodiment for a single knee system, a coupler 150 that sits on the lower leg 105 of the user 101 (e.g., one or both of couplers 150C, 150D) can be intended to target body fit, and as a result, can remain flexible and compliant to conform to the body of the user 101. Alternatively, in this embodiment a coupler 150 that affixes to the front of the user's thigh on an upper portion 104 of the leg 102 (e.g., one or both of couplers 150A, 150B) can be intended to target power transmission needs and can have a stiffer attachment to the body than other couplers 150 (e.g., one or both of couplers 150C, 150D). Various embodiments can employ a variety of strapping or coupling configurations, and these embodiments can extend to include any variety of suitable straps, couplings, or the like, where two parallel sets of coupling configurations are meant to fill these different needs.

In some cases the design of the joint 125 can improve the fit of the exoskeleton system 100 on the user. In one embodiment, the joint 125 of a single knee leg actuator unit 110 can be designed to use a single pivot joint that has some deviations with the physiology of the knee joint. Another embodiment, uses a polycentric knee joint to better fit the motion of the human knee joint, which in some examples can be desirably paired with a very well fit leg actuator unit 110. Various embodiments of a joint 125 can include but are not limited to the example elements listed above, a ball and socket joint, a four bar linkage, and the like.

Some embodiments can include fit adjustments for anatomical variations in varus or valgus angles in the lower leg 105. One preferred embodiment includes an adjustment incorporated into a leg actuator unit 110 in the form of a cross strap that spans the joint of the knee 103 of the user 101, which can be tightened to provide a moment across the knee joint in the frontal plane which varies the nominal resting angle. Various embodiments can include but are not limited to the following: a strap that spans the joint 125 to vary the operating angle of the joint 125; a mechanical assembly including a screw that can be adjusted to vary the angle of the joint 125; mechanical inserts that can be added to the leg actuator unit 110 to discreetly change the default angle of the joint 125 for the user 101, and the like.

In various embodiments, the leg actuator unit 110 can be configured to remain suspended vertically on the leg 102 and remain appropriately positioned with the joint of the knee 103. In one embodiment, coupler 150 associated with a boot 191 (e.g., coupler 150D) can provide a vertical retention force for a leg actuator unit 110. Another embodiment uses a coupler 150 positioned on the lower leg 105 of the user 101 (e.g., one or both of couplers 150C, 150D) that exerts a vertical force on the leg actuator unit 110 by reacting on the calf of the user 101. Various embodiments can include but are not limited to the following: suspension forces transmitted through a coupler 150 on the boot (e.g., coupler 150D) or another embodiment of the boot attachment discussed previously; suspension forces transmitted through an electronic and/or fluidic cable assembly; suspension forces transmitted through a connection to a waist belt; suspension forces transmitted through a mechanical connection to a backpack 155 or other housing for the exoskeleton device 510 and/or pneumatic system 520 (see FIG. 5); suspension forces transmitted through straps or a harness to the shoulders of the user 101, and the like.

In various embodiments, a leg actuator unit 110 can be spaced apart from the leg 102 of the user with a limited number of attachments to the leg 102. For example, in some embodiments, the leg actuator unit 110 can consist or consist essentially of three attachments to the leg 102 of the user 101, namely via the first and second attachments 222, 224 and 215. In various embodiments, the couplings of the leg actuator unit 110 to the lower leg portion 105 can consist or consist essentially of a first and second attachment on the anterior and posterior of the lower leg portion 105. In various embodiments, the coupling of the leg actuator unit 110 to the upper leg portion 104 can consist or consist essentially of a single lateral coupling, which can be associated with one or more couplers 150 (e.g., two couplers 150A, 150B as shown in FIGS. 1-4). In various embodiments, such a configuration can be desirable based on the specific force-transfer for use during a subject activity. Accordingly, the number and positions of attachments or coupling to the leg 102 of the user 101 in various embodiments is not a simple design choice and can be specifically selected for one or more selected target user activities.

While specific embodiments of couplers 150 are illustrated herein, in further embodiments, such components discussed herein can be operably replaced by an alternative structure to produce the same functionality. For example, while straps, buckles, padding and the like are shown in various examples, further embodiments can include couplers 150 of various suitable types and with various suitable elements. For example, some embodiments can include Velcro hook-and-loop straps, or the like.

FIGS. 1-3 illustrate an example of an exoskeleton system 100 where the joint 125 is disposed laterally and adjacent to the knee 103 with a rotational axis of the joint 125 being disposed parallel to a rotational axis of the knee 103. In some embodiments, the rotational axis of the joint 125 can be coincident with the rotational axis of the knee 103. In some embodiments, a joint can be disposed on the anterior of the knee 103, posterior of the knee 103, inside of the knee 103, or the like.

In various embodiments, the joint structure 125 can constrain the bellows actuator 130 such that force created by actuator fluid pressure within the bellows actuator 130 can be directed about an instantaneous center (which may or may not be fixed in space). In some cases of a revolute or rotary joint, or a body sliding on a curved surface, this instantaneous center can coincide with the instantaneous center of rotation of the joint 125 or a curved surface. Forces created by a leg actuator unit 110 about a rotary joint 125 can be used to apply a moment about an instantaneous center as well as still be used to apply a directed force. In some cases of a prismatic or linear joint (e.g., a slide on a rail, or the like), the instantaneous center can be kinematically considered to be located at infinity, in which case the force directed about this infinite instantaneous center can be considered as a force directed along the axis of motion of the prismatic joint. In various embodiments, it can be sufficient for a rotary joint 125 to be constructed from a mechanical pivot mechanism. In such an embodiment, the joint 125 can have a fixed center of rotation that can be easy to define, and the bellows actuator 130 can move relative to the joint 125. In a further embodiment, it can be beneficial for the joint 125 to comprise a complex linkage that does not have a single fixed center of rotation. In yet another embodiment, the joint 125 can comprise a flexure design that does not have a fixed joint pivot. In still further embodiments, the joint 125 can comprise a structure, such as a human joint, robotic joint, or the like.

In various embodiments, leg actuator unit 110 (e.g., comprising bellows actuator 130, joint structure 125, and the like) can be integrated into a system to use the generated directed force of the leg actuator unit 110 to accomplish various tasks. In some examples, a leg actuator unit 110 can have one or more unique benefits when the leg actuator unit 110 is configured to assist the human body or is included into a powered exoskeleton system 100. In an example embodiment, the leg actuator unit 110 can be configured to assist the motion of a human user about the user's knee joint 103. To do so, in some examples, the instantaneous center of the leg actuator unit 110 can be designed to coincide or nearly coincide with the instantaneous center of rotation of the knee 103 of a user 101. In one example configuration, the leg actuator unit 110 can be positioned lateral to the knee joint 103 as shown in FIGS. 1-3. In various examples, the human knee joint 103 can function as (e.g., in addition to or in place of) the joint 125 of the leg actuator unit 110.

For clarity, example embodiments discussed herein should not be viewed as a limitation of the potential applications of the leg actuator unit 110 described within this disclosure. The leg actuator unit 110 can be used on other joints of the body including but not limited to one or more elbow, one or more hip, one or more finger, one or more ankle, spine, or neck. In some embodiments, the leg actuator unit 110 can be used in applications that are not on the human body such as in robotics, for general purpose actuation, animal exoskeletons, or the like.

Also, embodiments can be used for or adapted for various suitable applications such as tactical, medical, or labor applications, and the like. Examples of such applications can be found in U.S. patent application Ser. No. 15/823,523, filed Nov. 27, 2017 entitled "PNEUMATIC EXOMUSCLE SYSTEM AND METHOD" and U.S. patent application Ser. No. 15/953,296, filed Apr. 13, 2018 entitled "LEG EXOSKELETON SYSTEM AND METHOD", which are incorporated herein by reference.

Some embodiments can apply a configuration of a leg actuator unit 110 as described herein for linear actuation applications. In an example embodiment, the bellows actuator 130 can comprise a two-layer impermeable/inextensible construction, and one end of one or more constraining ribs can be fixed to the bellows actuator 130 at predetermined positions. The joint structure 125 in various embodiments can be configured as a series of slides on a pair of linear guide rails, where the remaining end of one or more constraining ribs is connected to a slide. The motion and force of the fluidic actuator can therefore be constrained and directed along the linear rail.

Figure 5:
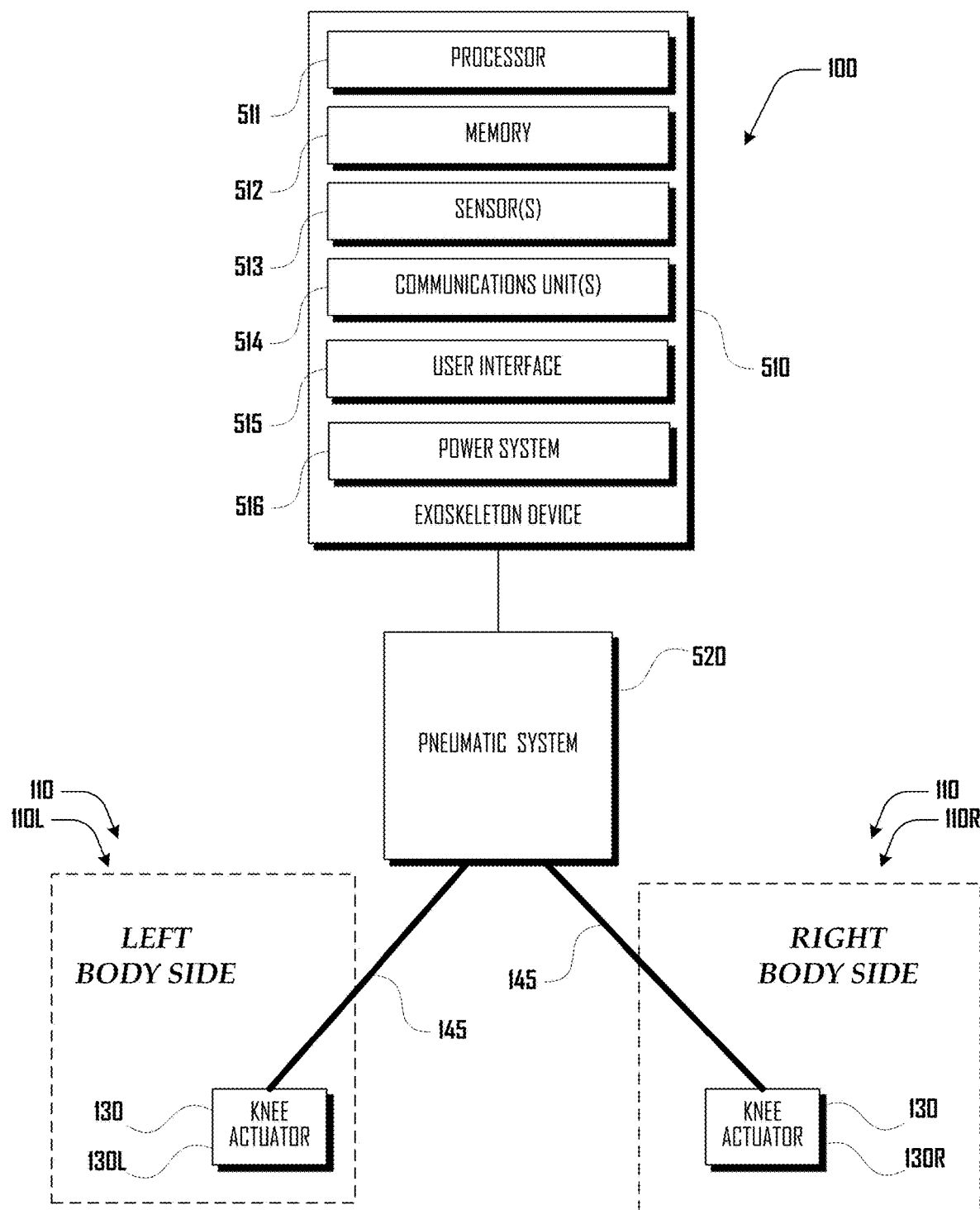
FIG. 5 is a block diagram illustrating an example embodiment of an exoskeleton system having a left and right leg actuator.

FIG. 5 is a block diagram of an example embodiment of an exoskeleton system 100 that includes an exoskeleton device 510 that is operably connected to a pneumatic system 520. While a pneumatic system 520 is used in the example of FIG. 5, further embodiments can include any suitable fluidic system or a pneumatic system 520 can be absent in some embodiments, such as where an exoskeleton system 100 is actuated by electric motors, or the like.

The exoskeleton device 510 in this example comprises a processor 511, a memory 512, one or more sensors 513 a communication unit 514, a user interface 515 and a power source 516. A plurality of actuators 130 are operably coupled to the pneumatic system 520 via respective pneumatic lines 145. The plurality of actuators 130 include a pair of knee-actuators 130L and 130R that are positioned on the right and left side of a body 100. For example, as discussed above, the example exoskeleton system 100 shown in FIG. 5 can comprise a left and right leg actuator unit 110L, 110R on respective sides of the body 101 as shown in FIGS. 1 and 2 with one or both of the exoskeleton device 510 and pneumatic system 520, or one or more components thereof, stored within or about a backpack 155 (see FIG. 1) or otherwise mounted, worn or held by a user 101.

Accordingly, in various embodiments, the exoskeleton system 100 can be a completely mobile and self-contained system that is configured to be powered and operate for an extended period of time without an external power source during various user activities. The size, weight and configuration of the actuator unit(s) 110, exoskeleton device 510 and pneumatic system 520 can therefore be configured in various embodiments for such mobile and self-contained operation.

In various embodiments, the example system 100 can be configured to move and/or enhance movement of the user 101 wearing the exoskeleton system 100. For example, the exoskeleton device 510 can provide instructions to the pneumatic system 520, which can selectively inflate and/or deflate the bellows actuators 130 via pneumatic lines 145. Such selective inflation and/or deflation of the bellows actuators 130 can move and/or support one or both legs 102 to generate and/or augment body motions such as walking, running, jumping, climbing, lifting, throwing, squatting, skiing or the like.

In some cases, the exoskeleton system 100 can be designed to support multiple configurations in a modular configuration. For example, one embodiment is a modular configuration that is designed to operate in either a single knee configuration or in a double knee configuration as a function of how many of the actuator units 110 are donned by the user 101. For example, the exoskeleton device 510 can determine how many actuator units 110 are coupled to the pneumatic system 520 and/or exoskeleton device 510 (e.g., on or two actuator units 110) and the exoskeleton device 510 can change operating capabilities based on the number of actuator units 110 detected.

In further embodiments, the pneumatic system 520 can be manually controlled, configured to apply a constant pressure, or operated in any other suitable manner. In some embodiments, such movements can be controlled and/or programmed by the user 101 that is wearing the exoskeleton system 100 or by another person. In some embodiments, the exoskeleton system 100 can be controlled by movement of the user 101. For example, the exoskeleton device 510 can sense that the user is walking and carrying a load and can provide a powered assist to the user via the actuators 130 to reduce the exertion associated with the load and walking. Similarly, where a user 101 wears the exoskeleton system 100, the exoskeleton system 100 can sense movements of the user 101 and can provide a powered assist to the user via the actuators 130 to enhance or provide an assist to the user while skiing.

Accordingly, in various embodiments, the exoskeleton system 130 can react automatically without direct user interaction. In further embodiments, movements can be controlled in real-time by user interface 515 such as a controller, joystick, voice control or thought control. Additionally, some movements can be pre-preprogrammed and selectively triggered (e.g., walk forward, sit, crouch) instead of being completely controlled. In some embodiments, movements can be controlled by generalized instructions (e.g. walk from point A to point B, pick up box from shelf A and move to shelf B).

The user interface 515 can allow the user 101 to control various aspects of the exoskeleton system 100 including powering the exoskeleton system 100 on and off; controlling movements of the exoskeleton system 100; configuring settings of the exoskeleton system 100, and the like. The user interface 515 can include various suitable input elements such as a touch screen, one or more buttons, audio input, and the like. The user interface 515 can be located in various suitable locations about the exoskeleton system 100. For example, in one embodiment, the user interface 515 can be disposed on a strap of a backpack 155, or the like. In some embodiments, the user interface can be defined by a user device such as smartphone, smart-watch, wearable device, or the like.

In various embodiments, the power source 516 can be a mobile power source that provides the operational power for the exoskeleton system 100. In one preferred embodiment, the power pack unit contains some or all of the pneumatic system 520 (e.g., a compressor) and/or power source (e.g., batteries) required for the continued operation of pneumatic actuation of the leg actuator units 110. The contents of such a power pack unit can be correlated to the specific actuation approach configured to be used in the specific embodiment. In some embodiments, the power pack unit will only contain batteries which can be the case in an electromechanically actuated system or a system where the pneumatic system 520 and power source 516 are separate. Various embodiments of a power pack unit can include but are not limited to a combination of the one or more of the following items: pneumatic compressor, batteries, stored high-pressure pneumatic chamber, hydraulic pump, pneumatic safety components, electric motor, electric motor drivers, microprocessor, and the like. Accordingly, various embodiments of a power pack unit can include one or more of elements of the exoskeleton device 510 and/or pneumatic system 520.

Such components can be configured on the body of a user 101 in a variety of suitable ways. One preferred embodiment is the inclusion of a power pack unit in a torso-worn pack that is not operably coupled to the leg actuator units 110 in any manner that transmits substantial mechanical forces to the leg actuator units 110. Another embodiment includes the integration of the power pack unit, or components thereof, into the leg actuator units 110 themselves. Various embodiments can include but are not limited to the following configurations: torso-mounted in a backpack, torso-mounted in a messenger bag, hip-mounted bag, mounted to the leg, integrated into the brace component, and the like. Further embodiments can separate the components of the power pack unit and disperse them into various configurations on the user 101. Such an embodiment may configure a pneumatic compressor on the torso of the user 101 and then integrate the batteries into the leg actuator units 110 of the exoskeleton system 100.

One aspect of the power supply 516 in various embodiments is that it must be connected to the brace component in such a manner as to pass the operable system power to the brace for operation. One preferred embodiment is the use of electrical cables to connect the power supply 516 and the leg actuator units 110. Other embodiments can use electrical cables and a pneumatic line 145 to deliver electrical power and pneumatic power to the leg actuator units 110. Various embodiments can include but are not limited to any configuration of the following connections: pneumatic hosing, hydraulic hosing, electrical cables, wireless communication, wireless power transfer, and the like.

In some embodiments, it can be desirable to include secondary features that extend the capabilities of a cable connection (e.g., pneumatic lines 145 and/or power lines) between the leg actuator units 110 and the power supply 516 and/or pneumatic system 520. One preferred embodiment includes retractable cables that are configured to have a small mechanical retention force to maintain cables that are pulled tight against the user with reduced slack remaining in the cable. Various embodiments can include, but are not limited to a combination of the following secondary features: retractable cables, a single cable including both fluidic and electrical power, magnetically-connected electrical cables, mechanical quick releases, breakaway connections designed to release at a specified pull force, integration into mechanical retention features on the user's clothing, and the like. Yet another embodiment can include routing the cables in such a way as to minimize geometric differences between the user 101 and the cable lengths. One such embodiment in a dual knee configuration with a torso power supply can be routing the cables along the user's lower torso to connect the right side of a power supply bag with the left knee of the user. Such a routing can allow the geometric differences in length throughout the user's normal range of motion.

One specific additional feature that can be a concern in some embodiments is the need for proper heat management of the exoskeleton system 100. As a result, there are a variety of features that can be integrated specifically for the benefit of controlling heat. One preferred embodiment integrates exposed heat sinks to the environment that allow elements of the exoskeleton device 510 and/or pneumatic system 520 to dispel heat directly to the environment through unforced cooling using ambient airflow. Another embodiment directs the ambient air through internal air channels in a backpack 155 or other housing to allow for internal cooling. Yet another embodiment can extend upon this capability by introducing scoops on a backpack 155 or other housing in an effort to allow air flow through the internal channels. Various embodiments can include but are not limited to the following: exposed heat sinks that are directly connected to a high heat component; a water-cooled or fluid-cooled heat management system; forced air cooling through the introduction of a powered fan or blower; external shielded heat sinks to protect them from direct contact by a user, and the like.

In some cases, it may be beneficial to integrate additional features into the structure of the backpack 155 or other housing to provide additional features to the exoskeleton system 100. One preferred embodiment is the integration of mechanical attachments to support storage of the leg actuator units 110 along with the exoskeleton device 510 and/or pneumatic system 520 in a small package. Such an embodiment can include a deployable pouch that can secure the leg actuator units 110 against the backpack 155 along with mechanical clasps that hold the upper or lower arms 115, 120 of the actuator units 110 to the backpack 155. Another embodiment is the inclusion of storage capacity into the backpack 155 so the user 101 can hold additional items such as a water bottle, food, personal electronics, and other personal items. Various embodiments can include but are not limited to other additional features such as the following: a warming pocket which is heated by hot airflow from the exoskeleton device 510 and/or pneumatic system 520; air scoops to encourage additional airflow internal to the backpack 155; strapping to provide a closer fit of the backpack 155 on the user, waterproof storage, temperature-regulated storage, and the like.

In a modular configuration, it may be required in some embodiments that the exoskeleton device 510 and/or pneumatic system 520 can be configured to support the power, fluidic, sensing and control requirements and capabilities of various potential configurations of the exoskeleton system. One preferred embodiment can include an exoskeleton device 510 and/or pneumatic system 520 that can be tasked with powering a dual knee configuration or a single knee configuration (i.e., with one or two leg actuator units 110 on the user 101). Such an exoskeleton system 100 can support the requirements of both configurations and then appropriately configure power, fluidic, sensing and control based on a determination or indication of a desired operating configuration. Various embodiments exist to support an array of potential modular system configurations, such as multiple batteries, and the like.

In various embodiments, the exoskeleton device 100 can be operable to perform methods or portions of methods described in more detail below or in related applications incorporated herein by reference. For example, the memory 512 can include non-transitory computer readable instructions (e.g., software), which if executed by the processor 511, can cause the exoskeleton system 100 to perform methods or portions of methods described herein or in related applications incorporated herein by reference.

This software can embody various methods that interpret signals from the sensors 513 or other sources to determine how to best operate the exoskeleton system 100 to provide the desired benefit to the user. The specific embodiments described below should not be used to imply a limit on the sensors 513 that can be applied to such an exoskeleton system 100 or the source of sensor data. While some example embodiments can require specific information to guide decisions, it does not create an explicit set of sensors 513 that an exoskeleton system 100 will require and further embodiments can include various suitable sets of sensors 513. Additionally, sensors 513 can be located at various suitable locations on an exoskeleton system 100 including as part of an exoskeleton device 510, pneumatic system 520, one or more fluidic actuator 130, or the like. Accordingly, the example illustration of FIG. 5 should not be construed to imply that sensors 513 are exclusively disposed at or part of an exoskeleton device 510 and such an illustration is merely provided for purposes of simplicity and clarity.

One aspect of control software can be the operational control of leg actuator units 110, exoskeleton device 510 and pneumatic system 520 to provide the desired response. There can be various suitable responsibilities of the operational control software. For example, as discussed in more detail below, one can be low-level control which can be responsible for developing baseline feedback for operation of the leg actuator units 110, exoskeleton device 510 and pneumatic system 520. Another can be intent recognition which can be responsible for identifying the intended maneuvers of the user 101 based on data from the sensors 513 and causing the exoskeleton system 100 to operate based on one or more identified intended maneuvers. A further example can include reference generation, which can include selecting the desired torques the exoskeleton system 100 should generate to best assist the user 101. It should be noted that this example architecture for delineating the responsibilities of the operational control software is merely for descriptive purposes and in no way limits the wide variety of software approaches that can be deployed on further embodiments of an exoskeleton system 100.

One method implemented by control software can be for the low-level control and communication of the exoskeleton system 100. This can be accomplished via a variety of methods as required by the specific joint and need of the user. In a preferred embodiment, the operational control is configured to provide a desired torque by the leg actuator unit 110 at the user's joint. In such a case, the exoskeleton system 100 can create low-level feedback to achieve a desired joint torque by the leg actuator units 110 as a function of feedback from the sensors 513 of the exoskeleton system 100. For example, such a method can include obtaining sensor data from one or more sensors 513, determining whether a change in torque by the leg actuator unit 110 is necessary, and if so, causing the pneumatic system 520 to change the fluid state of the leg actuator unit 110 to achieve a target joint torque by the leg actuator unit 110. Various embodiments can include, but are not limited to, the following: current feedback; recorded behavior playback; position-based feedback; velocity-based feedback; feedforward responses; volume feedback which controls a fluidic system 520 to inject a desired volume of fluid into an actuator 130, and the like.

Another method implemented by operational control software can be for intent recognition of the user's intended behaviors. This portion of the operational control software, in some embodiments, can indicate any array of allowable behaviors that the system 100 is configured to account for. In one preferred embodiment, the operational control software is configured to identify two specific states: Walking, and Not Walking. In such an embodiment, to complete intent recognition, the exoskeleton system 100 can use user input and/or sensor readings to identify when it is safe, desirable or appropriate to provide assistive actions for walking. For example, in some embodiments, intent recognition can be based on input received via the user interface 515, which can include an input for Walking, and Not Walking. Accordingly, in some examples, the use interface can be configured for a binary input consisting of Walking, and Not Walking.

In some embodiments, a method of intent recognition can include the exoskeleton device 510 obtaining data from the sensors 513 and determining, based at least in part of the obtained data, whether the data corresponds to a user state of Walking, and Not Walking. Where a change in state has been identified, the exoskeleton system 100 can be re-configured to operate in the current state. For example, the exoskeleton device 510 can determine that the user 101 is in a Not Walking state such as sitting and can configure the exoskeleton system 100 to operate in a Not Walking configuration. For example, such a Not Walking configuration can, compared to a Walking configuration, provide for a wider range of motion; provide no torque or minimal torque to the leg actuation units 110; save power and fluid by minimizing processing and fluidic operations; cause the system to be alert for supporting a wider variety of non-skiing motion, and the like.

The exoskeleton device 510 can monitor the activity of the user 101 and can determine that the user is walking or is about to walk (e.g., based on sensor data and/or user input), and can then configure the exoskeleton system 100 to operate in a Walking configuration. For example, such a Walking configuration, compared to a Not Walking configuration, can allow for a more limited range of motion that would be present during skiing (as opposed to motions during non-walking); provide for high or maximum performance by increasing the processing and fluidic response of the exoskeleton system 100 to support skiing; and the like. When the user 101 finishes a walking session, is identified as resting, or the like, the exoskeleton system 100 can determine that the user is no longer walking (e.g., based on sensor data and/or user input) and can then configure the exoskeleton system 100 to operate in the Not Walking configuration.

In some embodiments, there can be a plurality of Walking states, or Walking sub-states that can be determined by the exoskeleton system 100, including hard walking, moderate walking, light walking, downhill, uphill, jumping, recreational, sport, running, and the like (e.g., based on sensor data and/or user input). Such states can be based on the difficulty of the walking, ability of the user, terrain, weather conditions, elevation, angle of the walking surface, desired performance level, power-saving, and the like. Accordingly, in various embodiments, the exoskeleton system 100 can adapt for various specific types of walking or movement based on a wide variety of factors.

Another method implemented by operational control software can be the development of desired referenced behaviors for the specific joints providing assistance. This portion of the control software can tie together identified maneuvers with the level control. For example, when the exoskeleton system 100 identifies an intended user maneuver, the software can generate reference behaviors that define the torques, or positions desired by the actuators 130 in the leg actuation units 110. In one embodiment, the operational control software generates references to make the leg actuation units 110 simulate a mechanical spring at the knee 103 via the configuration actuator 130. The operational control software can generate torque references at the knee joints that are a linear function of the knee joint angle. In another embodiment, the operational control software generates a volume reference to provide a constant standard volume of air into a pneumatic actuator 130. This can allow the pneumatic actuator 130 to operate like a mechanical spring by maintaining the constant volume of air in the actuator 130 regardless of the knee angle, which can be identified through feedback from one or more sensors 513.

In another embodiment, a method implemented by the operational control software can include evaluating the balance of the user 101 while walking, moving, standing, or running and directing torque in such a way to encourage the user 101 to remain balanced by directing knee assistance to the leg 102 that is on the outside of the user's current balance profile. Accordingly, a method of operating an exoskeleton system 100 can include the exoskeleton device 510 obtaining sensor data from the sensors 510 indicating a balance profile of a user 101 based on the configuration of left and right leg actuation units 110L, 110R and/or environmental sensors such as position sensors, accelerometers, and the like. The method can further include determining a balance profile based on the obtained data, including an outside and inside leg, and then increasing torque to the actuation unit 110 associated with the leg 102 identified as the outside leg.

Various embodiments can use but are not limited to kinematic estimates of posture, joint kinetic profile estimates, as well as observed estimates of body pose. Various other embodiments exist for methods of coordinating two legs 102 to generate torques including but not limited to guiding torque to the most bent leg; guiding torque based on the mean amount of knee angle across both legs; scaling the torque as a function of speed or acceleration; and the like. It should also be noted that yet another embodiment can include a combination of various individual reference generation methods in a variety of matters which include but are not limited to a linear combination, a maneuver specific combination, or a non-linear combination.

In another embodiment, an operational control method can blend two primary reference generation techniques: one reference focused on static assistance and one reference focused on leading the user 101 into their upcoming behavior. In some examples, the user 101 can select how much predictive assistance is desired while using the exoskeleton system 100. For example, by a user 101 indicating a large amount of predictive assistance, the exoskeleton system 100 can be configured to be very responsive and may be well configured for a skilled operator on a challenging terrain. The user 101 could also indicate a desire for a very low amount of predictive assistance, which can result in slower system performance, which may be better tailored towards a learning user or less challenging terrain.

Various embodiments can incorporate user intent in a variety of manners and the example embodiments presented above should not be interpreted as limiting in any way. For example, method of determining and operating an exoskeleton system 100 can include systems and method of U.S. patent application Ser. No. 15/887,866, filed Feb. 2, 2018 entitled "SYSTEM AND METHOD FOR USER INTENT RECOGNITION," which is incorporated herein by reference. Also, various embodiments can use user intent in a variety of manners including as a continuous unit, or as a discrete setting with only a few indicated values.

At times it can be beneficial for operational control software to manipulate its control to account for a secondary or additional objective in order to maximize device performance or user experience. In one embodiment, the exoskeleton system 100 can provide an elevation-aware control over a central compressor or other components of a pneumatic system 520 to account for the changing density of air at different elevations. For example, operational control software can identify that the system is operating at a higher elevation based on data from sensors 513, or the like, and provide more current to the compressor in order to maintain electrical power consumed by the compressor. Accordingly, a method of operating a pneumatic exoskeleton system 100 can include obtaining data indicating air density where the pneumatic exoskeleton system 100 is operating (e.g., elevation data), determining optimal operating parameters of the pneumatic system 520 based on the obtained data, and configuring operation based on the determined optimal operating parameters. In further embodiments, operation of a pneumatic exoskeleton system 100 such as operating volumes can be tuned based on environmental temperature, which may affect air volumes.

In another embodiment, the exoskeleton system 100 can monitor the ambient audible noise levels and vary the control behavior of the exoskeleton system 100 to reduce the noise profile of the system. For example, when a user 101 is in a quiet public place or quietly enjoying a location alone or with others, noise associated with actuation of the leg actuation units 110 can be undesirable (e.g., noise of running a compressor or inflating or deflating actuators 130). Accordingly, in some embodiments, the sensors 513 can include a microphone that detects ambient noise levels and can configure the exoskeleton system 100 to operate in a quiet mode when ambient noise volume is below a certain threshold. Such a quiet mode can configure elements of a pneumatic system 520 or actuators 130 to operate more quietly, or can delay or reduce frequency of noise made by such elements.

In the case of a modular system, it can be desirable in various embodiments for operational control software to operate differently based on the number of leg actuation units 110 operational within the exoskeleton system 100. For example, in some embodiments, a modular dual-knee exoskeleton system 100 (see e.g., FIGS. 1 and 2) can also operate in a single knee configuration where only one of two leg actuation units 110 are being worn by a user 101 (see e.g., FIGS. 3 and 4) and the exoskeleton system 100 can generate references differently when in a two-leg configuration compared to a single leg configuration. Such an embodiment can use a coordinated control approach to generate references where the exoskeleton system 100 is using inputs from both leg actuation units 110 to determine the desired operation. However in a single-leg configuration, the available sensor information may have changed, so in various embodiments the exoskeleton system 100 can implement a different control method. In various embodiments this can be done to maximize the performance of the exoskeleton system 100 for the given configuration or account for differences in available sensor information based on there being one or two leg actuation units 110 operating in the exoskeleton system 100.

Accordingly, a method of operating an exoskeleton system 100 can include a startup sequence where a determination is made by the exoskeleton device 510 whether one or two leg actuation units 110 are operating in the exoskeleton system 100; determining a control method based on the number of actuation units 110 that are operating in the exoskeleton system 100; and implementing and operating the exoskeleton system 100 with the selected control method. A further method operating an exoskeleton system 100 can include monitoring by the exoskeleton device 510 of actuation units 110 that are operating in the exoskeleton system 100, determining a change in the number of actuation units 110 operating in the exoskeleton system 100, and then determining and changing the control method based on the new number of actuation units 110 that are operating in the exoskeleton system 100.

For example, the exoskeleton system 100 can be operating with two actuation units 110 and with a first control method. The user 101 can disengage one of the actuation units 110, and the exoskeleton device 510 can identify the loss of one of the actuation units 110 and the exoskeleton device 510 can determine and implement a new second control method to accommodate loss of one of the actuation units 110. In some examples, adapting to the number of active actuation units 110 can be beneficial where one of the actuation units 110 is damaged or disconnected during use and the exoskeleton system 100 is able to adapt automatically so the user 101 can still continue working or moving uninterrupted despite the exoskeleton system 100 only having a single active actuation unit 110.

In various embodiments, operational control software can adapt a control method where user needs are different between individual actuation units 110 or legs 102. In such an embodiment, it can be beneficial for the exoskeleton system 100 to change the torque references generated in each actuation unit 110 to tailor the experience for the user 101. One example is of a dual knee exoskeleton system 100 (see e.g., FIG. 1) where a user 101 has significant weakness issues in a single leg 102, but only minor weakness issues in the other leg 102. In this example, the exoskeleton system 100 can be configured to scale down the output torques on the less-affected limb compared to the more-affected limb to best meet the needs of the user 101.

Such a configuration based on differential limb strength can be done automatically by the exoskeleton system 100 and/or can be configured via a user interface 516, or the like. For example, in some embodiments, the user 101 can perform a calibration test while using the exoskeleton system 100, which can test relative strength or weakness in the legs 102 of the user 101 and configure the exoskeleton system 100 based on identified strength or weakness in the legs 102. Such a test can identify general strength or weakness of legs 102 or can identify strength or weakness of specific muscles or muscle groups such as the quadriceps, calves, hamstrings, gluteus, gastrocnemius; femoris, sartorius, soleus, and the like.

Another aspect of a method for operating an exoskeleton system 100 can include control software that monitors the exoskeleton system 100. A monitoring aspect of such software can, in some examples, focus on monitoring the state of the exoskeleton system 100 and the user 101 throughout normal operation in an effort to provide the exoskeleton system 100 with situational awareness and understanding of sensor information in order to drive user understanding and device performance. One aspect of such monitoring software can be to monitor the state of the exoskeleton system 100 in order to provide device understanding to achieve a desired performance capability. A portion of this can be the development of a system body pose estimate. In one embodiment, the exoskeleton device 510 uses the onboard sensors 513 to develop a real-time understanding of the user's pose. In other words, data from sensors 513 can be used to determine the configuration of the actuation units 110, which along with other sensor data can in turn be used to infer a user pose or body configuration estimate of the user 101 wearing the actuation units 110.

At times, and in some embodiments, it can be unrealistic or impossible for the exoskeleton system 100 to directly sense all important aspects of the system pose due to the sensing modalities not existing or their inability to be practically integrated into the hardware. As a result, the exoskeleton system 100 in some examples can rely on a fused understanding of the sensor information around an underlying model of the user's body and the exoskeleton system 100 the user is wearing. In one embodiment of a dual leg knee assistance exoskeleton system 100, the exoskeleton device 510 can use an underlying model of the user's lower extremity and torso body segments to enforce a relational constraint between the otherwise disconnected sensors 513. Such a model can allow the exoskeleton system 100 to understand the constrained motion of the two legs 102 in that they are mechanically connected through the user's kinematic chain created by the body. This approach can be used to ensure that the estimates for knee orientation are properly constrained and biomechanically valid. In various embodiments, the exoskeleton system 100 can include sensors 513 embedded in the exoskeleton device 510 and/or pneumatic system 520 to provide a fuller picture of the system posture. In yet another embodiment, the exoskeleton system 100 can include logical constraints that are unique to the application in an effort to provide additional constraints on the operation of the pose estimation. This can be desirable, in some embodiments, in conditions where ground truth information is unavailable such as highly dynamic actions, where the exoskeleton system 100 is denied an external GPS signal, or the earth's magnetic field is distorted.

In some embodiments, changes in configuration of the exoskeleton system 100 based location and/or location attributes can be performed automatically and/or with input from the user 101. For example, in some embodiments, the exoskeleton system 100 can provide one or more suggestions for a change in configuration based on location and/or location attributes and the user 101 can choose to accept such suggestions. In further embodiments, some or all configurations of the exoskeleton system 100 based location and/or location attributes can occur automatically without user interaction.

Various embodiments can include the collection and storage of data from the exoskeleton system 100 throughout operation. In one embodiment, this can include the live streaming of the data collected on the exoskeleton device 510 to a cloud storage location via the communication unit(s) 514 through an available wireless communication protocol or storage of such data on the memory 512 of the exoskeleton device 510, which may then be uploaded to another location via the communication unit(s) 514. For example, when the exoskeleton system 100 obtains a network connection, recorded data can be uploaded to the cloud at a communication rate that is supported by the available data connection. Various embodiments can include variations of this, but the use of monitoring software to collect and store data about the exoskeleton system 100 locally and/or remotely for retrieval at a later time for an exoskeleton system 100 such as this can be included in various embodiments.

In some embodiments, once such data has been recorded, it can be desirable to use the data for a variety of different applications. One such application can be the use of the data to develop further oversight functions on the exoskeleton system 100 in an effort to identify device system issues that are of note. One embodiment can be the use of the data to identify a specific exoskeleton system 100 or leg actuator unit 110 among a plurality, whose performance has varied significantly over a variety of uses. Another use of the data can be to provide it back to the user 101 to gain a better understanding of how they ski. One embodiment of this can be providing the data back to the user 101 through a mobile application that can allow the user 101 to review their use on a mobile device. Yet another use of such device data can be to synchronize playback of data with an external data stream to provide additional context. One embodiment is a system that incorporates the GPS data from a companion smartphone with the data stored natively on the device. Another embodiment can include the time synchronization of recorded video with the data stored that was obtained from the device 100. Various embodiments can use these methods for immediate use of data by the user to evaluate their own performance, for later retrieval by the user to understand behavior from the past, for users to compare with other users in-person or through an online profile, by developers to further the development of the system, and the like.

Another aspect of a method of operating an exoskeleton system 100 can include monitoring software configured for identifying user-specific traits. For example, the exoskeleton system 100 can provide an awareness of how a specific skier 101 operates in the exoskeleton system 100 and over time can develop a profile of the user's specific traits in an effort to maximize device performance for that user. One embodiment can include the exoskeleton system 100 identifying a user-specific use type in an effort to identify the use style or skill level of the specific user. Through an evaluation of the user form and stability during various actions (e.g., via analysis of data obtained from the sensors 513 or the like), the exoskeleton device 510 in some examples can identify if the user is highly skilled, novice, or beginner. This understanding of skill level or style can allow the exoskeleton system 100 to better tailor control references to the specific user.

In further embodiments, the exoskeleton system 100 can also use individualized information about a given user to build a profile of the user's biomechanic response to the exoskeleton system 100. One embodiment can include the exoskeleton system 100 collecting data regarding the user to develop an estimate of the individual user's knee strain in an effort to assist the user with understanding the burden the user has placed on his legs 102 throughout use. This can allow the exoskeleton system 100 to alert a user if the user has reached a historically significant amount of knee strain to alert the user that he may want to stop to spare himself potential pain or discomfort.

Another embodiment of individualized biomechanic response can be the system collecting data regarding the user to develop an individualized system model for the specific user. In such an embodiment the individualized model can be developed through a system ID (identification) method that evaluates the system performance with an underlying system model and can identify the best model parameters to fit the specific user. The system ID in such an embodiment can operate to estimate segment lengths and masses (e.g., of legs 102 or portions of the legs 102) to better define a dynamic user model. In another embodiment, these individualized model parameters can be used to deliver user specific control responses as a function of the user's specific masses and segment lengths. In some examples of a dynamic model, this can help significantly with the device's ability to account for dynamic forces during highly challenging activities.

In various embodiments, the exoskeleton system 100 can provide for various types of user interaction. For example, such interaction can include input from the user 101 as needed into the exoskeleton system 100 and the exoskeleton system 100 providing feedback to the user 101 to indicate changes in operation of the exoskeleton system 100, status of the exoskeleton system 100, and the like. As discussed herein, user input and/or output to the user can be provided via one or more user interface 515 of the exoskeleton device 510 or can include various other interfaces or devices such as a smartphone user device. Such one or more user interfaces 515 or devices can be located in various suitable locations such as on a backpack 155 (see e.g., FIG. 1), the pneumatic system 520, leg actuation units 110, or the like.

The exoskeleton system 100 can be configured to obtain intent from the user 101. For example, this can be accomplished through a variety of input devices that are either integrated directly with the other components of the exoskeleton system 100 (e.g., one or more user interface 515), or external and operably connected with the exoskeleton system 100 (e.g., a smartphone, wearable device, remote server, or the like). In one embodiment, a user interface 515 can comprise a button that is integrated directly into one or both of the leg actuation units 110 of the exoskeleton system 100. This single button can allow the user 101 to indicate a variety of inputs. In another embodiment, a user interface 515 can be configured to be provided through a torso-mounted lapel input device that is integrated with the exoskeleton device 510 and/or pneumatic system 520 of the exoskeleton system 100. In one example, such a user interface 515 can comprise a button that has a dedicated enable and disable functionality; a selection indicator dedicated to the user's desired power level (e.g., an amount or range of force applied by the leg actuator units 110); and a selector switch that can be dedicated to the amount of predictive intent to integrate into the control of the exoskeleton system 100. Such an embodiment of a user interface 515 can use a series of functionally locked buttons to provide the user 101 with a set of understood indicators that may be required for normal operation in some examples. Yet another embodiment can include a mobile device that is connected to the exoskeleton system 100 via a Bluetooth connection or other suitable wired or wireless connection. Use of a mobile device or smartphone as a user interface 515 can allow the user a far greater amount of input to the device due to the flexibility of the input method. Various embodiments can use the options listed above or combinations and variants thereof, but are in no way limited to the explicitly stated combinations of input methods and items.

The one or more user interface 515 can provide information to the user 101 to allow the user to appropriately use and operate the exoskeleton system 100. Such feedback can be in a variety of visual, haptic and/or audio methods including, but not limited to, feedback mechanisms integrated directly on one or both of the actuation units 110; feedback through operation of the actuation units 110; feedback through external items not integrated with the exoskeleton system 100 (e.g., a mobile device); and the like. Some embodiments can include integration of feedback lights in the actuation units 110, of the exoskeleton system 100. In one such embodiment, five multi-color lights are integrated into the knee joint 125 or other suitable location such that the user 101 can see the lights. These lights can be used to provide feedback of system errors, device power, successful operation of the device, and the like. In another embodiment, the exoskeleton system 100 can provide controlled feedback to the user to indicate specific pieces of information. In such embodiments, the exoskeleton system 100 can pulse the joint torque on one or both of the leg actuation units 110 to the maximum allowed torque when the user changes the maximum allowable user-desired torque, which can provide a haptic indicator of the torque settings. Another embodiment can use an external device such as a mobile device where the exoskeleton system 100 can provide alert notifications for device information such as operational errors, setting status, power status, and the like. Types of feedback can include, but are not limited to, lights, sounds, vibrations, notifications, and operational forces integrated in a variety of locations that the user 101 may be expected to interact with including the actuation units 110, pneumatic system 520, backpack 155, mobile devices, or other suitable methods of interactions such as a web interface, SMS text or email.

The communication unit 514 can include hardware and/or software that allows the exoskeleton system 100 to communicate with other devices, including a user device, a classification server, other exoskeleton systems 100, or the like, directly or via a network. For example, the exoskeleton system 100 can be configured to connect with a user device, which can be used to control the exoskeleton system 100, receive performance data from the exoskeleton system 100, facilitate updates to the exoskeleton system, and the like. Such communication can be wired and/or wireless communication.

In some embodiments, the sensors 513 can include any suitable type of sensor, and the sensors 513 can be located at a central location or can be distributed about the exoskeleton system 100. For example, in some embodiments, the exoskeleton system 100 can comprise a plurality of accelerometers, force sensors, position sensors, and the like, at various suitable positions, including at the arms 115, 120, joint 125, actuators 130 or any other location.

Accordingly, in some examples, sensor data can correspond to a physical state of one or more actuators 130, a physical state of a portion of the exoskeleton system 100, a physical state of the exoskeleton system 100 generally, and the like. In some embodiments, the exoskeleton system 100 can include a global positioning system (GPS), camera, range sensing system, environmental sensors, elevation sensor, microphone, thermometer, or the like. In some embodiments, the exoskeleton system 100 can obtain sensor data from a user device such as a smartphone, or the like.

In some cases, it can be beneficial for the exoskeleton system 100 to generate or augment an understanding of a user 101 wearing the exoskeleton device 100, of the environment and/or operation of the exoskeleton system 100 through integrating various suitable sensors 515 into the exoskeleton system 100. One embodiment can include sensors 515 to measure and track biological indicators to observe various suitable aspects of user 101 (e.g., corresponding to fatigue and/or body vital functions) such as, body temperature, heart rate, respiratory rate, blood pressure, blood oxygenation saturation, expired $CO_2$, blood glucose level, gait speed, sweat rate, and the like.

In some embodiments, the exoskeleton system 100 can take advantage of the relatively close and reliable connectivity of such sensors 515 to the body of the user 101 to record system vitals and store them in an accessible format (e.g., at the exoskeleton device, a remote device, a remote server, or the like). Another embodiment can include environmental sensors 515 that can continuously or periodically measure the environment around the exoskeleton system 100 for various environmental conditions such as temperature, humidity, light level, barometric pressure, radioactivity, sound level, toxins, contaminants, or the like. In some examples, various sensors 515 may not be required for operation of the exoskeleton system 100 or directly used by operational control software, but can be stored for reporting to the user 101 (e.g., via an interface 515) or sending to a remote device, a remote server, or the like.

The pneumatic system 520 can comprise any suitable device or system that is operable to inflate and/or deflate the actuators 130 individually or as a group. For example, in one embodiment, the pneumatic system can comprise a diaphragm compressor as disclosed in related patent application Ser. No. 14/577,817 filed Dec. 19, 2014 or a pneumatic power transmission as discussed herein.

Turning to FIGS. 6-10, another embodiment of an exoskeleton system 100 is illustrated. In this example embodiment, the exoskeleton system 100 includes a single right leg actuator unit 110; however, it should be clear that this example embodiment can be extended to an exoskeleton system 100 having both a left and right actuator unit 110L, 110R or only a left actuator unit 110L. Accordingly the example of FIGS. 6-10 should not be construed as limiting, and in further embodiments, any suitable elements can be present in a suitable plurality, absent, interchanged with elements of other embodiments (e.g., FIGS. 1-4), or the like.

As shown in FIGS. 6-10, the leg actuator unit 110 can include an upper arm 115 and a lower arm 120 that are rotatably coupled via a joint 125. A bellows actuator 130 extends between the upper arm 115 and lower arm 120. One or more sets of pneumatic lines 145 can be coupled to the bellows actuator 130 to introduce and/or remove fluid from the bellows actuator 130 to cause the bellows actuator 130 to expand and contract and to stiffen and soften, as discussed herein. The pneumatic lines 145 can comprise a line coupling 146 that can be engaged and disengaged to operably connect or disconnect the actuator unit 110 from the exoskeleton system 100. A backpack 155 can be worn by the user 101 (see FIGS. 6, 8 and 9) and can hold various components of the exoskeleton system 100 such as a fluid source, control system, a power source, exoskeleton device, pneumatic system, and the like as discussed herein.

As shown in FIGS. 6-9, the leg actuator unit 110 can be coupled about the right leg of the user 101 with the joint 125 positioned at the right knee 103R of the user 101 (see FIGS. 1-3 for labeling of body parts of the user 101), with the upper arm 115 of the leg actuator unit 110R being coupled about the right upper-leg portion 104R of the user 101 via one or more couplers 150 (e.g., straps that surround the legs 102). The lower arm 120 of the leg actuator unit 110 can be coupled about the right lower-leg portion 105R of the user 101 via one or more couplers 150.

The upper and lower arms 115, 120 of a leg actuator unit 110 can be coupled about the leg 102 of a user 101 in various suitable ways. For example, FIGS. 6-9 illustrate an example where the upper and lower arms 115, 120 and joint 125 of the leg actuator unit 110 are coupled along lateral faces (sides) of the top and bottom portions 104, 105 of the leg 102. As shown in the example of FIGS. 6-9, the upper arm 115 can be coupled to the upper-leg portion 104 of a leg 102 above the knee 103 via one coupler 150 and the lower arm 120 can be coupled to the lower-leg portion 105 of a leg 102 below the knee 103 via two couplers 150.

Specifically, upper arm 115 can be coupled to the upper-leg portion 104 of the leg 102 above the knee 103 via a first upper-leg coupler 150A. The first upper-leg coupler 150A can be associated with a rigid upper-leg brace 615 disposed on and engaging a lateral side of the upper-leg portion 104 of the leg 102, with a strap of the first upper-leg coupler 150A extending around the upper-leg portion 104 of the leg 102. The upper arm 115 can be coupled to the rigid upper-leg brace 615 on a lateral side of the upper-leg portion 104 of the leg 102, which can transfer force generated by the upper arm 115 to the upper-leg portion 104 of the leg 102.

The lower arm 120 can be coupled to the lower-leg portion 105 of a leg 102 below the knee 103 via a second set of couplers 650 that includes first and second lower-leg couplers 150C, 150D. The first and second lower-leg couplers 150C, 150D can be associated with a rigid lower-leg brace 620 disposed on and engaging a lateral side of the lower-leg portion 105 of the leg 102. The lower arm 120 can be coupled to the rigid lower-leg brace 620 on a lateral side of the lower-leg portion 105 of the leg 102, which can transfer force generated by the lower arm 120 to the lower-leg portion 105 of the leg 102. The rigid lower-leg brace 620 can extend downward from a coupling with the lower arm 120 at a lateral position on the lower-leg portion 105 of the leg 102, with a portion of the rigid lower-leg brace 620 curving toward the posterior (back) of the lower-leg portion 105 to attachments 622, 624 that couple one or more portions of the first and second lower-leg couplers 150C, 150D to the rigid lower-leg brace 620.

Figure 6:
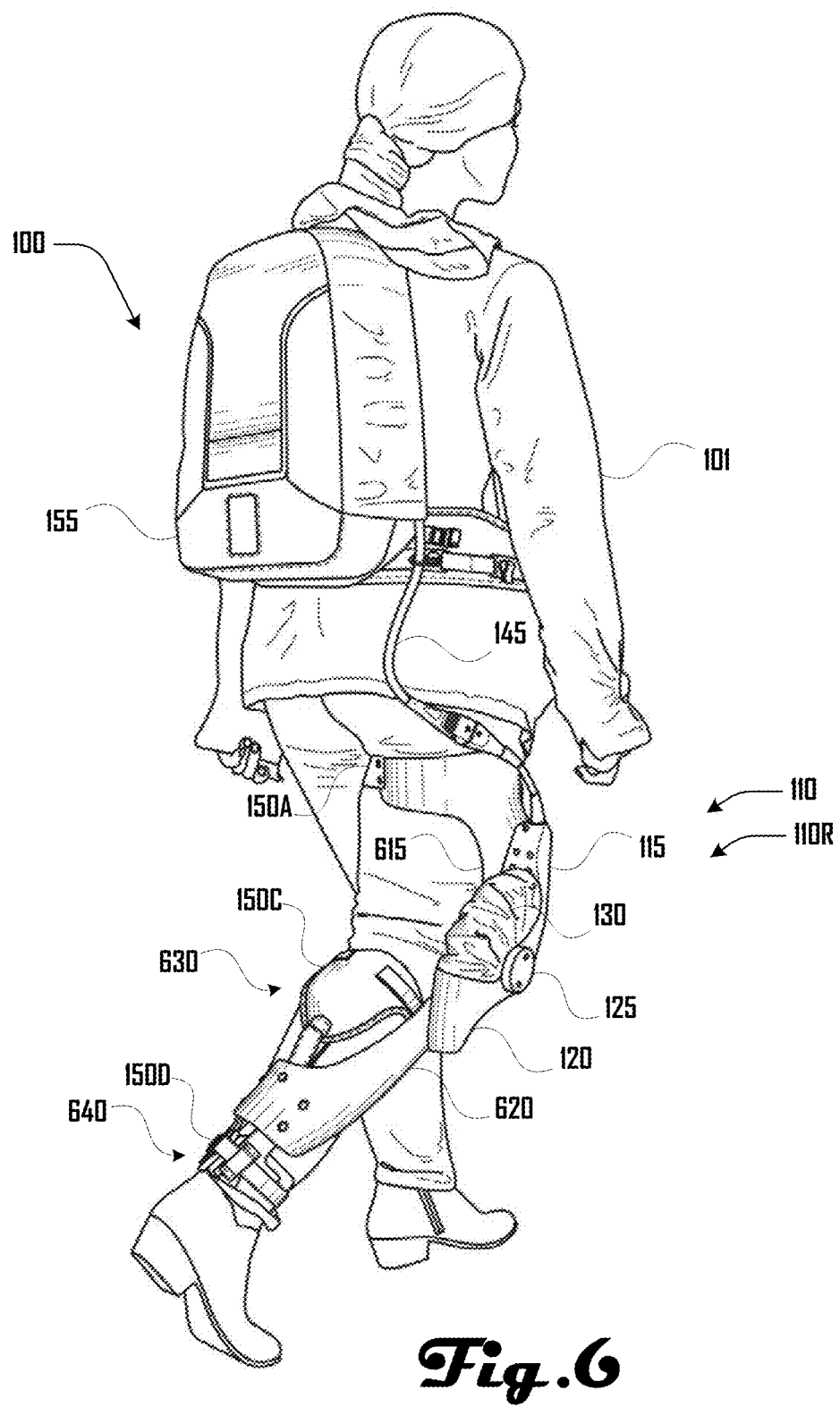
FIG. 6 is a rear view of another embodiment of an exoskeleton system including a leg actuator unit coupled to the right leg of a user.
Figure 7:
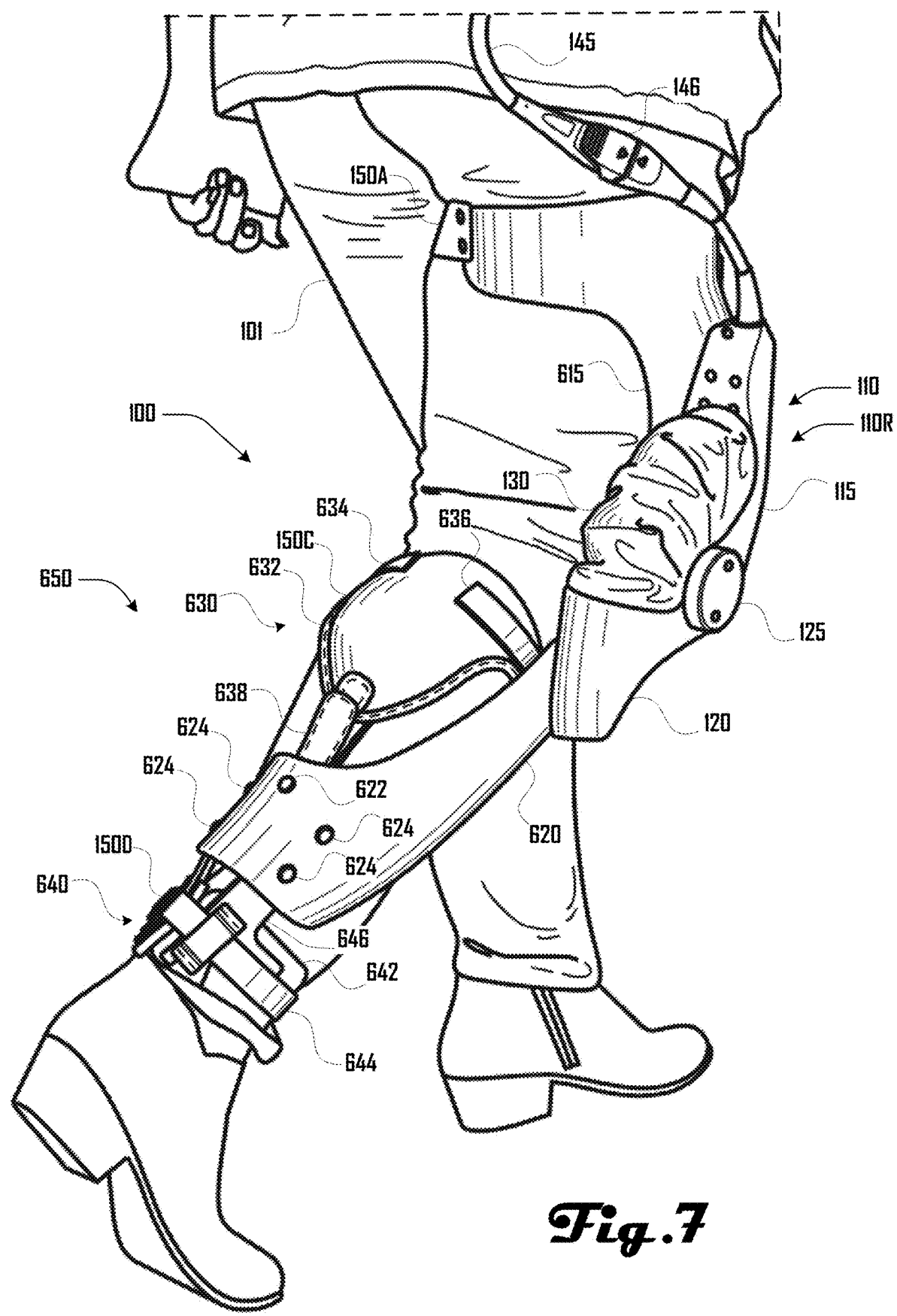
FIG. 7 is a close-up view of a portion of the illustration of FIG. 6.
Figure 8:
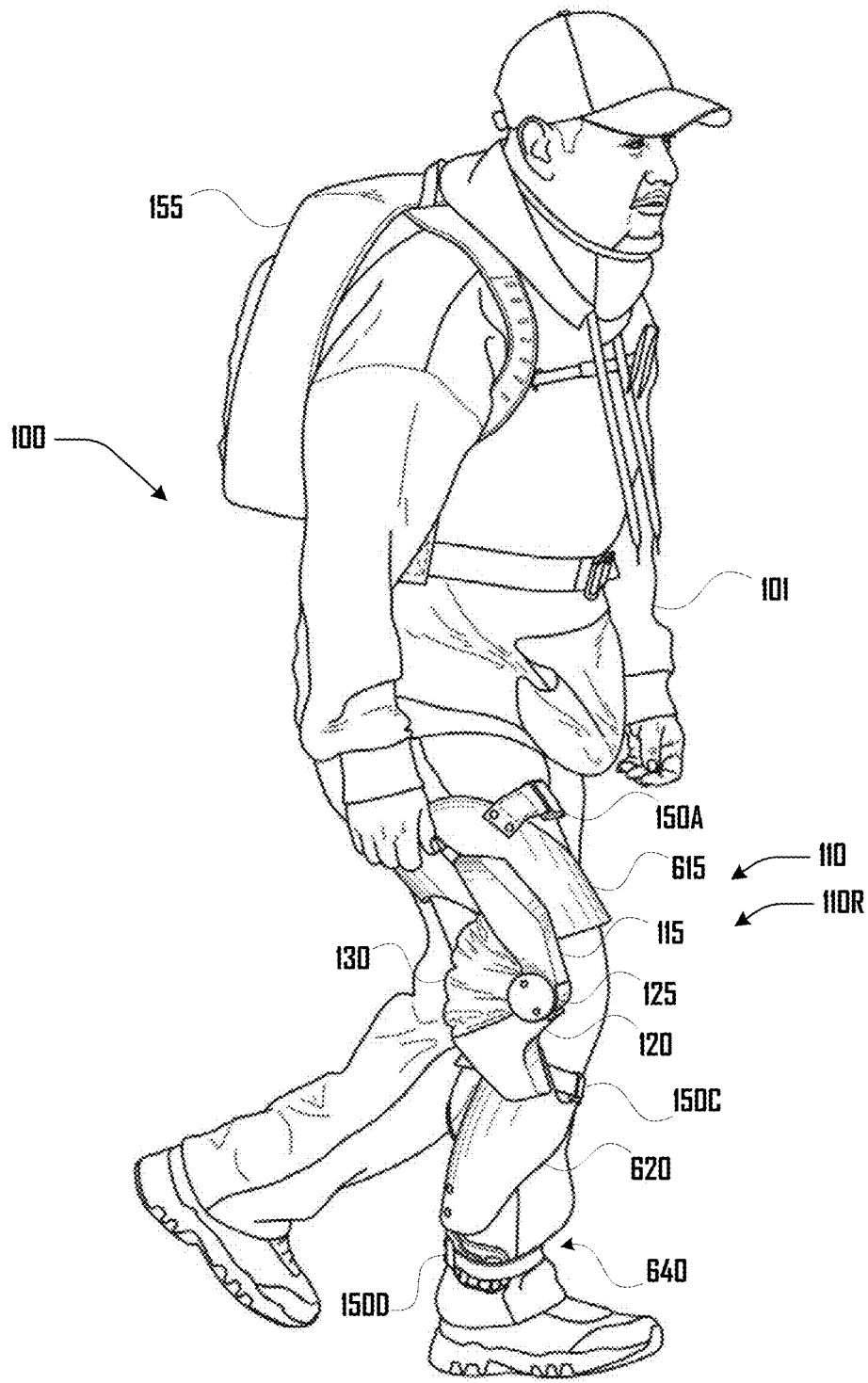
FIG. 8 is a side view of the embodiment of the exoskeleton system of FIGS. 6 and 7.
Figure 9:
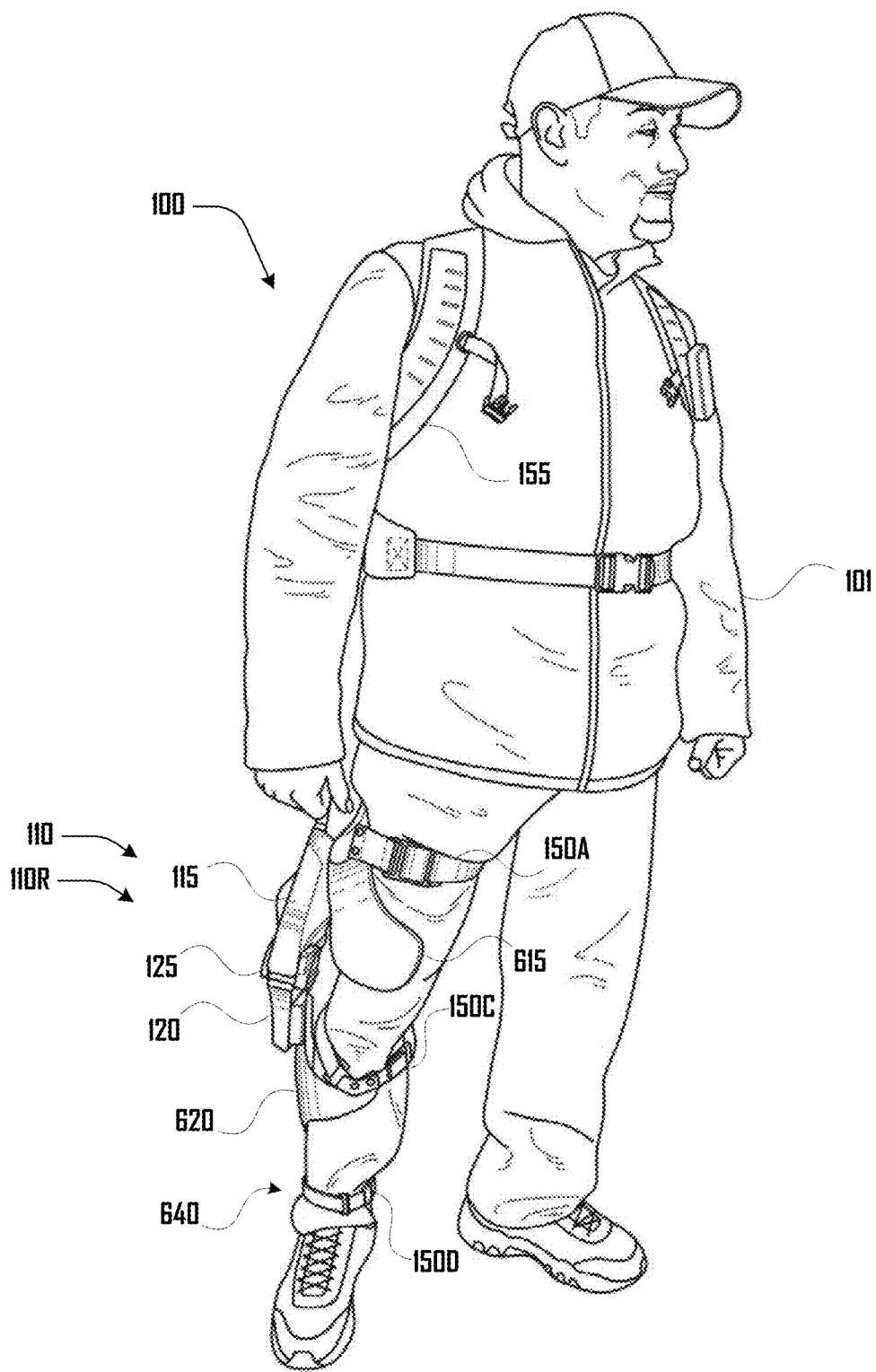
FIG. 9 is a front view of the exoskeleton system of FIGS. 6-8.
Figure 10:
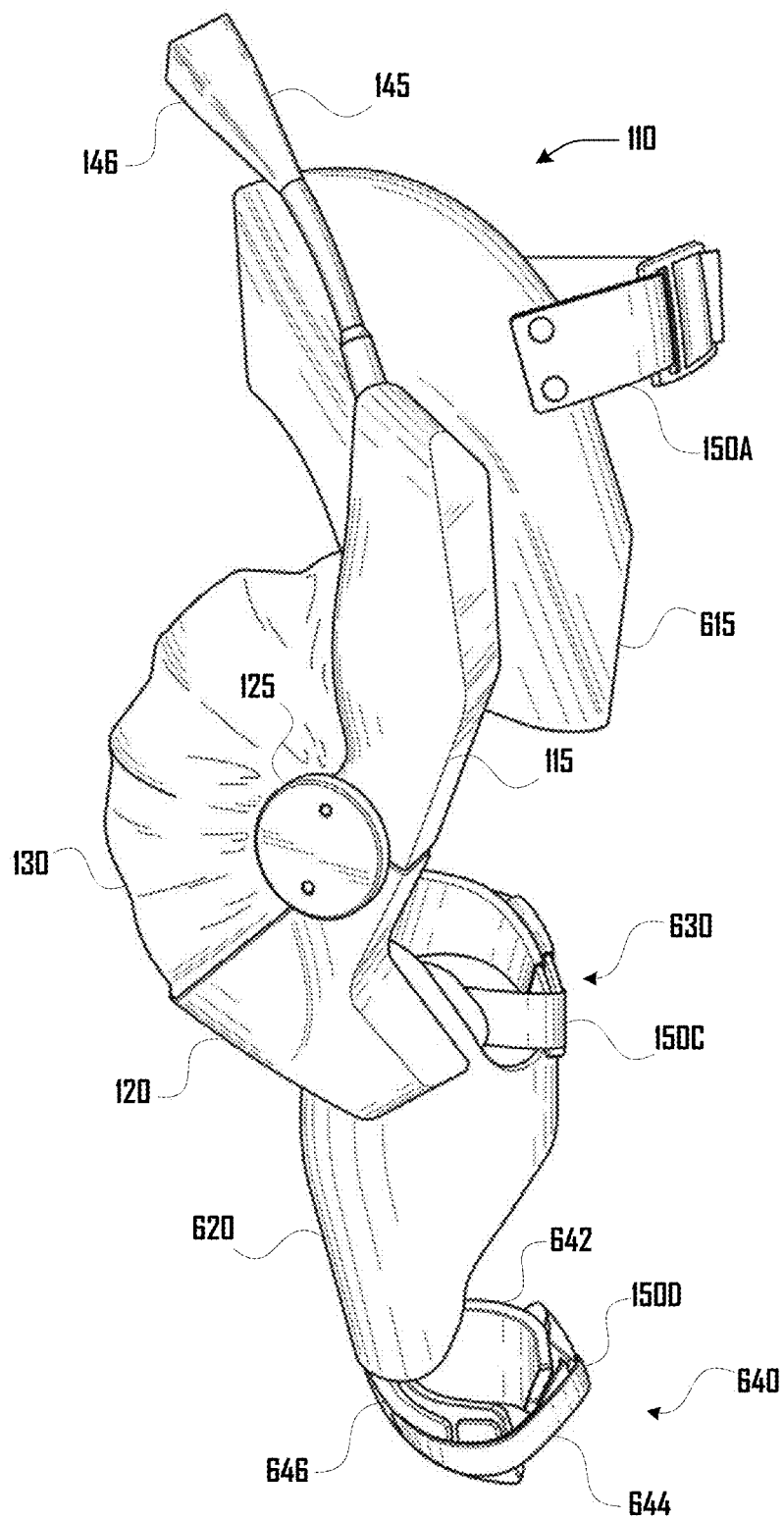
FIG. 10 is a perspective view of the leg actuation unit shown in FIGS. 6-9.

The first lower-leg coupler 150C can include a calf-coupling assembly 630 that includes a calf brace 632 that is coupled to the rigid lower-leg brace 620 via a first, second and third calf strap 634, 636, 638. For example, as shown in the example of FIGS. 6 and 7, the first and second calf straps 634, 636 can extend horizontally from opposing lateral sides of an upper portion of the rigid lower-leg brace 620 from an internal face of the rigid lower-leg brace 620. The third calf strap 638 can extend vertically from a lower posterior portion of the rigid lower-leg brace 620 from an internal face of the rigid lower-leg brace 620 where the third calf strap 638 is coupled to the rigid lower-leg brace 620 via a first set of one or more attachments 622. In various embodiments, the calf brace 632 can be a rigid or flexible element and can comprise materials such as a fabric, plastic, carbon-fiber, or the like.

The calf straps 634, 636, 638 can be configured in various suitable ways and can include various suitable mechanisms that allow the calf straps 634, 636, 638 to be tightened, loosened, extended, shortened, or the like. For example, in some embodiments, the first and second calf straps 634, 636 comprise hook and loop tape (e.g., Velcro) that allows the second calf straps 634, 636 to be tightened, loosened, extended, shortened, or the like. In some embodiments, the third calf strap 638 can comprise a strap cinch, or the like, that allows the third calf strap 638 to be tightened, loosened, extended, shortened, or the like.

The second lower-leg coupler 150D can comprise an ankle-coupling assembly 640 that includes a cuff 642 that extends around and surrounds the lower-leg portion 105 above the ankle of the user 101 and held via an ankle strap 644. The cuff 642 can be coupled to the rigid lower-leg brace 620 via one or more coupling tabs 646 that extend vertically from the cuff 642, with the one or more coupling tabs 646 coupled to the rigid lower-leg brace 620 via a second set of one or more attachments 624 on an internal face of the rigid lower-leg brace 620. The ankle strap 644 can include various suitable elements that allow the ankle strap to be tightened, loosened, extended, shortened, or the like (e.g., hook and loop tape, strap cinch, or the like).

In various embodiments, the rigid upper-leg and lower-leg braces 615, 620 can be made of various suitable materials such as a plastic, carbon-fiber, metal, wood, or the like. As discussed herein, in some embodiments the upper-leg and/or lower-leg braces 615, 620 can be formed to match the contours of the legs 102 of the user 101, which can be desirable for increasing comfort for the user 101 maximizing surface area of the upper-leg and/or lower-leg braces 615, 620 engaging the legs 102 of the user 101, and the like. In some examples, the upper-leg and/or lower-leg braces 615, 620 can be formed specifically for a given user 101, which can include molding to user body parts, scanning the user's body and generating upper-leg and/or lower-leg braces 615, 620 from such scan data, and the like.

Figure 11:
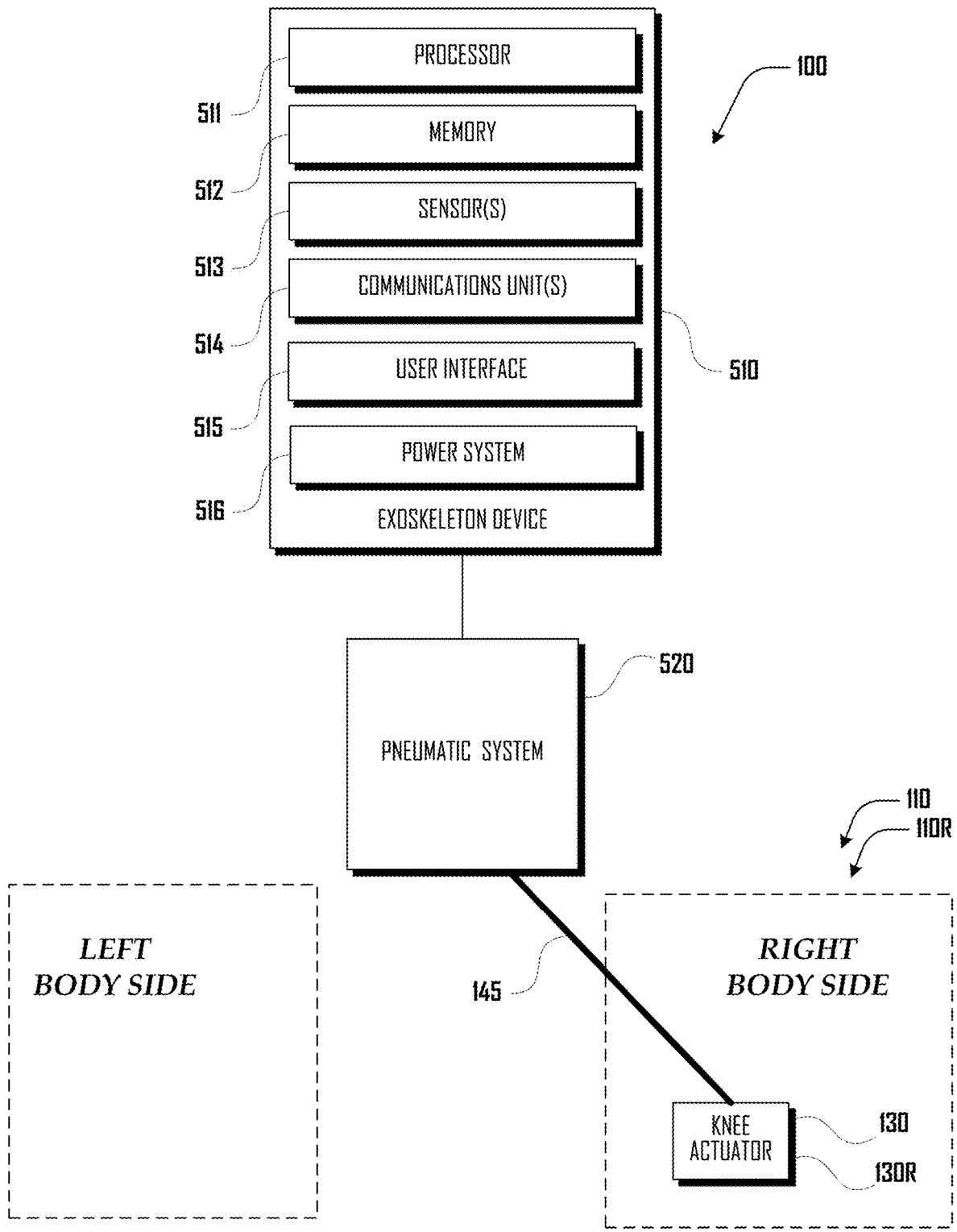
FIG. 11 is a block diagram illustrating an example embodiment of an exoskeleton system having a right leg actuator.
Figure 12:
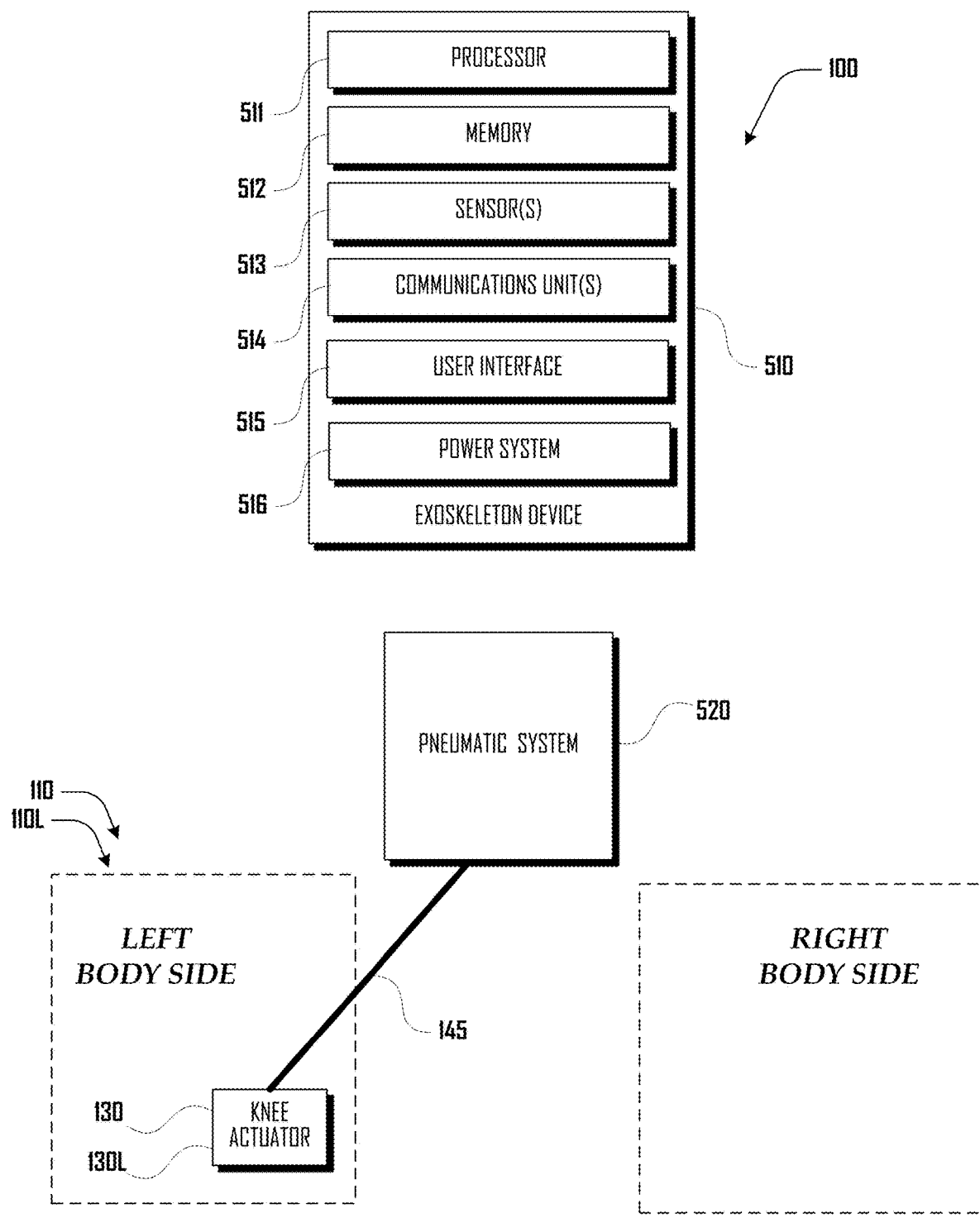
FIG. 12 is a block diagram illustrating an example embodiment of an exoskeleton system having a left leg actuator.

As discussed herein, various embodiments of an exoskeleton system 100 can be configured to operate modularly. For example, the exoskeleton system 100 can have a left and right leg actuator unit 110L, 110R and operate in a dual-leg configuration. However, in some embodiments, the left leg actuator unit 110L can be removed to generate a configuration as shown in FIG. 11 where the exoskeleton system 100 only includes a right actuator unit 110R and operates in a single-leg right configuration. Alternatively, the right leg actuator unit 110R can be removed to generate a configuration as shown in FIG. 12 where the exoskeleton system 100 only includes a left actuator unit 110L and operates in a single-leg left configuration. In various embodiments, an exoskeleton system 100 operating in a single-leg configuration such as shown in FIGS. 11 and 12, can then have a leg actuation unit coupled to the exoskeleton system 100 on the opposing body side leg such that the exoskeleton system 100 operates in a dual-leg configuration as shown in FIG. 5.

In the example case of a modular exoskeleton system 100 where one or more leg actuation units 110 can be coupled to and actuated by the exoskeleton system 100, it can be desirable in some embodiments for operational control software executed by an exoskeleton device 510 to operate based on a determination of a number and identity of one or more actuation units 110 coupled with and operational within the exoskeleton system 100. In one embodiment of a modular dual-knee exoskeleton system 100 that can also operate in a single knee configuration (e.g., a system that can operate with one or both of a left and right leg actuation unit 110L, 110R), operational control software executed by an exoskeleton device 510 can generate references for the exoskeleton system 100 differently when in a two-leg configuration and when in a single-leg configuration. Specifically, such an embodiment may use a coordinated control approach to generate references where the exoskeleton system 100 is using inputs from both legs to determine the desired operation; however, in a single-leg configuration, the available sensor information can change (e.g., sensors 513 associated with and/or disposed on a second actuation unit 110 may be absent or disabled) so the exoskeleton system 100 can implement a different strategy based on the available sensor data. In various embodiments, this can be done to maximize the performance of the exoskeleton system 100 for the given configuration or to account for variations in available sensor information.

Figure 13:
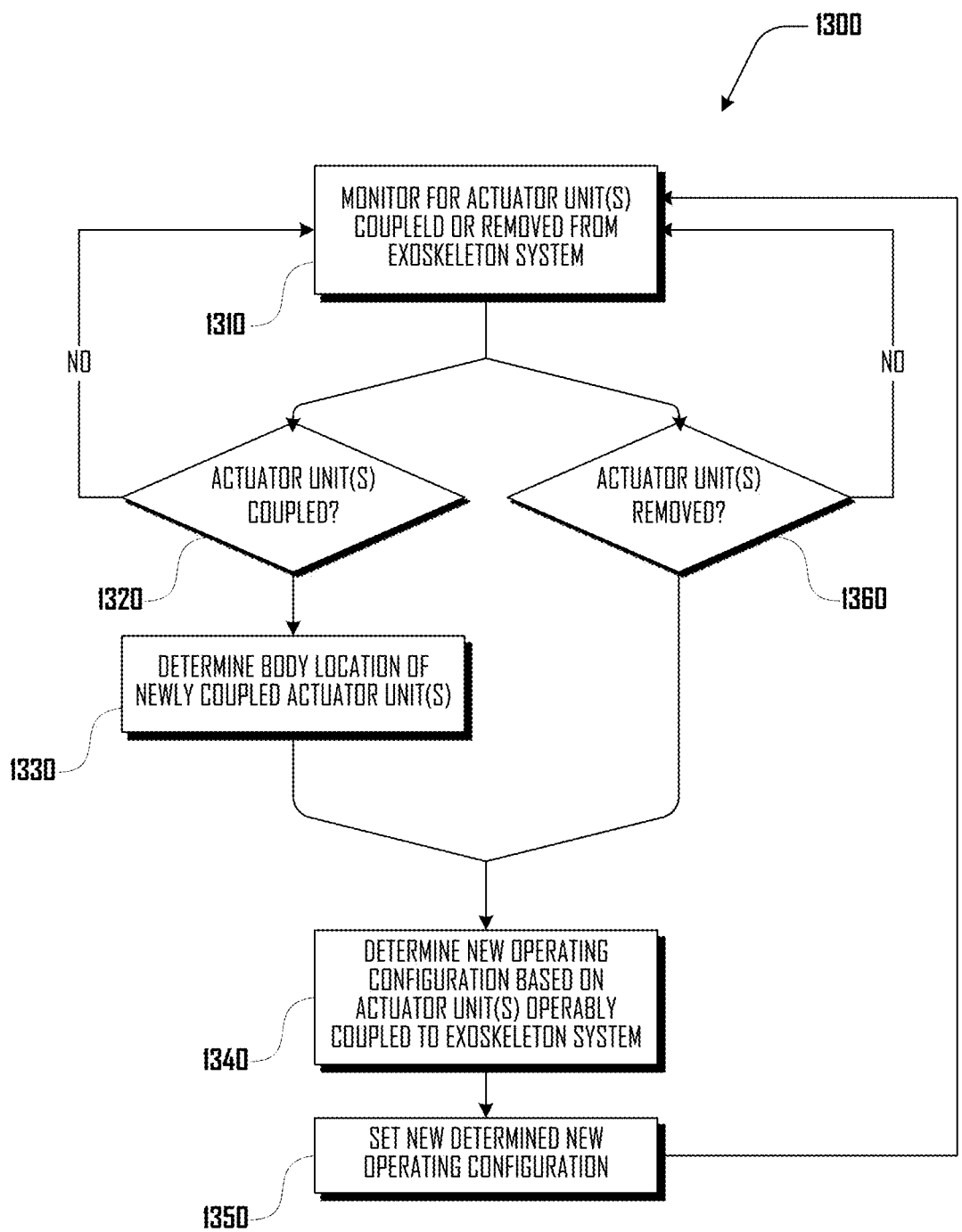
FIG. 13 illustrates an example method of operating a modular exoskeleton system in accordance with one embodiment.

Turning to FIG. 13, one example method 1300 of operating a modular exoskeleton system 100 is illustrated. The method 1300 begins at 1310 where an exoskeleton device 510 monitors for actuator units 110 being coupled to or removed from the modular exoskeleton system 100. For example, as discussed herein, in various embodiments one or more actuator units 110 can be operably coupled to an exoskeleton system 100 via one or more lines 145, which can include fluidic lines, communication lines, sensor lines, power lines, and the like. The exoskeleton device 510, in some embodiments, can determine whether one or more actuator units 110 are operably coupled to the exoskeleton system 100 based on data, information, or a status associated with such lines, based on user input, wireless communication (e.g., Bluetooth, NFC, RFID), or the like. In some embodiments, the exoskeleton device 510 can determine whether one or more actuator units 110 are operably coupled to the exoskeleton system 100 based on data, information or a status communicated wirelessly (e.g., through Bluetooth, ANT, RFID, a wireless network, etc.) between the actuator unit 110 and the exoskeleton system 100. Accordingly, it should be clear that various embodiments of an exoskeleton system 100 can have any suitable physical, wired and/or wireless operable coupling between one or more actuator units 110 and an exoskeleton device 510, with some embodiments including no physical or wired operable couplings between an actuator unit 110 and an exoskeleton device 510, with the actuator unit 110 being controlled wirelessly and having an independent power source and fluid source that does not require a physical coupling to an exoskeleton device 510.

In some examples, a line coupling 146 (see FIG. 7) being coupled or de-coupled can be used to determine whether a given actuator unit 110 is operably coupled to the exoskeleton system 100 (e.g., via a switch, or detection of an operable coupling generated by a connection of a line coupling 146 such as an operable coupling of fluidic lines, communication lines, sensor lines, power lines, and the like).

Returning to the example method 1300 of operating a modular exoskeleton system 100 of FIG. 13, at 1320, the exoskeleton device 510 can determine that one or more new actuator unit 110 has been coupled with the exoskeleton system 100, and at 1330, the exoskeleton device 510 can determine a location where the new actuator unit 110 is coupled on the body of the user 101. In some examples, the exoskeleton device 510 can be configured to determine an identity of an actuator unit 110 such as a serial number, MAC address, model number, or the like, based on a operable connection with the actuator unit 110, user input, or the like.

In some examples, the exoskeleton device 510 can be configured to determine a location where a given actuator unit 110 is coupled on the body of a user (e.g., left leg, right leg, left arm, right arm, torso, neck, and the like), based on a determined identity of the actuator unit 110, based on a coupling slot that the actuator unit 110 is plugged into (e.g., a left-leg or right-leg line coupling 146), based on user selection, based on wireless communication between the exoskeleton device 510 and the actuator unit 110, or the like. For example, an identifier obtained by the exoskeleton device 510 corresponding to a left leg actuator unit 110L can be associated with information that indicates that the left leg actuator unit 110L is specifically configured for being coupled to the left leg 102L of the user 101 and/or not the right leg 102L of the user 101. Such an identifier can be used to determine, at least implicitly, that the left leg actuator unit 110L is coupled to the left leg 102L of the user 101 and/or that the left leg actuator unit 110L is not coupled to the right leg 102L of the user 101 or not coupled to another body portion or joint such as an arm, elbow, wrist, shoulder, or the like. Additionally, it should be clear that a determination that an actuation unit 110 is coupled to a given limb, body joint, or the like, may include an implicit determination of such a coupling and that such a determination may not actually include a determination or confirmation of a suitable physical coupling to a given limb of a user.

Also, while some examples illustrated herein show one or more actuator units 110 that consist of a single actuator 130, further embodiments can include actuator units 110 that comprise a plurality actuators and determining the identity and/or locations of an actuator unit 110 can include determining a number of actuators 130 associated with a given actuator unit 110 and the location of such actuator units 110 and/or their associated actuators 130 on the body of a user 101. For example, in some embodiments, the identity of an actuator unit 110 can be associated with the number of actuators 130 of the actuator unit 110, the location of one or more actuators 130, body joint(s) and/or location(s) that such actuators are associated with, a kinematic model of an actuator unit 110, or the like.

Returning to the example method 1300 of operating a modular exoskeleton system 100, the exoskeleton device 510, at 1340, can determine a new operating configuration, and at 1350, can set the new operating configuration based on a current set of actuator units 110 coupled to the exoskeleton system 100. For example, where a determination is made that a right and left leg actuator 110R, 110L with actuators 130R, 130L on respective knees 103R, 103L are coupled to the exoskeleton system 100 (e.g., as shown in FIG. 5), the exoskeleton device 510 can determine and set a dual-knee operating configuration.

However, if a determination is made that only a right leg actuator 110R, with only an actuator 130R associated with the right knee 103R, is coupled to the exoskeleton system 100 (e.g., as shown in FIG. 11), the exoskeleton device 510 can determine and set a single-right-knee operating configuration. However, if a determination is made that only a left leg actuator 110L, with only an actuator 130L associated with the left knee 103L, is coupled to the exoskeleton system 100 (e.g., as shown in FIG. 12), the exoskeleton device 510 can determine and set a single-left-knee operating configuration.

Returning to the example method 1300 of operating a modular exoskeleton system 100, at 1360, the exoskeleton device 510 can determine that an actuator unit 110 has been removed from the exoskeleton system 100 and the exoskeleton device 510 can then determine and set an operating configuration at 1340 and 1350. For example, if an exoskeleton is operating in a dual-knee operating configuration with a left and right leg actuator 110L, 110R (e.g., as shown in FIG. 5) and then the left leg actuator 110L is removed (e.g., generating the configuration of FIG. 11), the exoskeleton device 510 can identify the removal of the left leg actuator 110L and switch to operating in a single-right-knee operating configuration. It should be made clear that the removal of an actuator unit 110 can be caused by, but is not limited to, a physical disconnection from the exoskeleton system 100 through a disconnection of a line coupling 146 or a wireless connection between the actuator unit 110 and the exoskeleton system 100, a removal by user selection, a malfunction of an actuator unit 110 rendering it inoperable or partially inoperable, and the like.

In various embodiments, determining and setting an operating configuration after removal of one or more actuation unit 110 can be done in various suitable ways, including determine the identity of actuator units 110 (if any) coupled to the exoskeleton system 100; determining a new configuration by identifying one or more actuation units 110 that have been removed and modifying a current configuration to a new configuration based on the identity the one or more removed actuator unit 110; or the like. Also, in some embodiments, a determination can be made that no actuation units 110 are operably coupled to the exoskeleton system 100 or that a set or a partial set of actuation units 110 operably coupled to the exoskeleton system 100 is a set or a partial set that is not allowed or not a set or a partial set of actuation units 110 that there is a suitable operating configuration for. For example, if a user accidently couples two left leg actuator units 110L to the exoskeleton system 100, the exoskeleton system 100 can identity this set of left leg actuator units 110L as being not allowed or not a set of actuation units 110 that there is a suitable operating configuration for, and an error message can be presented via a user interface 515 or only one of the left leg actuator units 110L can be determined as coupled to the device 510 leading to a single left-knee-operating configuration, or the like.

While various examples herein relate to embodiments that can include one or two leg actuator units 110L, 110R with actuators 130L, 130R at the knees 103L, 103R, it should be clear that the methods discuss herein can be used in embodiments with any suitable plurality of actuator units 110 on any suitable portion of the body with one or more actuators 130 configured to actuate any suitable body joint of a user as discussed herein. For example, one example can include a modular system with four actuator units 110 configured to actuate the knees and elbows of a user 101 with each of the four actuator units 110 having a single actuator 130 configured to actuate a respective joint of the user 101. Accordingly, the example embodiments herein should not be construed as being limiting.

Another novel consideration in some examples of operational control software is if the user's needs are different between individual joints or legs. In such a scenario, it may be beneficial for the exoskeleton system 100 to change the torque references generated for each leg actuator unit 110L, 110R to tailor the experience for the user. One example embodiment is that of a dual-knee exoskeleton configuration where a user has significant pain issues in a single leg, but not in the other leg. In such a case, the exoskeleton system 100 can include the ability for the exoskeleton system 100 to scale the output torques on the unaffected limb to best meet the needs of the user. In some examples, determining an operating configuration in a modular exoskeleton system 100 can include determining a set of one or more actuator units 110 operably coupled to the exoskeleton system 100 and determining settings of the one or more actuation units 110 based on the location of the actuators and different user needs between one or more individual body joints of the user 101.

Accordingly, in some embodiments, generating references can be based on differential needs of different legs of a user, which in some examples can include generating references for a left and right actuator unit 110L, 110R and scaling the references for one of the legs. For example, where a user has a weak left leg 102L and a fully capable right leg 102R, the exoskeleton system 100 can generate references for a left and right actuator unit 110L, 110R (e.g., via one or both of methods 1100, 1101), and can reduce the references for the right leg actuator unit 110R by 50% so that the weaker left leg 102L receives 100% references and the stronger right leg 102R receive reduced 50% references.

Figure 14A:
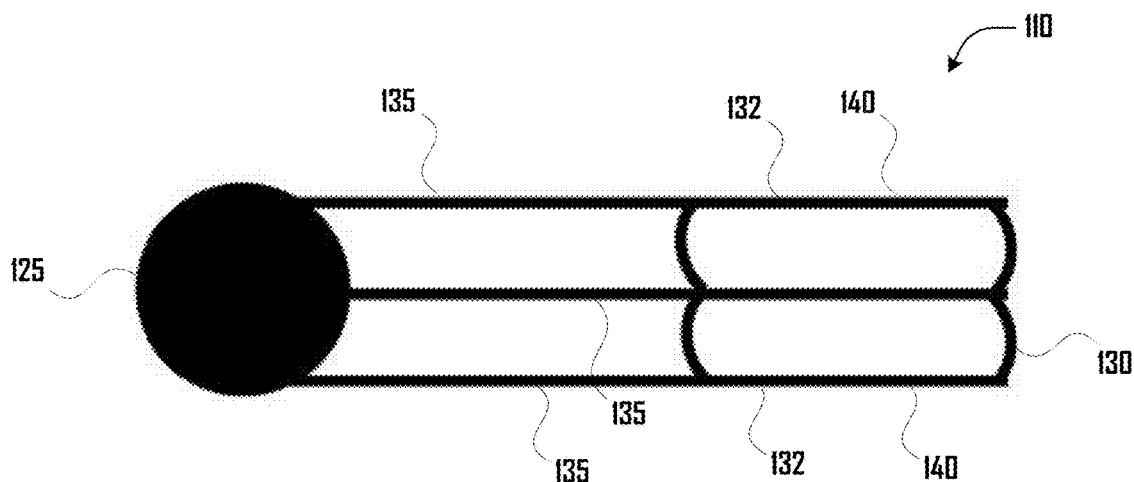
FIG. 14a illustrates a side view of a pneumatic actuator in a compressed configuration in accordance with one embodiment.
Figure 14B:
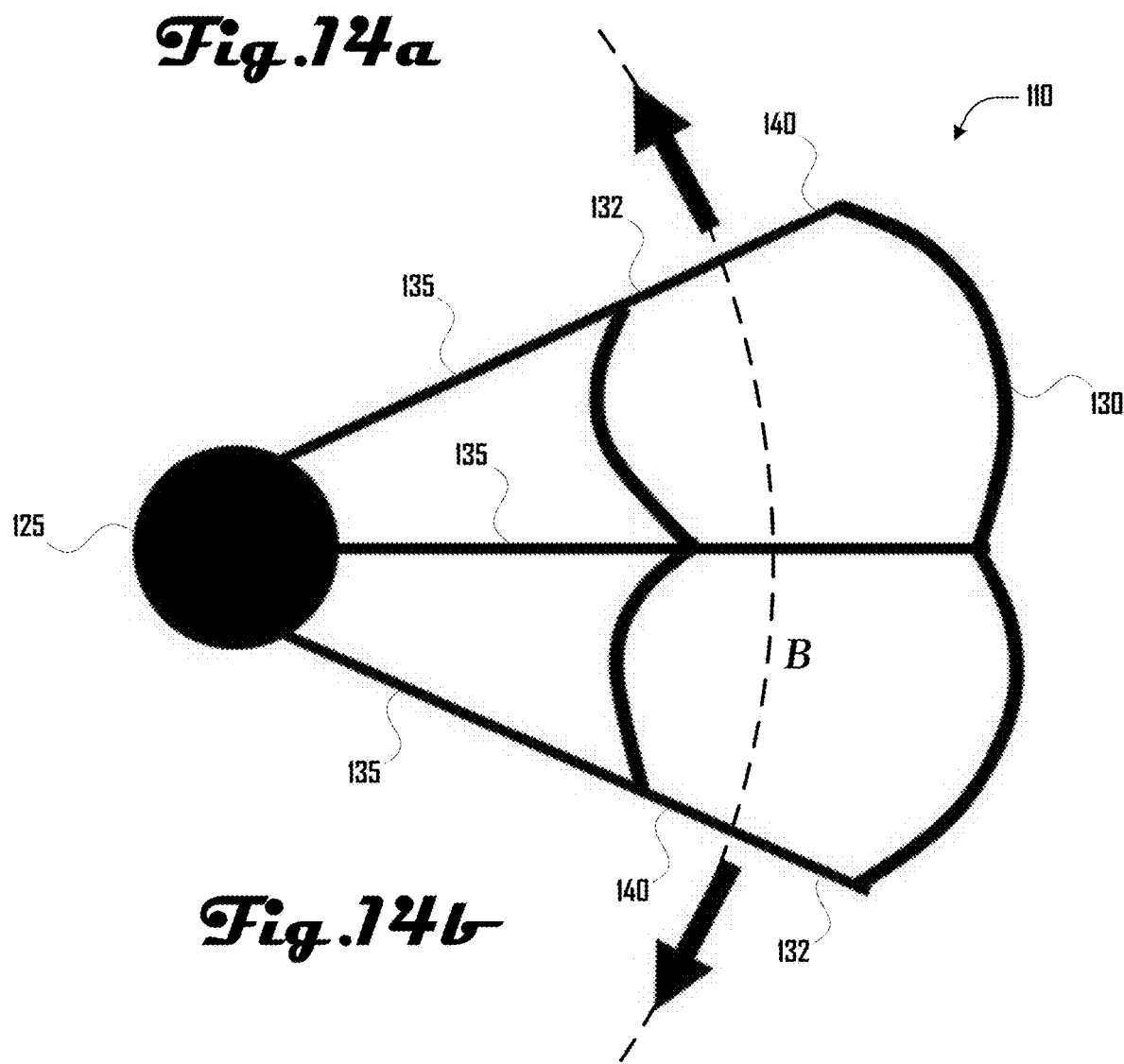
FIG. 14b illustrates a side view of the pneumatic actuator of FIG. 14a in an expanded configuration.
Figure 15A:
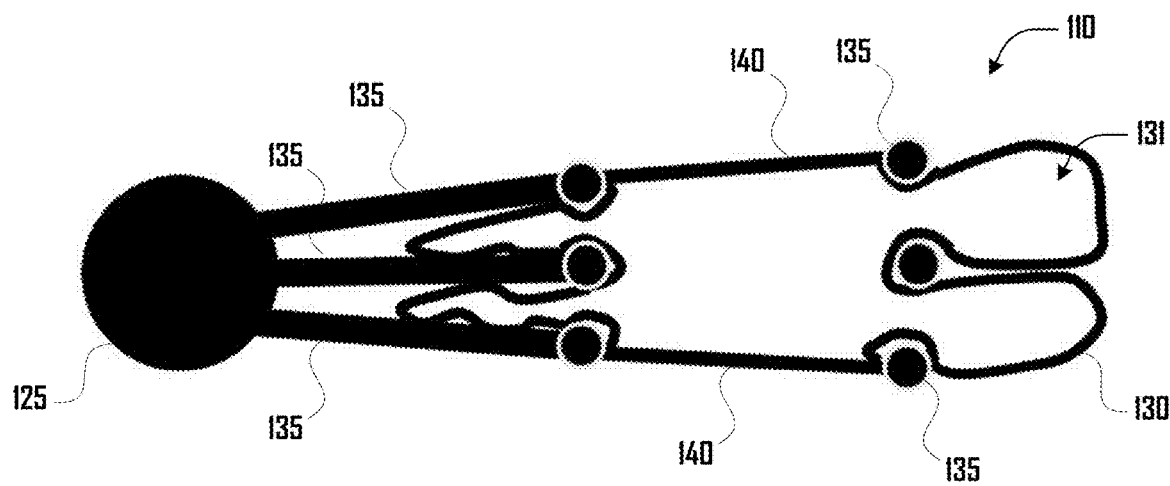
FIG. 15a illustrates a cross-sectional side view of a pneumatic actuator in a compressed configuration in accordance with another embodiment.
Figure 15B:
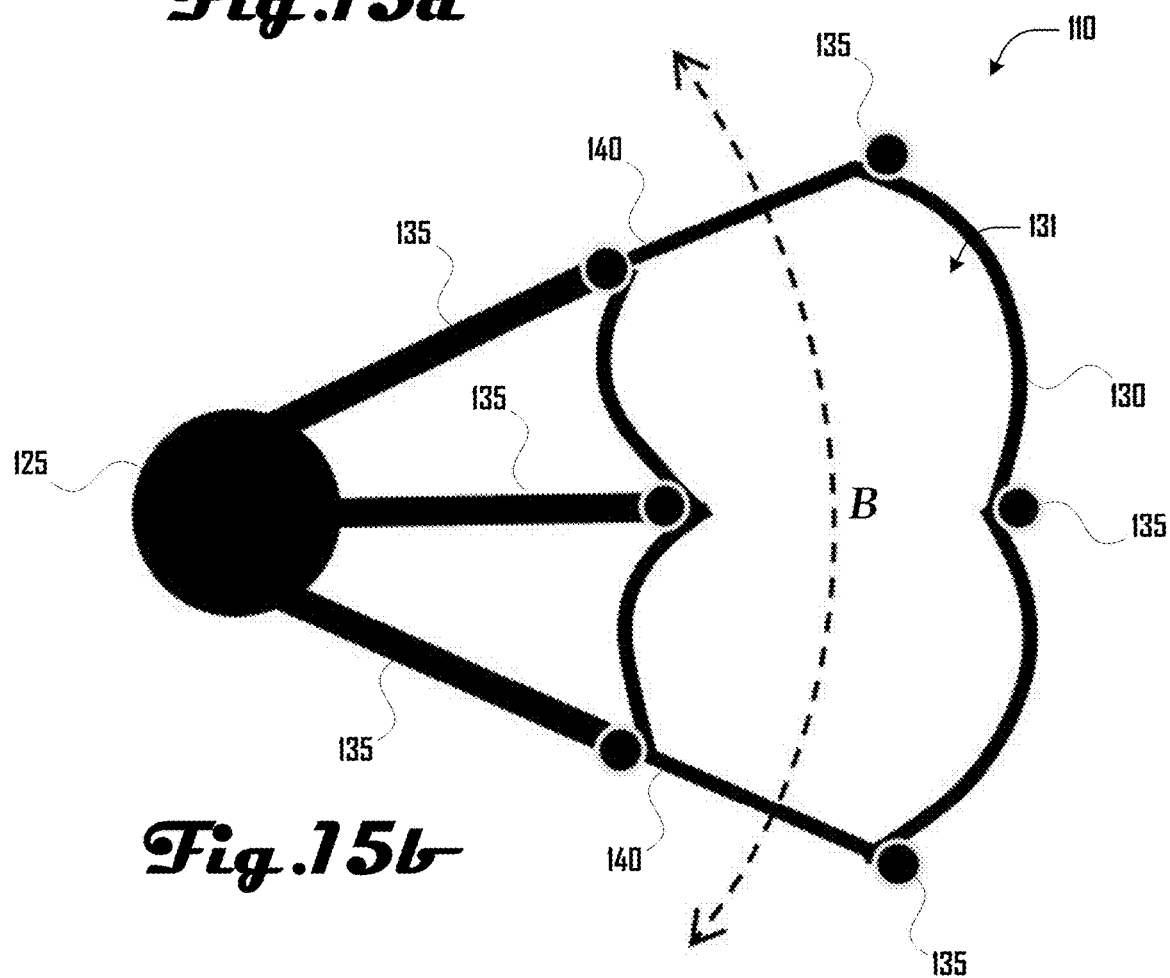
FIG. 15b illustrates a cross-sectional side view of the pneumatic actuator of FIG. 13a in an expanded configuration.

Turning to FIGS. 14a, 14b, 15a and 15b, examples of a leg actuator unit 110 can include the joint 125, bellows actuator 130, constraint ribs 135, and base plates 140. More specifically, FIG. 14a illustrates a side view of a leg actuator unit 110 in a compressed configuration and FIG. 14b illustrates a side view of the leg actuator unit 110 of FIG. 14a in an expanded configuration. FIG. 15a illustrates a cross-sectional side view of a leg actuator unit 110 in a compressed configuration and FIG. 15b illustrates a cross-sectional side view of the leg actuator unit 110 of FIG. 15a in an expanded configuration.

As shown in FIGS. 14a, 14b, 15a and 15b, the joint 125 can have a plurality of constraint ribs 135 extending from and coupled to the joint 125, which surround or abut a portion of the bellows actuator 130. For example, in some embodiments, constraint ribs 135 can abut the ends 132 of the bellows actuator 130 and can define some or all of the base plates 140 that the ends 132 of the bellows actuator 130 can push against. However, in some examples, the base plates 140 can be separate and/or different elements than the constraint ribs 135 (e.g., as shown in FIG. 1). Additionally, one or more constraint ribs 135 can be disposed between ends 132 of the bellows actuator 130. For example, FIGS. 14a, 14b, 15a and 15b illustrate one constraint rib 135 disposed between ends 132 of the bellows actuator 130; however, further embodiments can include any suitable number of constraint ribs 135 disposed between ends of the bellows actuator 130, including 1, 2, 3, 4, 5, 6, 7, 8, 9, 10, 15, 20, 25, 30, 50, 100 and the like. In some embodiments, constraint ribs can be absent.

As shown in cross sections of FIGS. 15a and 15b, the bellows actuator 130 can define a cavity 131 that can be filled with fluid (e.g., air), to expand the bellows actuator 130, which can cause the bellows to elongate along axis B as shown in FIGS. 14b and 15b. For example, increasing a pressure and/or volume of fluid in the bellows actuator 130 shown in FIG. 14a can cause the bellows actuator 130 to expand to the configuration shown in FIG. 14b. Similarly, increasing a pressure and/or volume of fluid in the bellows actuator 130 shown in FIG. 15a can cause the bellows actuator 130 to expand to the configuration shown in FIG. 15b. For clarity, the use of the term "bellows" is to describe a component in the described actuator unit 110 and is not intended to limit the geometry of the component. The bellows actuator 130 can be constructed with a variety of geometries including but not limited to a constant cylindrical tube, a cylinder of varying cross-sectional area, a 3-D woven geometry that inflates to a defined arc shape, and the like. The term 'bellows' should not be construed to necessary include a structure having convolutions.

Alternatively, decreasing a pressure and/or volume of fluid in the bellows actuator 130 shown in FIG. 14b can cause the bellows actuator 130 to contract to the configuration shown in FIG. 14a. Similarly, decreasing a pressure and/or volume of fluid in the bellows actuator 130 shown in FIG. 15b can cause the bellows actuator 130 to contract to the configuration shown in FIG. 15a. Such increasing or decreasing of a pressure or volume of fluid in the bellows actuator 130 can be performed by pneumatic system 520 and pneumatic lines 145 of the exoskeleton system 100, which can be controlled by the exoskeleton device 510 (see FIG. 5).

In one preferred embodiment, the bellows actuator 130 can be inflated with air; however, in further embodiments, any suitable fluid can be used to inflate the bellows actuator 130. For example, gasses including oxygen, helium, nitrogen, and/or argon, or the like can be used to inflate and/or deflate the bellows actuator 130. In further embodiments, a liquid such as water, an oil, or the like can be used to inflate the bellows actuator 130. Additionally, while some examples discussed herein relate to introducing and removing fluid from a bellows actuator 130 to change the pressure within the bellows actuator 130, further examples can include heating and/or cooling a fluid to modify a pressure within the bellows actuator 130.

As shown in FIGS. 14a, 14b, 15a and 15b, the constraint ribs 135 can support and constrain the bellows actuator 130. For example, inflating the bellows actuator 130 causes the bellows actuator 130 to expand along a length of the bellows actuator 130 and also cause the bellows actuator 130 to expand radially. The constraint ribs 135 can constrain radial expansion of a portion of the bellows actuator 130. Additionally, as discussed herein, the bellows actuator 130 comprise a material that is flexible in one or more directions and the constraint ribs 135 can control the direction of linear expansion of the bellows actuator 130. For example, in some embodiments, without constraint ribs 135 or other constraint structures the bellows actuator 130 would herniate or bend out of axis uncontrollably such that suitable force would not be applied to the base plates 140 such that the arms 115, 120 would not be suitably or controllably actuated. Accordingly, in various embodiments, the constraint ribs 135 can be desirable to generate a consistent and controllable axis of expansion B for the bellows actuator 130 as they are inflated and/or deflated.

In some examples, the bellows actuator 130 in a deflated configuration can substantially extend past a radial edge of the constraint ribs 135 and can retract during inflation to extend less past the radial edge of the constraint ribs 135, to extend to the radial edge of the constraint ribs 135, or not to extend less past the radial edge of the constraint ribs 135. For example, FIG. 15a illustrates a compressed configuration of the bellows actuator 130 where the bellows actuator 130 substantially extend past a radial edge of the constraint ribs 135 and FIG. 15b illustrates the bellows actuator 130 retracting during inflation to extend less past the radial edge of the constraint ribs 135 in an inflated configuration of the bellows actuator 130.

Figure 16A:
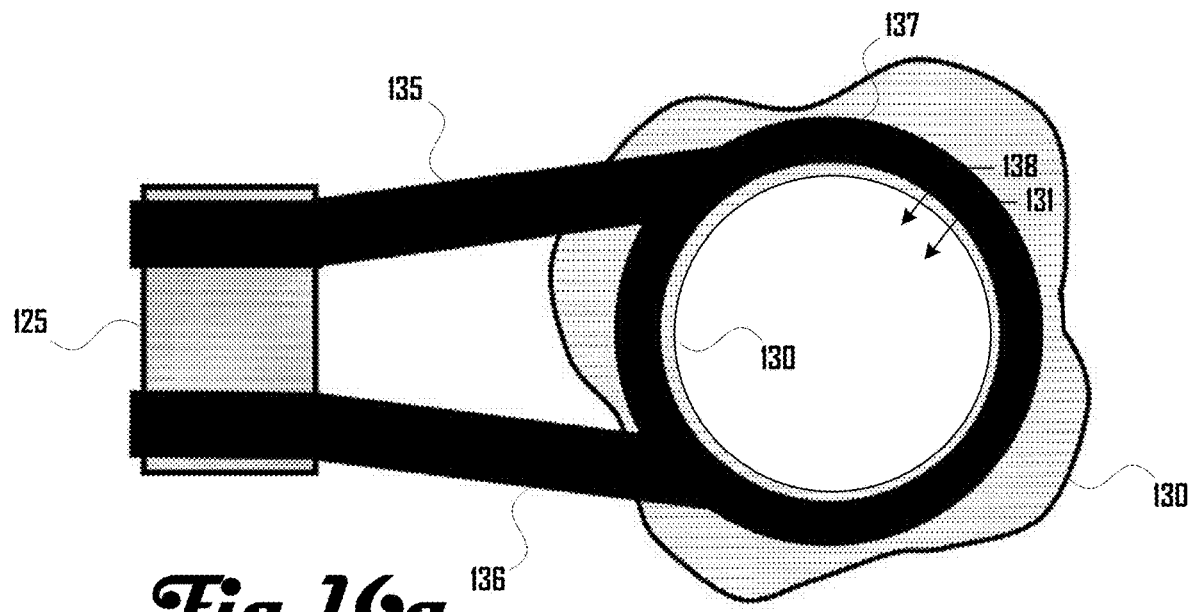
FIG. 16a illustrates a top view of a pneumatic actuator in a compressed configuration in accordance with another embodiment.
Figure 16B:
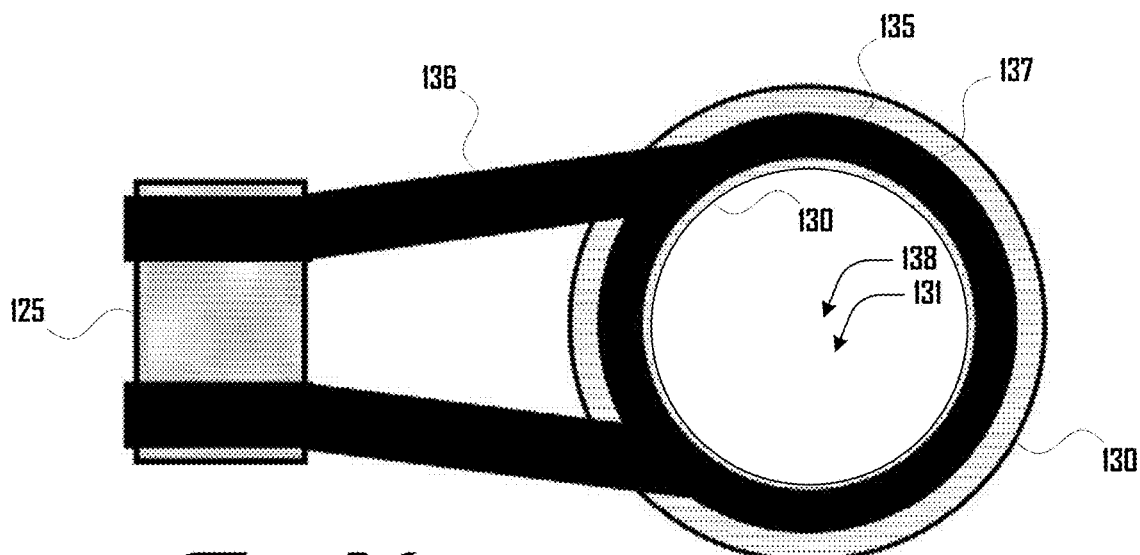
FIG. 16b illustrates a top of the pneumatic actuator of FIG. 16a in an expanded configuration.

Similarly, FIG. 16a illustrates a top view of a compressed configuration of bellows actuator 130 where the bellows actuator 130 substantially extend past a radial edge of constraint ribs 135 and FIG. 16b illustrates a top view where the bellows actuator 130 retract during inflation to extend less past the radial edge of the constraint ribs 135 in an inflated configuration of the bellows actuator 130.

Figure 17:
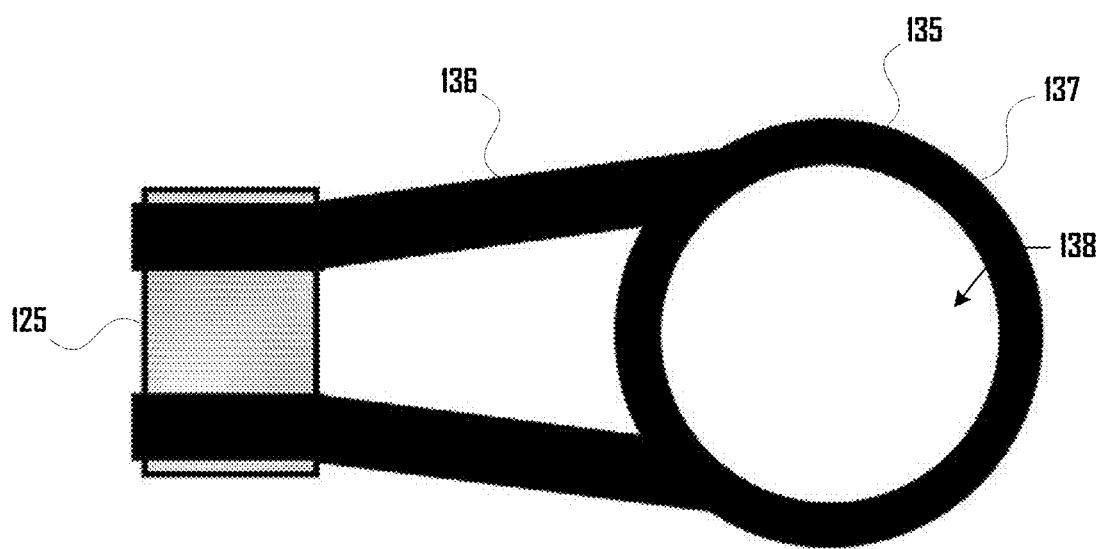
FIG. 17 illustrates a top view of a pneumatic actuator constraint rib in accordance with an embodiment.

Constraint ribs 135 can be configured in various suitable ways. For example, FIGS. 16a, 16b and 17 illustrate a top view of an example embodiment of a constraint rib 135 having a pair of rib arms 136 that extend from the joint structure 125 and couple with a circular rib ring 137 that defines a rib cavity 138 through which a portion of the bellows actuator 130 can extend (e.g., as shown in FIGS. 15a, 15b, 16a and 16b). In various examples, the one or more constraint ribs 135 can be a substantially planar element with the rib arms 136 and rib ring 137 being disposed within a common plane.

In further embodiments, the one or more constraint ribs 135 can have any other suitable configuration. For example, some embodiments can have any suitable number of rib arms 136, including one, two, three, four, five, or the like. Additionally, the rib ring 137 can have various suitable shapes and need not be circular, including one or both of an inner edge that defines the rib cavity 138 or an outer edge of the rib ring 137.

In various embodiments, the constraining ribs 135 can be configured to direct the motion of the bellows actuator 130 through a swept path about some instantaneous center (which may or may not be fixed in space) and/or to prevent motion of the bellows actuator 130 in undesired directions, such as out-of-plane buckling. As a result, the number of constraining ribs 135 included in some embodiments can vary depending on the specific geometry and loading of the leg actuator unit 110. Examples can range from one constraining rib 135 up to any suitable number of constraining ribs 135; accordingly, the number of constraining ribs 135 should not be taken to limit the applicability of the invention. Additionally, constraining ribs 135 can be absent in some embodiments.

The one or more constraining ribs 135 can be constructed in a variety of ways. For example the one or more constraining ribs 135 can vary in construction on a given leg actuator unit 110, and/or may or may not require attachment to the joint structure 125. In various embodiments, the constraining ribs 135 can be constructed as an integral component of a central rotary joint structure 125. An example embodiment of such a structure can include a mechanical rotary pin joint, where the constraining ribs 135 are connected to and can pivot about the joint 125 at one end of the joint structure 125, and are attached to an inextensible outer layer of the bellows actuator 130 at the other end. In another set of embodiments, the constraining ribs 135 can be constructed in the form of a single flexural structure that directs the motion of the bellows actuator 130 throughout the range of motion for the leg actuator unit 110. Another example embodiment uses a flexural constraining rib 135 that is not connected integrally to the joint structure 125 but is instead attached externally to a previously assembled joint structure 125. Another example embodiment can comprise the constraint ribs 135 being composed of pieces of fabric wrapped around the bellows actuator 130 and attached to the joint structure 125, acting like a hammock to restrict and/or guide the motion of the bellows actuator 130. There are additional methods available for constructing the constraining ribs 135 that can be used in additional embodiments that include but are not limited to a linkage, a rotational flexure connected around the joint structure 125, and the like.

In some examples, a design consideration for constraining ribs 135 can be how the one or more constraining ribs 135 interact with the bellows actuator 130 to guide the path of the bellows actuator 130. In various embodiments, the constraining ribs 135 can be fixed to the bellows actuator 130 at predefined locations along the length of the bellows actuator 130. One or more constraining ribs 135 can be coupled to the bellows actuator 130 in various suitable ways, including but not limited to sewing, mechanical clamps, geometric interference, direct integration, and the like. In other embodiments, the constraining ribs 135 can be configured such that the constraining ribs 135 float along the length of the bellows actuator 130 and are not fixed to the bellows actuator 130 at predetermined connection points. In some embodiments, the constraining ribs 135 can be configured to restrict a cross sectional area of the bellows actuator 130. An example embodiment can include a tubular bellows actuator 130 attached to a constraining rib 135 that has an oval cross section, which in some examples can be a configuration to reduce the width of the bellows actuator 130 at that location when the bellows actuator 130 is inflated.

The bellows actuator 130 can have various functions in some embodiments, including containing operating fluid of the leg actuator unit 110, resisting forces associated with operating pressure of the leg actuator unit 110, and the like. In various examples, the leg actuator unit 110 can operate at a fluid pressure above, below or at about ambient pressure. In various embodiments, bellows actuator 130 can comprise one or more flexible, yet inextensible or practically inextensible materials in order to resist expansion (e.g., beyond what is desired in directions other than an intended direction of force application or motion) of the bellows actuator 130 beyond what is desired when pressurized above ambient pressure. Additionally, the bellows actuator 130 can comprise an impermeable or semi-impermeable material in order to contain the actuator fluid.

Figure 19:
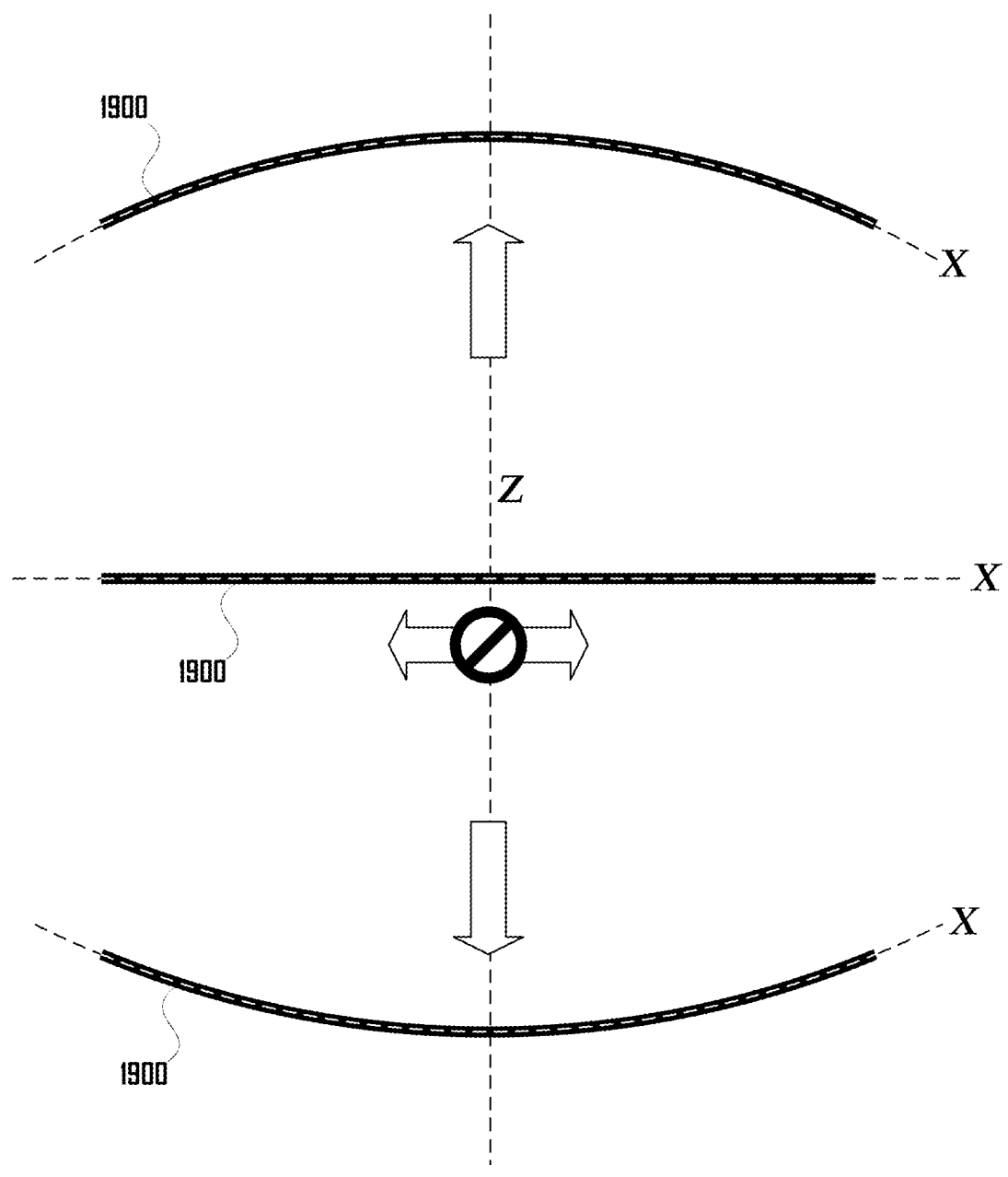
FIG. 19 illustrates an example planar material that is substantially inextensible along one or more plane axes of the planar material while being flexible in other directions.

For example, in some embodiments, the bellows actuator 130 can comprise a flexible sheet material such as woven nylon, rubber, polychloroprene, a plastic, latex, a fabric, or the like. Accordingly, in some embodiments, bellows actuator 130 can be made of a planar material that is substantially inextensible along one or more plane axes of the planar material while being flexible in other directions. For example, FIG. 19 illustrates a side view of a planar material 1900 (e.g., a fabric) that is substantially inextensible along axis X that is coincident with the plane of the material 1900, yet flexible in other directions, including axis Z. In the example of FIG. 19, the material 1900 is shown flexing upward and downward along axis Z while being inextensible along axis X. In various embodiments, the material 1900 can also be inextensible along an axis Y (not shown) that is also coincident with the plane of the material 1900 like axis X and perpendicular to axis X.

In some embodiments, the bellows actuator 130 can be made of a non-planar woven material that is inextensible along one or more axes of the material. For example, in one embodiment the bellows actuator 130 can comprise a woven fabric tube. Woven fabric material can provide inextensibility along the length of the bellows actuator 130 and in the circumferential direction. Such embodiments can still be able to be configured along the body of the user 101 to align with the axis of a desired joint on the body 101 (e.g., the knee 103).

In various embodiments, the bellows actuator 130 can develop its resulting force by using a constrained internal surface length and/or external surface length that are a constrained distance away from each other (e.g. due to an inextensible material as discussed above). In some examples, such a design can allow the actuator to contract on bellows actuator 130, but when pressurized to a certain threshold, the bellows actuator 130 can direct the forces axially by pressing on the plates 140 of the leg actuator unit 110 because there is no ability for the bellows actuator 130 to expand further in volume otherwise due to being unable to extend its length past a maximum length defined by the body of the bellows actuator 130.

In other words, the bellows actuator 130 can comprise a substantially inextensible textile envelope that defines a chamber that is made fluid-impermeable by a fluid-impermeable bladder contained in the substantially inextensible textile envelope and/or a fluid-impermeable structure incorporated into the substantially inextensible textile envelope. The substantially inextensible textile envelope can have a predetermined geometry and a non-linear equilibrium state at a displacement that provides a mechanical stop upon pressurization of the chamber to prevent excessive displacement of the substantially inextensible textile actuator.

In some embodiments, the bellows actuator 130 can include an envelope that consists or consists essentially of inextensible textiles (e.g., inextensible knits, woven, non-woven, etc.) that can prescribe various suitable movements as discussed herein. Inextensible textile bellows actuator 130 can be designed with specific equilibrium states (e.g., end states or shapes where they are stable despite increasing pressure), pressure/stiffness ratios, and motion paths. Inextensible textile bellows actuator 130 in some examples can be configured accurately delivering high forces because inextensible materials can allow greater control over directionality of the forces.

Accordingly, some embodiments of inextensible textile bellows actuator 130 can have a pre-determined geometry that produces displacement mostly via a change in the geometry between the uninflated shape and the pre-determined geometry of its equilibrium state (e.g., fully inflated shape) due to displacement of the textile envelope rather than via stretching of the textile envelope during a relative increase in pressure inside the chamber; in various embodiments, this can be achieved by using inextensible materials in the construction of the envelope of the bellows actuator 130. As discussed herein, in some examples "inextensible"

or "substantially inextensible" can be defined as expansion by no more than 10%, no more than 5%, or no more than 1% in one or more direction.

Figure 18A:
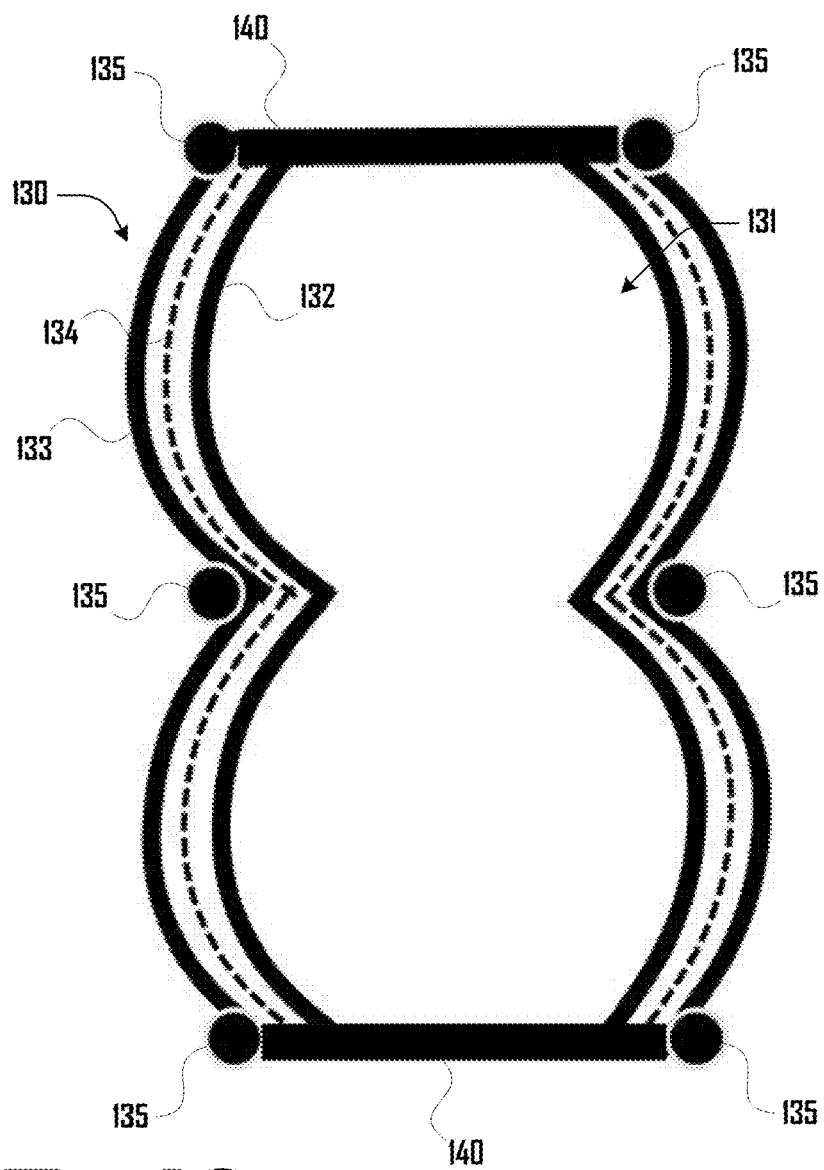
FIG. 18a illustrates a cross-sectional view of a pneumatic actuator bellows in accordance with another embodiment.
Figure 18B:
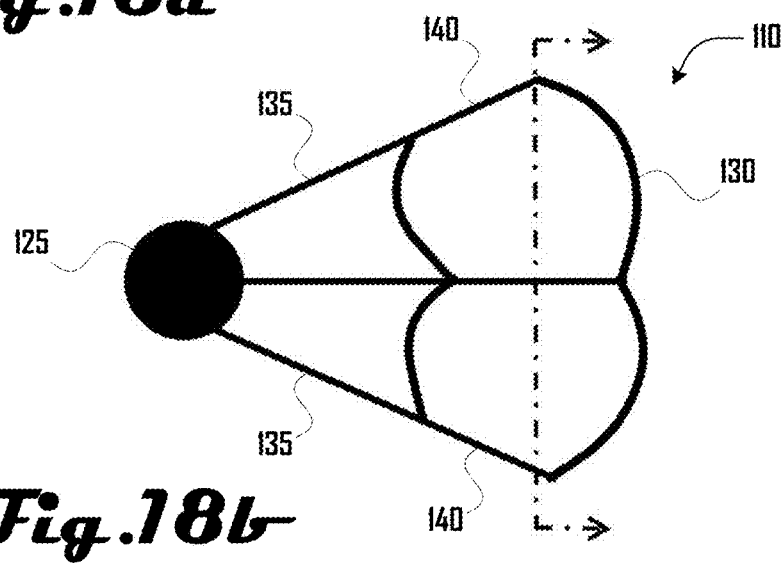

FIG. 18a illustrates a cross-sectional view of a pneumatic actuator unit 110 including bellows actuator 130 in accordance with another embodiment and FIG. 18b illustrates a side view of the pneumatic actuator unit 110 of FIG. 18a in an expanded configuration showing the cross section of FIG. 18a. As shown in FIG. 18a, the bellows actuator 130 can comprise an internal first layer 132 that defines the bellows cavity 131 and can comprise an outer second layer 133 with a third layer 134 disposed between the first and second layers 132, 133. Throughout this description, the use of the term "layer" to describe the construction of the bellows actuator 130 should not be viewed as limiting to the design. The use of 'layer' can refer to a variety of designs including but not limited to: a planar material sheet, a wet film, a dry film, a rubberized coating, a co-molded structure, and the like.

In some examples, the internal first layer 132 can comprise a material that is impermeable or semi-permeable to the actuator fluid (e.g., air) and the external second layer 133 can comprise an inextensible material as discussed herein. For example, as discussed herein, an impermeable layer can refer to an impermeable or semi-permeable layer and an inextensible layer can refer to an inextensible or a practically inextensible layer.

In some embodiments comprising two or more layers, the internal layer 132 can be slightly oversized compared to an inextensible outer second layer 133 such that the internal forces can be transferred to the high-strength inextensible outer second layer 133. One embodiment comprises a bellows actuator 130 with an impermeable polyurethane polymer film inner first layer 132 and a woven nylon braid as the outer second layer 133.

The bellows actuator 130 can be constructed in various suitable ways in further embodiments, which can include a single-layer design that is constructed of a material that provides both fluid impermeability and that is sufficiently inextensible. Other examples can include a complex bellows assembly that comprises multiple laminated layers that are fixed together into a single structure. In some examples, it can be necessary to limit the deflated stack height of the bellows actuator 130 to maximize the range of motion of the leg actuator unit 110. In such an example, it can be desirable to select a low-thickness fabric that meets the other performance needs of the bellows actuator 130.

In yet another embodiment, it can be desirable to reduce friction between the various layers of the bellows actuator 130. In one embodiment, this can include the integration of a third layer 134 that acts as an anti-abrasive and/or low friction intermediate layer between the first and second layers 132, 133. Other embodiments can reduce the friction between the first and second layers 132, 133 in alternative or additional ways, including but not limited to the use of a wet lubricant, a dry lubricant, or multiple layers of low friction material. Accordingly, while the example of FIG. 16a illustrates an example of a bellows actuator 130 comprising three layers 132, 133, 134, further embodiments can include a bellows actuator 130 having any suitable number of layers, including one, two, three, four, five, ten, fifteen, twenty-five, and the like. Such one or more layers can be coupled along adjoining faces in part or in whole, with some examples defining one or more cavities between layers. In such examples, material such as lubricants or other suitable fluids can be disposed in such cavities or such cavities can be effectively empty. Additionally, as described herein, one or more layers (e.g., the third layer 134) need not be a sheet or planar material layer as shown in some examples and can instead comprise a layer defined by a fluid. For example, in some embodiments, the third layer 134 can be defined by a wet lubricant, a dry lubricant, or the like.

The inflated shape of the bellows actuator 130 can be important to the operation of the bellows actuator 130 and/or leg actuator unit 110 in some embodiments. For example, the inflated shape of the bellows actuator 130 can be affected through the design of both an impermeable and inextensible portion of the bellows actuator 130 (e.g., the first and second layer 132, 133). In various embodiments, it can be desirable to construct one or more of the layers 132, 133, 134 of the bellows actuator 130 out of various two-dimensional panels that may not be intuitive in a deflated configuration.

In some embodiments, one or more impermeable layers can be disposed within the bellows cavity 131 and/or the bellows actuator 130 can comprise a material that is capable of holding a desired fluid (e.g., a fluid impermeable first internal layer 132 as discussed herein). The bellows actuator 130 can comprise a flexible, elastic, or deformable material that is operable to expand and contract when the bellows actuator 130 are inflated or deflated as described herein. In some embodiments, the bellows actuator 130 can be biased toward a deflated configuration such that the bellows actuator 130 is elastic and tends to return to the deflated configuration when not inflated. Additionally, although bellows actuator 130 shown herein are configured to expand and/or extend when inflated with fluid, in some embodiments, bellows actuator 130 can be configured to shorten and/or retract when inflated with fluid in some examples. Also, the term "bellows" as used herein should not be construed to be limiting in any way. For example the term "bellows" as used herein should not be construed to require elements such as convolutions or other such features (although convoluted bellows actuator 130 can be present in some embodiments). As discussed herein, bellows actuator 130 can take on various suitable shapes, sizes, proportions and the like.

The bellows actuator 130 can vary significantly across various embodiments, so the present examples should not be construed to be limiting. One preferred embodiment of a bellows actuator 130 includes fabric-based pneumatic actuator configured such that it provides knee extension torque as discussed herein. Variants of this embodiment can exist to tailor the actuator to provide the desired performance characteristics of the actuators such as a fabric actuator that is not of a uniform cross-section. Other embodiments can use an electro-mechanical actuator configured to provide flexion and extension torques at the knee instead of or in addition to a fluidic bellows actuator 130. Various embodiments can include but are not limited to designs that incorporate combinations of electromechanical, hydraulic, pneumatic, electro-magnetic, or electro-static for positive power or negative power assistance of extension or flexion of a lower extremity joint.

The actuator bellows actuator 130 can also be located in a variety of locations as required by the specific design. One embodiment places the bellows actuator 130 of a powered knee brace component located in line with the axis of the knee joint and positioned parallel to the joint itself. Various embodiments include but are not limited to, actuators configured in series with the joint, actuators configured anterior to the joint, and actuators configured to rest around the joint.

Various embodiments of the bellows actuator 130 can include secondary features that augment the operation of the actuation. One such embodiment is the inclusion of user-adjustable mechanical hard end stops to limit the allowable range of motion to the bellows actuator 130. Various embodiments can include but are not limited to the following extension features: the inclusion of flexible end stops, the inclusion of an electromechanical brake, the inclusion of an electro-magnetic brake, the inclusion of a magnetic brake, the inclusion of a mechanical disengage switch to mechanically decouple the joint from the actuator, or the inclusion of a quick release to allow for quick changing of actuator components.

In various embodiments, the bellows actuator 130 can comprise a bellows and/or bellows system as described in related U.S. patent application Ser. No. 14/064,071 filed Oct. 25, 2013, which issued as U.S. Pat. No. 9,821,475; as described in U.S. patent application Ser. No. 14/064,072 filed Oct. 25, 2013; as described in U.S. patent application Ser. No. 15/823,523 filed Nov. 27, 2017; or as described in U.S. patent application Ser. No. 15/472,740 filed Mar. 29, 2017.

In some applications, the design of the fluidic actuator unit 110 can be adjusted to expand its capabilities. One example of such a modification can be made to tailor the torque profile of a rotary configuration of the fluidic actuator unit 110 such that the torque changes as a function of the angle of the joint structure 125. To accomplish this in some examples, the cross-section of the bellows actuator 130 can be manipulated to enforce a desired torque profile of the overall fluidic actuator unit 110. In one embodiment, the diameter of the bellows actuator 130 can be reduced at a longitudinal center of the bellows actuator 130 to reduce the overall force capabilities at the full extension of the bellows actuator 130. In yet another embodiment, the cross-sectional areas of the bellows actuator 130 can be modified to induce a desired buckling behavior such that the bellows actuator 130 does not get into an undesirable configuration. In an example embodiment, the end configurations of the bellows actuator 130 of a rotary configuration can have the area of the ends reduced slightly from the nominal diameter to provide for the end portions of the bellows actuator 130 to buckle under loading until the actuator unit 110 extends beyond a predetermined joint angle, at which point the smaller diameter end portion of the bellows actuator 130 would begin to inflate.

In other embodiments, this same capability can be developed by modifying the behavior of the constraining ribs 135. As an example embodiment, using the same example bellows actuator 130 as discussed in the previous embodiment, two constraining ribs 135 can fixed to such bellows actuator 130 at evenly distributed locations along the length of the bellows actuator 130. In some examples, a goal of resisting a partially inflated buckling can be combated by allowing the bellows actuator 130 to close in a controlled manner as the actuator unit 110 closes. The constraining ribs 135 can be allowed to get closer to the joint structure 125 but not closer to each other until they have bottomed out against the joint structure 125. This can allow the center portion of the bellows actuator 130 to remain in a fully inflated state which can be the strongest configuration of the bellows actuator 130 in some examples.

In further embodiments, it can be desirable to optimize the fiber angle of the individual braid or weave of the bellows actuator 130 in order to tailor specific performance characteristics of the bellows actuator 130 (e.g., in an example where a bellows actuator 130 includes inextensibility provided by a braided or woven fabric). In other embodiments, the geometry of the bellows actuator 130 of the actuator unit 110 can be manipulated to allow the robotic exoskeleton system 100 to operate with different characteristics. Example methods for such modification can include but are not limited to the following: the use of smart materials on the bellows actuator 130 to manipulate the mechanical behavior of the bellows actuator 130 on command; or the mechanical modification of the geometry of the bellows actuator 130 through means such as shortening the operating length and/or reducing the cross sectional area of the bellows actuator 130.

In further examples, a fluidic actuator unit 110 can comprise a single bellows actuator 130 or a combination of multiple bellows actuator 130, each with its own composition, structure, and geometry. For example, some embodiments can include multiple bellows actuator 130 disposed in parallel or concentrically on the same joint assembly 125 that can be engaged as needed. In one example embodiment, a joint assembly 125 can be configured to have two bellows actuator 130 disposed in parallel directly next to each other. The exoskeleton system 100 can selectively choose to engage each bellows actuator 130 as needed to allow for various amounts of force to be output by the same fluidic actuator unit 110 in a desirable mechanical configuration.

In further embodiments, a fluidic actuator unit 110 can include various suitable sensors to measure mechanical properties of the bellows actuator 130 or other portions of the fluidic actuator unit 110 that can be used to directly or indirectly estimate pressure, force, or strain in the bellows actuator 130 or other portions of the fluidic actuator unit 110. In some examples, sensors located at the fluidic actuator unit 110 can be desirable due to the difficulty in some embodiments associated with the integration of certain sensors into a desirable mechanical configuration while others may be more suitable. Such sensors at the fluidic actuator unit 110 can be operably connected to the exoskeleton device 610 (see FIG. 6) and the exoskeleton device 610 can use data from such sensors at the fluidic actuator unit 110 to control the exoskeleton system 100.

As discussed herein, various suitable exoskeleton systems 100 can be used in various suitable ways and for various suitable applications. However, such examples should not be construed to be limiting on the wide variety of exoskeleton systems 100 or portions thereof that are within the scope and spirit of the present disclosure. Accordingly, exoskeleton systems 100 that are more or less complex than the examples of FIGS. 1-5 are within the scope of the present disclosure.

Additionally, while various examples relate to an exoskeleton system 100 associated with the legs or lower body of a user, further examples can be related to any suitable portion of a user body including the torso, arms, head, legs, or the like. Also, while various examples relate to exoskeletons, it should be clear that the present disclosure can be applied to other similar types of technology, including prosthetics, body implants, robots, or the like. Further, while some examples can relate to human users, other examples can relate to animal users, robot users, various forms of machinery, or the like.

The described embodiments are susceptible to various modifications and alternative forms, and specific examples thereof have been shown by way of example in the drawings and are herein described in detail. It should be understood, however, that the described embodiments are not to be limited to the particular forms or methods disclosed, but to the contrary, the present disclosure is to cover all modifications, equivalents, and alternatives. Additionally, elements of a given embodiment should not be construed to be applicable to only that example embodiment and therefore elements of one example embodiment can be applicable to other embodiments. Additionally, elements that are specifically shown in example embodiments should be construed to cover embodiments that comprise, consist essentially of, or consist of such elements, or such elements can be explicitly absent from further embodiments. Accordingly, the recitation of an element being present in one example should be construed to support some embodiments where such an element is explicitly absent.

What is claimed is:

1. A method of operating a modular exoskeleton system, the method comprising:
monitoring, by an electronic exoskeleton device of the modular exoskeleton system, for one or more leg actuator units being operably coupled to or removed from the modular exoskeleton system, the modular exoskeleton system comprising:
a left and right leg actuator unit configured to be respectively coupled to a left leg and a right leg of a user and configured to be operably coupled and removed from the modular exoskeleton system, the left and right leg actuator units each including:
an upper arm and a lower arm that are rotatably coupled via a joint, the joint positioned at a knee of the user with the upper arm coupled about an upper leg portion of the user above the knee and with the lower arm coupled about a lower leg portion of the user below the knee,
a bellows actuator that extends between the upper arm and lower arms, and
one or more sets of lines including at least a fluid line coupled to the bellows actuator configured to introduce fluid to the bellows actuator to cause the bellows actuator to expand and move the upper arm and lower arm and a sensor line configured to obtain data from one or more sensors of the leg actuator unit, the one or more sets of lines configured to be removably operably coupled to the modular exoskeleton system via one or more line couplings;
determining, by the electronic exoskeleton device of the modular exoskeleton system, that the left leg actuator unit has been operably coupled to the modular exoskeleton system via the one or more line couplings while the right leg actuator unit was already operably coupled to the modular exoskeleton system and coupled to the right leg of the user;
determining, by the electronic exoskeleton device of the modular exoskeleton system, that the left leg actuator unit has been coupled to the left leg of the user;
determining, by the electronic exoskeleton device of the modular exoskeleton system, a first new operating configuration based at least in part on the determination that the left leg actuator unit has been operably coupled to the modular exoskeleton system via the one or more line couplings while the right leg actuator unit was already operably coupled to the modular exoskeleton system and coupled to the right leg of the user, the first new operating configuration including a dual-knee operating configuration;
setting, by the electronic exoskeleton device of the modular exoskeleton system, the dual-knee operating configuration for the modular exoskeleton system in place of a single-right-knee operating configuration that was previously set based at least in part on the right leg actuator unit being operably coupled to the modular exoskeleton system and determined as being coupled to the right leg of the user;
determining, by the electronic exoskeleton device of the modular exoskeleton system, that the left leg actuator unit has been operably de-coupled from the modular exoskeleton system via the one or more line couplings while the right leg actuator unit remains operably coupled to the modular exoskeleton system and coupled to the right leg of the user;
determining, by the electronic exoskeleton device of the modular exoskeleton system, a second new operating configuration based at least in part on the determination that the left leg actuator unit has been operably de-coupled from the modular exoskeleton system via the one or more line couplings while the right leg actuator unit remains operably coupled to the modular exoskeleton system and coupled to the right leg of the user, the second new operating configuration including the single-right-knee operating configuration; and
setting, by the electronic exoskeleton device of the modular exoskeleton system, the single-right-knee operating configuration for the modular exoskeleton system in place of the dual-knee operating configuration.

2. The method of operating a modular exoskeleton system of claim 1, wherein the determining that the left leg actuator unit has been coupled to the left leg of the user includes the electronic exoskeleton device obtaining an identifier associated with the left leg actuator unit, the identifier associated with information that indicates that the left leg actuator unit is specifically configured for being coupled to the left leg of the user and not for being coupled to the right leg of the user.

3. The method of operating a modular exoskeleton system of claim 1, wherein the determining that the left leg actuator unit has been coupled to the left leg of the user is based at least in part on a determination that the left leg actuator unit has been operably coupled to the modular exoskeleton system via a left leg line coupler.

4. The method of operating a modular exoskeleton system of claim 1, wherein the setting the dual-knee operating configuration for the modular exoskeleton system includes determining different settings of the left and right leg actuation units based on different user needs between left leg and right leg of the user.

5. A method of operating a modular exoskeleton system, the method comprising:
monitoring for one or more leg actuator units being operably coupled to or removed from the modular exoskeleton system, the modular exoskeleton system comprising a left and right leg actuator unit configured to be respectively coupled to a left leg and a right leg of a user and configured to be operably coupled and removed from the modular exoskeleton system;
determining that the left leg actuator unit has been operably coupled to the modular exoskeleton system while the right leg actuator unit was already operably coupled to the modular exoskeleton system;
determining that the left leg actuator unit has been associated with the left leg of the user;
determining a first new operating configuration based at least in part on the determination that the left leg actuator unit has been operably coupled to the modular exoskeleton system while the right leg actuator unit was already operably coupled to the modular exoskeleton system and associated with the right leg of the user, the first new operating configuration including a dual-knee operating configuration; and
setting the dual-knee operating configuration for the modular exoskeleton system in place of a single-right-knee operating configuration that was previously set based at least in part on the right leg actuator unit being operably coupled to the modular exoskeleton system.

6. The method of operating a modular exoskeleton system of claim 5, wherein the left and right leg actuator units each comprise:
an upper arm and a lower arm that are rotatably coupled via a joint, the joint positioned at a knee of the user with the upper arm coupled about an upper leg portion of the user above the knee and with the lower arm coupled about a lower leg portion of the user below the knee,
an actuator that extends between the upper arm and lower arms, and
one or more sets of lines configured to be removably operably coupled to the modular exoskeleton system via one or more line couplings.

7. The method of operating a modular exoskeleton system of claim 5, wherein the left leg actuator unit is physically operably coupled to the modular exoskeleton system via one or more line couplings.

8. The method of operating a modular exoskeleton system of claim 5, further comprising:
determining that the left leg actuator unit has been operably de-coupled from the modular exoskeleton system while the right leg actuator unit remains operably coupled to the modular exoskeleton system;
determining a second new operating configuration based at least in part on the determination that the left leg actuator unit has been operably de-coupled from the modular exoskeleton system while the right leg actuator unit remains operably coupled to the modular exoskeleton system, the second new operating configuration including the single-right-knee operating configuration; and
setting the single-right-knee operating configuration for the modular exoskeleton system in place of the dual-knee operating configuration.

9. The method of operating a modular exoskeleton system of claim 5, wherein the determining that the left leg actuator unit has been coupled to the left leg of the user includes obtaining an identifier associated with the left leg actuator unit, the identifier associated with information that indicates that the left leg actuator unit is specifically configured for being coupled to the left leg of the user.

10. The method of operating a modular exoskeleton system of claim 5, wherein the determining that the left leg actuator unit has been coupled to the left leg of the user is based at least in part on a determination that the left leg actuator unit has been operably coupled to the modular exoskeleton system via a left leg line coupler.

11. The method of operating a modular exoskeleton system of claim 5, wherein the setting the dual-knee operating configuration for the modular exoskeleton system includes determining different settings of the left and right leg actuation units based on different user needs between left leg and right leg of the user.

12. A method of operating a modular exoskeleton system, the method comprising:
monitoring for one or more actuator units being operably coupled to or removed from the modular exoskeleton system, the modular exoskeleton system comprising at least a first actuator unit configured to be operably coupled and removed from the modular exoskeleton system;
determining that the first actuator unit has been operably coupled to the modular exoskeleton system;
determining that the first actuator unit has been associated with a first body portion of a user;

determining a first new operating configuration based at least in part on the determination that the first actuator unit has been operably coupled to the modular exoskeleton system and the determination that the first actuator unit has been associated with the first body portion of the user; and
setting the first new operating configuration for the modular exoskeleton system in place of a single body portion operating configuration that was previously set based at least in part on a second actuator unit being operably coupled to the modular exoskeleton system.

13. A method of operating a modular exoskeleton system, the method comprising:
monitoring for one or more actuator units being operably coupled to or removed from the modular exoskeleton system, the modular exoskeleton system comprising at least a first actuator unit configured to be operably coupled and removed from the modular exoskeleton system;
determining that the first actuator unit has been operably coupled to the modular exoskeleton system;
determining that the first actuator unit has been associated with a first body portion of a user;
determining that the first actuator unit has been operably coupled to the modular exoskeleton system while a second actuator unit was already operably coupled to the modular exoskeleton system
determining a first new operating configuration based at least in part on:
the determination that the first actuator unit has been operably coupled to the modular exoskeleton system and the determination that the first actuator unit has been associated with the first body portion of the user, and
the determination that the first actuator unit has been operably coupled to the modular exoskeleton system while the second actuator unit was already operably coupled to the modular exoskeleton system, the first new operating configuration including a dual-body portion operating configuration; and
setting the first new operating configuration for the modular exoskeleton system including the dual-body portion operating configuration, wherein the setting the dual-body portion operating configuration for the modular exoskeleton system includes determining different settings of the first and second actuator units based on different user needs between the first body portion and a second body portion of the user.

14. The method of operating a modular exoskeleton system of claim 12, wherein the first actuator unit comprises:
an upper arm and a lower arm that are rotatably coupled via a joint, the joint positioned at a body-joint of the user with the upper arm coupled about an upper-portion of the user above the body-joint and with the lower arm coupled about a lower-portion of the user below the body joint,
and an actuator.

15. A method of operating a modular exoskeleton system, the method comprising:
monitoring for one or more actuator units being operably coupled to or removed from the modular exoskeleton system, the modular exoskeleton system comprising at least a first actuator unit configured to be operably coupled and removed from the modular exoskeleton system;
determining that the first actuator unit has been operably coupled to the modular exoskeleton system;

determining that the first actuator unit has been associated with a first body portion of a user;

determining a first new operating configuration based at least in part on the determination that the first actuator unit has been operably coupled to the modular exoskeleton system and the determination that the first actuator unit has been associated with the first body portion of the user;

setting the first new operating configuration for the modular exoskeleton system;

determining that the first actuator unit has been operably de-coupled from the modular exoskeleton system;

determining a second new operating configuration based at least in part on the determination that the first actuator unit has been operably de-coupled from the modular exoskeleton system; and setting the second new operating configuration for the modular exoskeleton system.

16. The method of operating a modular exoskeleton system of claim 15, further comprising determining that the first actuator unit has been operably de-coupled from the modular exoskeleton system while the second actuator unit remains operably coupled to the modular exoskeleton system, the second new operating configuration including a single-body-portion operating configuration; and setting the single-body-portion operating configuration for the modular exoskeleton system in place of a dual-body-portion operating configuration.

17. The method of operating a modular exoskeleton system of claim 12, wherein the determining that the first actuator unit has been associated with the first body portion of the user includes obtaining an identifier associated with the first actuator unit, the identifier associated with information that indicates that the first actuator unit is specifically configured for being coupled to the first body portion of the user.

18. The method of operating a modular exoskeleton system of claim 12, wherein the determining that the first actuator unit has been associated with the first body portion of the user is based at least in part on a determination that the first actuator unit has been operably coupled to the modular exoskeleton system via a first-body-portion line coupler.

* * * * *